United States Patent
Rode et al.

(10) Patent No.: US 9,963,463 B2
(45) Date of Patent: May 8, 2018

(54) UREA-SUBSTITUTED INDANES AS P38 MAP KINASE INHIBITORS

(71) Applicant: TORRENT PHARMACEUTICALS LIMITED, Ahmedabad (IN)

(72) Inventors: Milind Rode, Gandhinagar (IN); Sanjay Srivastava, Gandhinagar (IN); Davindar Tuli, Gandhinagar (IN); Deepak Rai, Gandhinagar (IN); Prashant Gj, Gandhinagar (IN); Shailesh Deshpande, Gandhinagar (IN); Rameshchandra Gupta, Gandhinagar (IN); Vijay Chauthaiwale, Gandhinagar (IN); Chaitanya Dutt, Gandhinagar (IN)

(73) Assignee: Torrent Pharmaceuticals Limited, Ahmedabad, Gujarat (IN)

( * ) Notice: Subject to any disclaimer, the term of this patent is extended or adjusted under 35 U.S.C. 154(b) by 0 days. days.

(21) Appl. No.: 15/505,902

(22) PCT Filed: Aug. 27, 2015

(86) PCT No.: PCT/IB2015/056505
§ 371 (c)(1),
(2) Date: Feb. 22, 2017

(87) PCT Pub. No.: WO2016/030852
PCT Pub. Date: Mar. 3, 2016

(65) Prior Publication Data
US 2017/0247390 A1     Aug. 31, 2017

(30) Foreign Application Priority Data
Aug. 29, 2014 (IN) .................. 2772/MUM/2014

(51) Int. Cl.
| | |
|---|---|
| *A61K 31/17* | (2006.01) |
| *C07C 275/28* | (2006.01) |
| *C07D 495/04* | (2006.01) |
| *C07D 487/04* | (2006.01) |
| *C07D 241/08* | (2006.01) |

(52) U.S. Cl.
CPC ......... *C07D 495/04* (2013.01); *C07D 241/08* (2013.01); *C07D 487/04* (2013.01)

(58) Field of Classification Search
CPC .............................. A61K 31/17; C07C 275/28
USPC ............................................. 514/740; 564/32
See application file for complete search history.

(56) References Cited

FOREIGN PATENT DOCUMENTS

| | | |
|---|---|---|
| WO | 2011/124923 A2 | 10/2011 |
| WO | WO 16/030852 * | 3/2016 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Hackam, et al. JAMA, 296(14), 2006, 1731-1732.*
International Search Report for corresponding Application No. PCT/IB2015/056505, dated Oct. 26, 2015.

* cited by examiner

*Primary Examiner* — Douglas M Willis
(74) *Attorney, Agent, or Firm* — Melissa M. Hayworth; Daniel R. Evans; E. Joseph Gess

(57) ABSTRACT

The present invention relates to novel indanyl urea derivatives of formula (I):

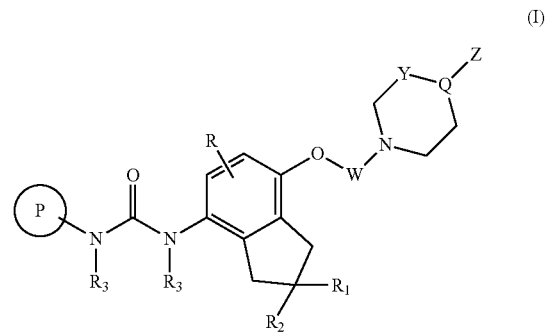

(I)

their pharmaceutically acceptable salts, and their isomers, steroisomers, atropisomers, conformers, tautomers, polymorphs, hydrates and solvates. The present invention also encompasses process for preparing novel compounds and pharmaceutical composition of said compounds. The invention further relates to the use of the compounds for the preparation of medicament for use as pharmaceuticals.

10 Claims, 2 Drawing Sheets

UREA-SUBSTITUTED INDANES AS P38 MAP KINASE INHIBITORS

RELATED APPLICATIONS

The present application is a U.S. National Stage Application filed under 35 U.S.C. § 371, from PCT/IB2015/056505 filed on 27 Aug. 2015, which claims the benefit of Indian Provisional Patent Application No. 2772/MUM/2014 filed on 29 Aug. 2014.

FIELD OF THE INVENTION

The present invention relates to novel indanyl urea derivatives, their pharmaceutically acceptable salts, and their isomers, steroisomers, atropisomers, conformers, tautomers, polymorphs, hydrates and solvates. The present invention also encompasses process for preparing novel compounds and pharmaceutical composition of said compounds. The invention further relates to the use of the above mentioned compounds for the preparation of medicament for use as pharmaceuticals.

BACKGROUND OF THE INVENTION

The prevalence of airway diseases has increased in recent decades despite therapeutic advances. Among the airway diseases, asthma exacerbations and chronic obstructive pulmonary disease (COPD) are major causes of hospitalization. Both asthma and COPD involve chronic inflammation of the respiratory tract. Despite the presentation of similar symptoms, such as dyspnea, coughing, wheezing and expectoration, these airway diseases have different underlying pathophysiological processes. COPD is a term which refers to a large group of lung diseases characterized by obstruction of air flow that interferes with normal breathing. Emphysema and chronic bronchitis are the most important conditions that compose COPD. (Australian lung foundation, 2006). COPD involves chronic inflammation of the peripheral airways and lung parenchyma, which leads to progressive narrowing of the airways and shortness of breath. On the other hand Asthma is characterized by episodic airway obstruction symptoms and usually starts early in life. The inflammation differs markedly between asthma and COPD, with different cells, mediators, consequences and there is a difference in response to corticosteroids (Clinics (Sao Paulo). 2012; 67(11):1335-43). However, more recently it has become clear that severe asthma is much more similar to COPD, with similarities in the inflammation and sharing a poor response to corticosteroids (*J Allergy Clin Immunol.* 2013; 131(3):636-45). Interestingly, studies of molecular genetics are now showing that severe asthma and COPD share several gene polymorphisms (*Comp Funct Genomics.* 2012; 2012: 968267).

Chronic obstructive pulmonary disease (COPD) is a major global health problem that is becoming prevalent, particularly in developing countries. It is one of the most common diseases in the world, with a lifetime risk estimated to be as high as 25%, and now equally affects both men and women (*Nature Reviews* 2013; 12: 543-559).

Current forms of therapy for COPD are relatively ineffective, as there are no drugs available that considerably reduce disease progression or mortality or have a substantial effect on exacerbations, which are one of the most common causes of hospital admissions.

Long acting bronchodilators are the mainstay of current COPD therapy. There have been several advances in the development of β2-adrenergic receptor agonists and muscarinic receptor antagonists that only need to be administered once a day. Moreover, long acting β2-adrenergic receptor agonists (LABAs) and long-acting muscarinic acetylcholine receptor antagonists (LAMAs) have additive effects on bronchodilation and in the improvement of symptoms, which has led to the development of LABA-LAMA combination inhalers. However, although these drugs produce effective bronchodilation, they fail to treat the underlying inflammatory disease in patients with COPD.

Alternatively or additional to bronchodilators, oral or inhaled corticosteroids could also be used as COPD therapy. But corticosteroids have limitations as long term oral corticosteroid therapy is not recommended and inhaled corticosteroids are known to be associated with increased risk of pneumonia in patients. (www.bcguidelines.ca) Moreover, inhaled corticosteroids are found largely ineffective in significant number of COPD patients as an anti-inflammatory therapy in COPD (*Ann Farn Med.* 2006; 4(3):253-62). Recently, PDE-4 inhibitors have also been approved for treatment of severe COPD in adults; however, such PDE-4 inhibitors have shown dose limiting side effects (*International Journal of COPD* 2007; 2(2): 121-129).

With better understanding of the pathophysiology of COPD disease process and recognition of inflammation as an important feature, it is anticipated that disease modifying therapy for COPD targeting underlying inflammation will prove effective the way it has been successful in the treatment of other chronic inflammatory conditions like RA.

Many kinases are involved in the regulation of proinflammatory transcription factors and inflammatory genes. The mitogen-activated protein kinase (MAPK) family includes the p38 kinases, which consists of highly conserved proline-directed serine-threonine protein kinases that are activated in response to inflammatory signals. The p38 MAPK pathway, which is activated by cellular stress, regulates the expression of many inflammatory genes that are involved in COPD (*Nature Reviews* 2013; 12: 543-559). Proinflammatory cytokines/chemokines and environmental stress activates p38 mitogen activated protein kinase (MAPK) by phosphorylation, which in turn activates p38 MAPK signaling pathway. p38 is involved in the inflammatory responses induced by different stimuli through activation and release of proinflammatory cytokines/chemokines, posttranslational regulation of these genes, and activation of inflammatory cell migration. Therefore, p38 inhibitors present a potentially attractive treatment target for the chronic inflammatory conditions including COPD. Of the four isoforms known so far, p38 alpha is the most abundant in inflammatory cells and has been the most studied.

Over the past two decades, p38 MAPK has been the subject of intense multidisciplinary research. p38 MAPK inhibitors have been shown to be efficacious in several disease models, including rheumatoid arthritis, psoriasis, Crohn's disease, and stroke. Recent studies support a role for p38 MAPK in the development, maintenance, and/or exacerbation of a number of pulmonary diseases, such as asthma, cystic fibrosis, idiopathic pulmonary fibrosis, and chronic obstructive pulmonary disease. There is now an abundant literature which demonstrates that p38 MAPK is activated in chronic inflammatory conditions and that its activation results in the elaboration and release of further proinflammatory cytokines (*Expert Opin. Investig. Drugs* 2008; 17(10):1411-1425).

Though orally administered small molecule inhibitors targeted to p38 MAPK have proved to be effective in reducing various parameters of inflammation in cells and tissues obtained from patients with COPD in initial clinical studies, the major obstacle hindering the definition and exploitation of the potential utilities of p38 MAPK inhibitors in the treatment of human chronic inflammatory diseases has been the toxicity observed in patients. This has been sufficiently severe to result in the withdrawal from clinical development of many of the compounds progressed. Presently, none of them is yet approved anywhere in the world because of one or the other problems associated with selected molecules such as toxicity or selectivity (*Expert Opin. Investig. Drugs* 2008; 17(10):1411-1425 & *Chest* 2011; 139(6):1470-1479).

To overcome these problems of toxicity and selectivity of the target associated with known p38 MAPK inhibitors, some alternative strategies were designed. One of them was to design the treatment approaches wherein p38 kinase inhibitor is dosed directly to the inflamed organ.

Other strategies include developing newer generation p38 MAPK inhibitors with improved selectivity and lesser side effect profile.

There remains a need to identify and develop new p38 MAPK inhibitors which provides desired therapeutic potential along with improved pharmacokinetic profile and/or lesser side effects.

WO1998057937 discloses benzene derivatives as inhibitor of factor Xa with a neutral P1 specificity group.

WO200043384 discloses aromatic heterocyclic compounds for treating conditions involving inflammatory diseases. Disclosed compounds said to inhibit the release of inflammatory cytokines such as IL-1 and TNF.

WO2003072569 discloses 1,4-disubstituted benzofused cycloalkyl urea compounds in treating cytokine mediated disease.

US20080300281 discloses aryl and heteroaryl substituted heterocyclic ureas as p38 kinase inhibitor for the treatment of inflammatory or immunomodulatory diseases. Similarly, WO2008125014 also discloses urea derivatives as p38 kinase inhibitor.

Present invention provides novel indanyl urea derivatives as p38 MAPK inhibitors, which have demonstrated desired efficacy and safety profile.

SUMMARY OF THE INVENTION

In one embodiment, the present invention provides novel compounds of formula (I),

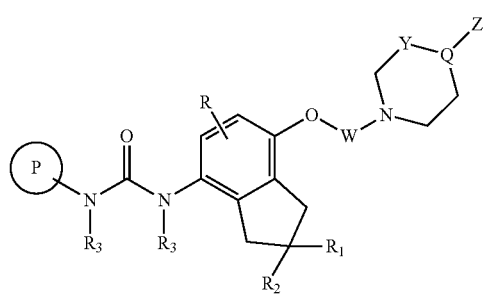

(I)

their pharmaceutically acceptable salts and their isomers, stereoisomers, atropisomers, conformers, tautomers, polymorphs, hydrates, and solvates;
wherein:
Y is C=O or C(Z');
Q is C or N, when Y is C=O then Q is N;

when Y is C=O, Z is selected from hydrogen, —($C_1$-$C_6$)alkyl, branched-($C_3$-$C_6$)alkyl, —($C_3$-$C_6$)cycloalkyl, —($C_1$-$C_3$)alkyl($C_3$-$C_6$)cycloalkyl, —($C_1$-$C_6$)alkyl-OH, —($C_1$-$C_6$)alkyl-SH, —C(O)$CH_2R_4$, —($C_1$-$C_6$)alkyl-$NR_5R_6$, —($C_1$-$C_6$)alkyl-aryl, —($C_1$-$C_6$)alkyl-heteroaryl, —($C_1$-$C_6$)alkyl-$CO_2H$, —($C_1$-$C_6$)alkyl-$CO_2R_7$, —($C_1$-$C_6$)alkyl-C(O)$NR_5R_6$, —C(O)$NR_5R_6$, —$CO_2R_7$, —$COR_7$, —($C_1$-$C_6$)alkyl-$OR_7$, —($C_1$-$C_6$)alkyl-S(O)$_n$$R_7$, —S(O)$_m$—$R_7$, —S(O)$_m$N($R_3$)—$R_7$, —S(O)$_m$$NR_5R_6$, aryl and heteroaryl, wherein said aryl or heteroaryl may be further optionally substituted by 1-3 substituents independently selected from $R_8$;
or when Y is C(Z'), Z and Z' together forms a 5 or 6 membered aromatic ring system having 1 to 3 heteroatoms independently selected from O, S(O)$_n$ or N and said ring is optionally substituted by 1-3 substituents independently selected from $R_8$;
P is a cyclic ring, which is selected from

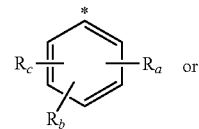

(A)

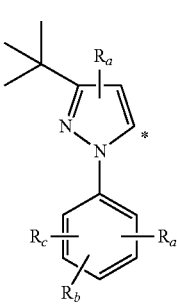

(B)

where * denotes the point of attachment to the urea nitrogen in formula (I):
$R_a$, $R_b$, and $R_c$ are independently selected from hydrogen, halogen, —($C_1$-$C_6$)alkyl, branched-($C_3$-$C_6$)alkyl, —($C_3$-$C_6$)cycloalkyl, aryl, heteroaryl, heterocyclyl, —($C_1$-$C_6$)alkyl-aryl, —($C_1$-$C_6$)alkyl-heteroaryl, hydroxy, —$CF_3$, —$OCF_3$, —$NO_2$, —C(O)—($C_1$-$C_6$)alkyl, —C(O)—($C_3$-$C_6$)cycloalkyl, —C(O)$CH_2R_4$, —$NR_5R_6$, —N($R_3$)C(O)—$R_7$, —N($R_3$)S(O)$_m$—$R_7$, —N($R_3$)C(O)—N($R_3$)—$R_7$, —N($R_3$)C(S)N($R_3$)—$R_7$, —$OR_7$, —$CO_2H$, —$CO_2R_7$, —C(O)—$NR_5R_6$, —SH, —S(O)$_n$$R_7$, —S(O)$_m$N($R_3$)—$R_7$, —S(O)$_m$—$NR_5R_6$, —CN, —CHO, —($C_1$-$C_6$)alkyl-$R_4$ and —($C_1$-$C_6$)alkyl-$NR_5R_6$, wherein each aryl, heterocyclyl, or heteroaryl may be further optionally substituted with 1-3 substituents independently selected from halogen, —($C_1$-$C_6$)alkyl, branched-($C_3$-$C_6$)alkyl, aryl, heteroaryl, heterocyclyl, hydroxy, —$CF_3$, —$OCF_3$, —$OR_7$, —O—($C_1$-$C_6$)alkyl-$R_8$, —$NO_2$, —C(O)—($C_1$-$C_6$)alkyl, —C(O)$CH_2R_4$, —$NR_5R_6$, —$CO_2H$, —$CO_2R_7$, —C(O)$NR_5R_6$, —N($R_3$)C(O)—$R_7$, —N($R_3$)S(O)$_m$—$R_7$, —SH, —S(O)$_n$—$R_7$, —S(O)$_m$N($R_3$)—$R_7$, —CN, —CHO, —($C_1$-$C_6$)alkyl-$OR_7$, —($C_1$-$C_6$)alkyl-halogen and —($C_1$-$C_6$)alkyl-$NR_5R_6$; or any two substituents of $R_a$, $R_b$, and $R_c$ may form a saturated, partially saturated or unsaturated monocyclic ring, which may contain 0, 1, 2 or 3 ring heteroatoms selected from O, S(O)$_n$ or N;
W is —($CH_2$)$_p$, —($CH_2$)$_m$CO or —($CH_2$)$_m$S(O)$_m$;
R is selected from hydrogen, —($C_1$-$C_6$)alkyl, branched-($C_3$-$C_6$)alkyl, halogen, —O($C_1$-$C_6$)alkyl, —$CF_3$, —$OCF_3$ and hydroxy;

$R_1$ and $R_2$ are independently selected from hydrogen, hydroxy, —$(C_1-C_3)$alkyl, branched-$(C_3-C_6)$alkyl and —$(C_3-C_6)$cycloalkyl or $R_1$ and $R_2$ together with the carbon to which they are attached, forms a —$(C_3-C_6)$cycloalkyl ring in a spiro manner;

$R_3$ is independently selected from hydrogen, —$(C_1-C_3)$ alkyl, branched-$(C_3-C_6)$alkyl, —$(C_1-C_3)$ alkyl$(C_3-C_6)$ cycloalkyl, and glucuronate;

$R_4$ is independently selected from hydroxy, —SH, —$OR_7$, —$NR_5R_6$, —$S(O)_n$—$R_7$, —$S(O)_n$—$(C_1-C_6)$alkyl-$CO_2(C_1-C_6)$alkyl, —$S(O)_n$—$(C_1-C_6)$alkyl-OH, —$S(O)_n$—$(C_1-C_6)$ alkyl-$CO_2H$, —$N(R_3)C(O)$—$R_7$, —$N(R_3)S(O)_m$—$R_7$, —O—$(C_1-C_6)$alkyl-$CO_2(C_1-C_6)$alkyl, —O—$(C_1-C_6)$alkyl-OH and —O—$(C_1-C_6)$alkyl-$CO_2H$;

$R_5$ and $R_6$ are independently selected from hydrogen, —$(C_1-C_6)$alkyl, branched-$(C_3-C_6)$alkyl, —$COR_7$, —$C(O)NR_5R_6$, —$S(O)_mR_7$, —$(C_1-C_6)$alkyl-$(C_3-C_6)$cycloalkyl, —$(C_3-C_6)$ cycloalkyl, aryl and heteroaryl or $R_5$ and $R_6$ are taken together with nitrogen to form a 3 to 8 membered monocyclic or 8 to 12 membered bicyclic heterocycle ring, wherein said monocyclic or bicyclic ring contains 0, 1, 2 or 3 ring heteroatoms selected from O, $S(O)_n$ or N and said monocyclic or bicyclic ring is optionally substituted by 1-3 substituents independently selected from $R_8$;

$R_7$ is independently selected from —$(C_1-C_6)$alkyl, —$(C_1-C_6)$alkyl-OH, branched-$(C_3-C_6)$alkyl, —$(C_3-C_6)$cycloalkyl, —$(C_1-C_6)$alkyl-$(C_3-C_6)$cycloalkyl, aryl and heteroaryl; $R_8$ is independently selected from hydrogen, halogen, hydroxy, —CN, —CHO, —$NO_2$, —$(C_1-C_6)$alkyl, —$(C_3-C_6)$cycloalkyl, —$(C_1-C_6)$alkyl-$(C_3-C_6)$cycloalkyl, aryl, heteroaryl, heterocyclyl, —$C(O)CH_2R_4$, —$OR_7$, —SH, —$S(O)_n$—$R_7$, —$CF_3$, —$OCF_3$, —$CO_2H$, —$COR_7$, —$CO_2R_7$, —$C(O)NR_5R_6$, —$S(O)_mN(R_3)$—$R_7$ and —$NR_5R_6$, wherein the said $(C_1-C_6)$alkyl, aryl, heterocyclyl and heteroaryl may be further substituted with 1-3 substituents independently selected from $R_9$.

$R_9$ is independently selected from $R_7$, halogen, hydroxy, —$(C_1-C_6)$alkyl-OH, —$NO_2$, —SH, —$OR_7$, —$O(C_1-C_6)$ alkyl-$R_4$, —OC(O)—$R_7$, —$O(C_1-C_6)$alkyl-$CO_2R_7$, —$O(C_1-C_6)$alkyl-$CO_2H$, —$O(C_1-C_6)$alkyl-C(O)—$NR_5R_6$, —$OS(O)_m$—$R_7$, —$CO_2R_7$, —$CO_2H$, —C(O)—$R_7$, —C(O)—$NR_5R_6$, —$S(O)_n$—$R_7$, —$S(O)_n(C_1-C_6)$alkyl-$R_4$, —$S(O)_n(C_1-C_6)$alkyl-$C(O)NR_5R_6$, —$S(O)_n(C_1-C_6)$alkyl-$CO_2R_7$, —$S(O)_n(C_1-C_6)$alkyl-$CO_2H$, —$NR_5R_6$, —$S(O)_m$—$NR_5R_6$, —$N(R_3)C(O)$—$R_7$, —$N(R_3)C(O)N(R_3)$—$R_7$, —$N(R_3)C(S)N(R_3)$—$R_7$, —$N(R_3)C(O)(C_1-C_6)$alkyl-aryl, —$N(R_3)S(O)_m$—$R_7$, $OSO_3H$ and O-glucuronate;

m is 1 or 2;
n is 0, 1 or 2; and
t is 2 or 3.

In another embodiment, the present invention pertains to a compound as above, however only including pharmaceutically acceptable salts thereof.

In another embodiment, the present invention provides a method for preparation of a compound of formula (I) as herein described in Schemes 1 to 3.

In another embodiment, the present invention includes synthetic intermediates that are useful in preparing the compounds of formula (I) and process for preparing such intermediates.

In another embodiment, the present invention is a pharmaceutical composition comprising a compound of formula (I), optionally in admixture with a pharmaceutically acceptable adjuvant or carrier.

Another embodiment of the present invention is a method for treating allergic and non-allergic airway diseases by administering a therapeutically effective amount of a compound of formula (I) to a mammal, including human being, in need thereof.

Another embodiment of the present invention is a method for treating chronic obstructive pulmonary disease and asthma by administering a therapeutically effective amount of a compound of formula (I) to a mammal, including human being, in need thereof.

Another embodiment of the present invention is the use of a compound of formula (I) for the preparation of a medicament for treating allergic and non-allergic airway diseases.

Another embodiment of the present invention is the use of a compound of formula (I) for the preparation of a medicament for treating chronic obstructive pulmonary disease and asthma.

DETAILED DESCRIPTION OF THE INVENTION

Figure 1A:
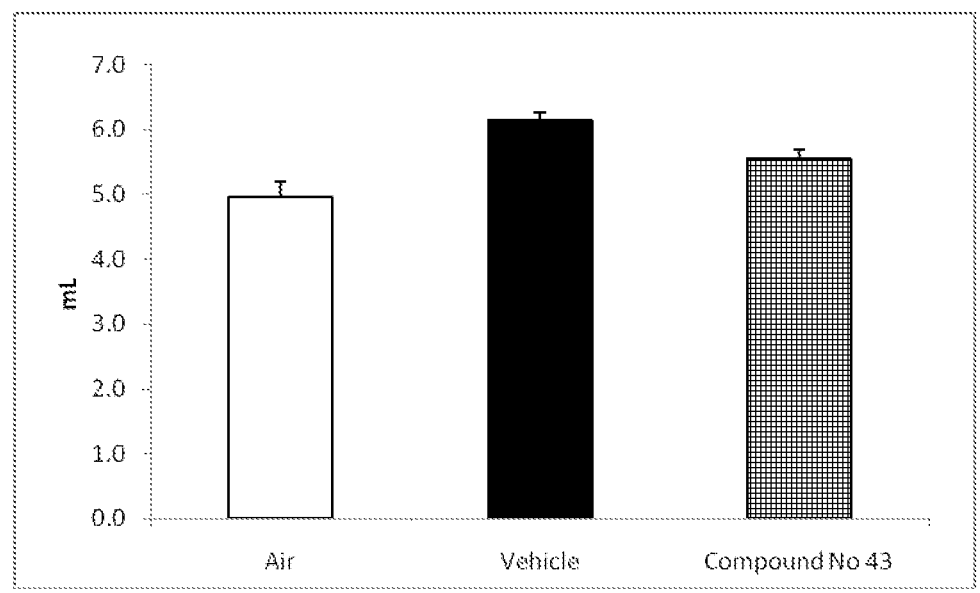
FIG. 1A illustrates the effect of treatment of compound no. 43 on the lung function parameter of functional residual capacity.

In one embodiment, the present invention provides novel compounds of formula (I),

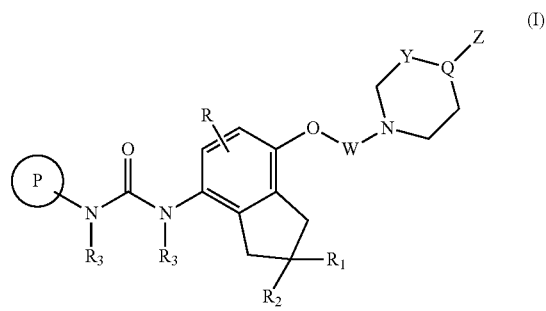

their pharmaceutically acceptable salts and their isomers, stereoisomers, atropisomers, conformers, tautomers, polymorphs, hydrates and solvates, wherein R, $R_1$, $R_2$, $R_3$, P, W, Q, Y and Z, are as defined above.

In a preferred embodiment, the present invention provides novel compounds of formula (I),

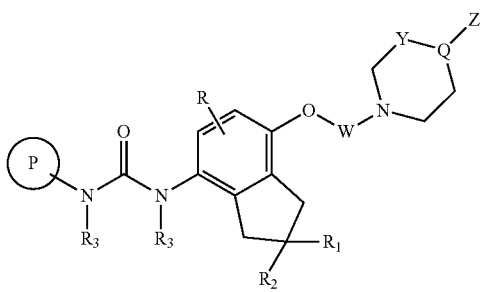

their pharmaceutically acceptable salts and their isomers, stereoisomers, atropisomers, conformers, tautomers, polymorphs, hydrates and solvates;
wherein:
Y is C=O or C(Z');
Q is C or N; when Y is C=O then Q is N;
when Y is C=O, Z is selected from hydrogen, —($C_1$-$C_6$) alkyl, branched-($C_3$-$C_6$)alkyl, —($C_3$-$C_6$)cycloalkyl, —($C_1$-$C_3$)alkyl($C_3$-$C_6$)cycloalkyl, —($C_1$-$C_6$)alkyl-OH, —($C_1$-$C_6$) alkyl-aryl, —($C_1$-$C_6$)alkyl-C(O)$NR_5R_6$, S(O)$_m$—$R_7$ and aryl;
or when Y is C(Z'), Z and Z' together forms a 5 or 6 membered aromatic ring system having 1 to 3 heteroatoms independently selected from S(O)$_n$ or N and said ring is optionally substituted by 1-2 substituents independently selected from $R_8$;
P is a cyclic ring, which is selected from

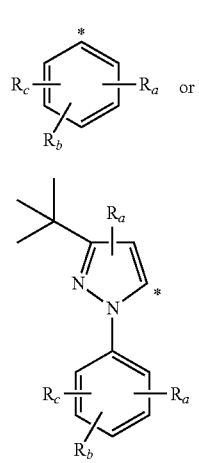

where * denotes the point of attachment to the urea nitrogen in formula (I):

$R_a$, $R_b$, and $R_c$ are independently selected from hydrogen, halogen, —($C_1$-$C_6$)alkyl, branched-($C_3$-$C_6$)alkyl, —($C_3$-$C_6$) cycloalkyl, hydroxy, —N($R_3$)S(O)$_m$—$R_7$, —N($R_3$)COR$_7$ and —OR$_7$;
W is —(CH$_2$)$_t$ or —(CH$_2$)$_m$CO;
R is hydrogen or —($C_1$-$C_6$)alkyl;
$R_1$ and $R_2$ are independently selected from hydrogen and hydroxy;
$R_3$ is independently selected from hydrogen and glucuronate;
$R_4$ is selected from hydroxy and —$NR_5R_6$;
$R_5$ and $R_6$ are independently selected from hydrogen, —($C_1$-$C_6$)alkyl and —COR$_7$; or
$R_5$ and $R_6$ are taken together with nitrogen to form a 3 to 8 membered monocyclic heterocycle ring, wherein said monocyclic ring contains 0, 1, 2 or 3 ring heteroatoms selected from O or N;
$R_7$ is selected from —($C_1$-$C_6$)alkyl, —($C_3$-$C_6$)cycloalkyl, —($C_1$-$C_6$)alkyl-OH and branched-($C_3$-$C_6$)alkyl;
$R_8$ is independently selected from hydrogen, —($C_3$-$C_6$) cycloalkyl, aryl, heteroaryl, —CF$_3$, —CO$_2R_7$ and —$NR_5R_6$, wherein said aryl or heteroaryl may be further substituted with 1-3 substituents selected from $R_9$;
$R_9$ is independently selected from halogen, $R_7$, hydroxy, —OR$_7$, —O($C_1$-$C_6$)alkyl-$R_4$, —S(O)$_n$—$R_7$, —S(O)$_n$($C_1$-$C_6$)alkyl-$R_4$, —($C_1$-$C_6$)alkyl-OH and O-glucuronate;
m is 1 or 2;
n is 0; and
t is 2 or 3.

In a most preferred embodiment, the present invention provides novel compounds of formula (I),

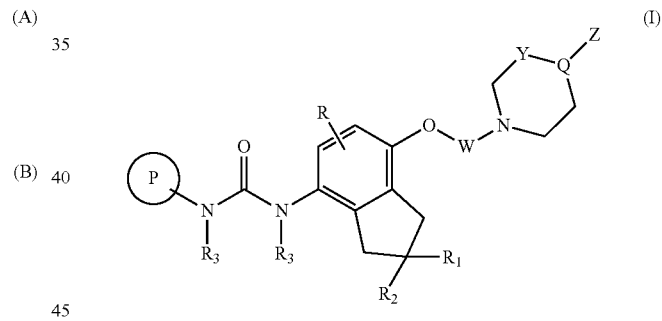

their pharmaceutically acceptable salts and their isomers, stereoisomers, atropisomers, conformers, tautomers, polymorphs, hydrates and solvates;
wherein Q=N and R, $R_1$, $R_2$, $R_3$, P, W, Y and Z, are as defined above, A family of specific compounds of particular interest within the above formula (I) consists of compound and pharmaceutically acceptable salts thereof as follows:

| Compd. No. | Chemical Name |
|---|---|
| 1 | 1-[3-tert-butyl-1-(4-methylphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea |
| 2 | 1-[3-tert-butyl-1-(4-tert-butylphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea |
| 3 | 1-[3-tert-butyl-1-(4-cyclohexylphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea |

| Compd. No. | Chemical Name |
|---|---|
| 4 | 1-(3-tert-butyl-1-phenyl-1H-pyrazol-5-yl)-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea |
| 5 | 1-(3-tert-butyl-1-phenyl-1H-pyrazol-5-yl)-3-(7-{2-[3-(2-methoxyphenyl)-5,6-dihydro[1,2,4]triazolo[4,3-a]pyrazin-7(8H)-yl]-2-oxoethoxy}-2,3-dihydro-1H-inden-4-yl)urea |
| 6 | 1-[3-tert-butyl-1-(4-methylphenyl)-1H-pyrazol-5-yl]-3-(7-{2-[4-(2-hydroxyethyl)-3-oxopiperazin-1-yl]ethoxy}-2,3-dihydro-1H-inden-4-yl)urea |
| 7 | 1-(3-tert-butyl-1-phenyl-1H-pyrazol-5-yl)-3-[7-(2-{3-[2-(methylsulfanyl)phenyl]-5,6-dihydro[1,2,4]triazolo[4,3-a]pyrazin-7(8H)-yl}-2-oxoethoxy)-2,3-dihydro-1H-inden-4-yl]urea |
| 8 | 1-[3-tert-butyl-1-(3-chloro-4-hydroxyphenyl)-1H-pyrazol-5-yl]-3-(7-{2-[3-(2-methoxyphenyl)-5,6-dihydro[1,2,4]triazolo[4,3-a]pyrazin-7(8H)-yl]-2-oxoethoxy}-2,3-dihydro-1H-inden-4-yl)urea |
| 9 | 1-[3-tert-butyl-1-(3-chloro-4-hydroxyphenyl)-1H-pyrazol-5-yl]-3-[7-(2-{3-[2-(methylsulfanyl)phenyl]-5,6-dihydro[1,2,4]triazolo[4,3-a]pyrazin-7(8H)-yl}-2-oxoethoxy)-2,3-dihydro-1H-inden-4-yl]urea |
| 10 | 1-[3-tert-butyl-1-(4-methylphenyl)-1H-pyrazol-5-yl]-3-[7-(2-{3-[2-(methylsulfanyl)phenyl]-5,6-dihydro[1,2,4]triazolo[4,3-a]pyrazin-7(8H)-yl]-2-oxoethoxy)-2,3-dihydro-1H-inden-4-yl]urea |
| 11 | 1-(3-tert-butyl-1-phenyl-1H-pyrazol-5-yl)-3-(7-(2-[3-(2-{[2(morpholin-4-yl)ethyl]sulfanyl}phenyl)-5,6-dihydro[1,2,4]triazolo[4,3-a]pyrazin-7(8H)-yl]-2-oxoethoxy)-2,3-dihydro-1H-inden-4-yl)urea |
| 12 | 1-[3-tert-butyl-1-(4-methylphenyl)-1H-pyrazol-5-yl]-3-(7-{2-[4-(cyclopropylmethyl)-3-oxopiperazin-1-yl]ethoxy}-2,3-dihydro-1H-inden-4-yl)urea |
| 13 | 1-[3-tert-butyl-1-(4-methylphenyl)-1H-pyrazol-5-yl]-3-[7-(2-{3-[2-(methylsulfanyl)phenyl]-5,6-dihydro[1,2,4]triazolo[4,3-a]pyrazin-7(8H)-yl}ethoxy)-2,3-dihydro-1H-inden-4-yl]urea |
| 14 | 1-[3-tert-butyl-1-(4-methylphenyl)-1H-pyrazol-5-yl]-3-(7-{2-[3-(2-methoxyphenyl)-5,6-dihydro[1,2,4]triazolo[4,3-a]pyrazin-7(8H)-yl]ethoxy}-2,3-dihydro-1H-inden-4-yl)urea |
| 15 | 1-[3-tert-butyl-1-(4-methylphenyl)-1H-pyrazol-5-yl]-3-(7-{2-[3-(2-hydroxyphenyl)-5,6-dihydro[1,2,4]triazolo[4,3-a]pyrazin-7(8H)-yl]ethoxy}-2,3-dihydro-1H-inden-4-yl)urea |
| 16 | 1-{7-[2-(4-benzyl-3-oxopiperazin-1-yl)ethoxy]-2,3-dihydro-1H-inden-4-yl}-3-[3-tert-butyl-1-(4-methylphenyl)-1H-pyrazol-5-yl]urea |
| 17 | 1-[3-tert-butyl-1-(4-methoxyphenyl)-1H-pyrazol-5-yl]-3-(7-{2-[4-(cyclopropylmethyl)-3-oxopiperazin-1-yl]ethoxy}-2,3-dihydro-1H-inden-4-yl)urea |
| 18 | 1-[3-tert-butyl-1-(4-hydroxyphenyl)-1H-pyrazol-5-yl]-3-(7-{2-[4-(cyclopropylmethyl)-3-oxopiperazin-1-yl]ethoxy}-2,3-dihydro-1H-inden-4-yl)urea |
| 19 | 1-[3-tert-butyl-1-(4-methylphenyl)-1H-pyrazol-5-yl]-3-{7-[2-(3-oxo-4-phenylpiperazin-1-yl)ethoxy]-2,3-dihydro-1H-inden-4-yl}urea |
| 20 | 1-[3-tert-butyl-1-(4-methylphenyl)-1H-pyrazol-5-yl]-3-(7-{2-[3-{2-[2-(morpholin-4-yl)ethoxy]phenyl}-5,6-dihydro[1,2,4]triazolo[4,3-a]pyrazin-7(8H)-yl]ethoxy}-2,3-dihydro-1H-inden-4-yl)urea |
| 21 | 1-[3-tert-butyl-1-(4-methylphenyl)-1H-pyrazol-5-yl]-3-(7-{2-[4-(cyclopentylmethyl)-3-oxopiperazin-1-yl]ethoxy}-2,3-dihydro-1H-inden-4-yl)urea |
| 22 | 1-[3-tert-butyl-1-(4-methylphenyl)-1H-pyrazol-5-yl]-3-(7-{2-[4-(cyclobutylmethyl)-3-oxopiperazin-1-yl]ethoxy}-2,3-dihydro-1H-inden-4-yl)urea |
| 23 | 1-[3-tert-butyl-1-(4-ethylphenyl)-1H-pyrazol-5-yl]-3-(7-{2-[3-(2-methoxyphenyl)-5,6-dihydro[1,2,4]triazolo[4,3-a]pyrazin-7(8H)-yl]ethoxy}-2,3-dihydro-1H-inden-4-yl)urea |
| 24 | 1-[3-tert-butyl-1-(3-chloro-4-hydroxyphenyl)-1H-pyrazol-5-yl]-3-[7-(2-{3-[2-(methylsulfanyl)phenyl]-5,6-dihydro[1,2,4]triazolo[4,3-a]pyrazin-7(8H)-yl}ethoxy)-2,3-dihydro-1H-inden-4-yl]urea |
| 25 | 1-[3-tert-buty1-1-(3-chloro-4-hydroxyphenyl)-1H-pyrazol-5-yl]-3-(7-{2-[3-(2-methoxyphenyl)-5,6-dihydro[1,2,4]triazolo[4,3-a]pyrazin-7(8H)-yl]ethoxy}-2,3-dihydro-1H-inden-4-yl)urea |
| 26 | 1-[3-tert-butyl-1-(3-chloro-4-hydroxyphenyl)-1H-pyrazol-5-yl]-3-(7-{2-[3-(2-hydroxyphenyl)-5,6-dihydro[1,2,4]triazolo[4,3-a]pyrazin-7(8H)-yl]ethoxy}-2,3-dihydro-1H-inden-4-yl)urea |
| 27 | 1-[3-tert-butyl-1-(3-chloro-4-hydroxyphenyl)-1H-pyrazol-5-yl]-3-(7-{2-[3-(2-propoxyphenyl)-5,6-dihydro[1,2,4]triazolo[4,3-a]pyrazin-7(8H)-yl]ethoxy}-2,3-dihydro-1H-inden-4-yl)urea |
| 28 | 1-[3-tert-butyl-1-(4-methylphenyl)-1H-pyrazol-5-yl]-3-(7-{3-[4-(cyclopropylmethyl)-3-oxopiperazin-1-yl]propoxy}-2,3-dihydro-1H-inden-4-yl)urea |
| 29 | 1-[3-tert-butyl-1-(4-methylphenyl)-1H-pyrazol-5-yl]-3-(7-{2-[3-(3-chloro-2-hydroxyphenyl)-5,6-dihydro[1,2,4]triazolo[4,3-a]pyrazin-7(8H)-yl]ethoxy}-2,3-dihydro-1H-inden-4-yl)urea |

-continued

| Compd. No. | Chemical Name |
|---|---|
| 30 | 1-[3-tert-butyl-1-(4-methylphenyl)-1H-pyrazol-5-yl]-3-[7-(2-{3-[2-(2-hydroxyethoxy)phenyl]-5,6-dihydro[1,2,4]triazolo[4,3-a]pyrazin-7(8H)-yl}ethoxy)-2,3-dihydro-1H-inden-4-yl]urea |
| 31 | 1-[3-tert-butyl-1-(4-methylphenyl)-1H-pyrazol-5-yl]-3-(7-{2-[3-(3-chloro-4-hydroxyphenyl)-5,6-dihydro[1,2,4]triazolo[4,3-a]pyrazin-7(8H)-yl]ethoxy}-2,3-dihydro-1H-inden-4-yl)urea |
| 32 | 1-(7-{2-[3-(2-butoxyphenyl)-5,6-dihydro[1,2,4]triazolo[4,3-a]pyrazin-7(8H)-yl]ethoxy}-2,3-dihydro-1H-inden-4-yl)-3-[3-tert-butyl-1-(4-methylphenyl)-1H-pyrazol-5-yl]urea |
| 33 | 1-[3-tert-butyl-1-(4-methylphenyl)-1H-pyrazol-5-yl]-3-[7-(2-{3-[2-(propylsulfanyl)phenyl]-5,6-dihydro[1,2,4]triazolo[4,3-a]pyrazin-7(8H)-yl}ethoxy)-2,3-dihydro-1H-inden-4-yl]urea |
| 34 | 1-[3-tert-butyl-1-(4-methylphenyl)-1H-pyrazol-5-yl]-3-(7-{2-[3-(4-hydroxyphenyl)-5,6-dihydro[1,2,4]triazolo[4,3-a]pyrazin-7(8H)-yl]ethoxy}-2,3-dihydro-1H-inden-4-yl)urea |
| 35 | 1-[3-tert-butyl-1-(3-chloro-4-hydroxyphenyl)-1H-pyrazol-5-yl]-3-[7-(2-{3-[2-(propylsulfanyl)phenyl]-5,6-dihydro[1,2,4]triazolo[4,3-a]pyrazin-7(8H)-yl}ethoxy)-2,3-dihydro-1H-inden-4-yl]urea |
| 36 | 1-[3-tert-butyl-1-(4-methylphenyl)-1H-pyrazol-5-yl]-3-(7-{2-[3-(3-hydroxyphenyl)-5,6-dihydro[1,2,4]triazolo[4,3-a]pyrazin-7(8H)-yl]ethoxy}-2,3-dihydro-1H-inden-4-yl)urea |
| 37 | 1-[3-tert-butyl-1-(4-methylphenyl)-1H-pyrazol-5-yl]-3-(7-{2-[3-(2,4-dihydroxyphenyl)-5,6-dihydro[1,2,4]triazolo[4,3-a]pyrazin-7(8H)-yl]ethoxy}-2,3-dihydro-1H-inden-4-yl)urea |
| 38 | 1-[3-tert-butyl-1-(4-methylphenyl)-1H-pyrazol-4-yl]-3-(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)urea |
| 39 | N-(5-tert-butyl-3-{[(7-{2-[4-(cyclopropylmethyl)-3-oxopiperazin-1-yl]ethoxy}-2,3-dihydro-1H-inden-4-yl)carbamoyl]amino}-2-methoxyphenyl)methanesulfonamide |
| 40 | N-(5-tert-butyl-3-{[(7-{2-[3-(2-hydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)methanesulfonamide |
| 41 | N-(5-tert-butyl-3-{[(7-{3-[4-(cyclopropylmethyl)-3-oxopiperazin-1-yl]propoxy}-2,3-dihydro-1H-inden-4-yl)carbamoyl]amino}-2-methoxyphenyl) methanesulfonamide |
| 42 | N-[5-tert-butyl-2-methoxy-3-({[7-(2-{3-[2-(propylsulfanyl)phenyl]-5,6-dihydro[1,2,4]triazolo[4,3-a]pyrazin-7(8H)-yl}ethoxy)-2,3-dihydro-1H-inden-4-yl]carbamoyl}amino)phenyl]methanesulfonamide |
| 43 | N-(5-tert-butyl-3-{[(7-{2-[4-(cyclopropylmethyl)-3-oxopiperazin-1-yl]ethoxy}-2,3-dihydro-1H-inden-4-yl)carbamoyl]amino}-2-methoxyphenyl)ethanesulfonamide |
| 44 | N-{5-tert-butyl-3-[({7-[2-(4-butyl-3-oxopiperazin-1-yl)ethoxy]-2,3-dihydro-1H-inden-4-yl}carbamoyl)amino]-2-methoxyphenyl} methanesulfonamide |
| 45 | N-[5-tert-butyl-2-methoxy-3-({[7-(2-{3-[2-(methylsulfanyl)phenyl]-5,6-dihydro[1,2,4]triazolo[4,3-a]pyrazin-7(8H)-yl}ethoxy)-2,3-dihydro-1H-inden-4-yl]carbamoyl}amino)phenyl]ethanesulfonamide |
| 46 | N-(5-tert-butyl-3-{[(7-{2-[3-(3-hydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)methanesulfonamide |
| 47 | N-(5-tert-butyl-3-{[(7-{2-[3-{4-[(2-hydroxyethyl)sulfanyl]phenyl}-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)methanesulfonamide |
| 48 | N-(5-tert-butyl-3-{[(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)methanesulfonamide |
| 49 | N-(5-tert-butyl-3-{[(7-{2-[3-(2,4-dihydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)ethanesulfonamide |
| 50 | N-[5-tert-butyl-2-methoxy-3-({[7-(2-{3-[2-(propylsulfanyl)phenyl]-5,6-dihydro[1,2,4]triazolo[4,3-a]pyrazin-7(8H)-yl}ethoxy)-2,3-dihydro-lH-inden-4-yl]carbamoyl}amino)phenyl] ethanesulfonamide |
| 51 | N-(5-tert-butyl-3-{[(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)ethanesulfonamide |
| 52 | N-[5-({7-({[3-tert-butyl-1-(4-methylphenyl)-1H-pyrazol-5-yl]carbamoyl}amino)-2,3-dihydro-1H-inden-4-yl]oxy}acetyl)-4,5,6,7-tetrahydrothieno[3,2-c]pyridin-2-yl] acetamide |
| 53 | 1-[3-tert-butyl-1-(3-chloro-4-methoxyphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea |
| 54 | ethyl 6-({[7-({[3-tert-butyl-1-(4-methylphenyl)-1H-pyrazol-5-yl]carbamoyl}amino)-2,3-dihydro-1H-inden-4-yl]oxy}acetyl)-2-[(cyclopropylcarbonyl)amino]-4,5,6,7-tetrahydrothieno[2,3-c]pyridine-3-carboxylate |

| Compd. No. | Chemical Name |
|---|---|
| 55 | N-[5-({[7-({[3-tert-butyl-1-(4-cyclohexylphenyl)-1H-pyrazol-5-yl]carbamoyl}amino)-2,3-dihydro-1H-inden-4-yl]oxy}acetyl)-4,5,6,7-tetrahydrothieno[3,2-c]pyridin-2-yl]acetamide |
| 56 | 1-[3-tert-butyl-1-(3-chloro-4-methylphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea |
| 57 | 1-[3-tert-butyl-1-(4-methylphenyl)-1H-pyrazol-5-yl]-3-{7-[2-oxo-2-(3-phenyl-5,6-dihydro[1,2,4]triazolo[4,3-a]pyrazin-7(8H)-yl)ethoxy]-2,3-dihydro-1H-inden-4-yl}urea |
| 58 | 1-(3-tert-butyl-1-phenyl-1H-pyrazol-5-yl)-3-(7-{2-[3-(3-chloro-4-methoxyphenyl)-5,6-dihydro[1,2,4]triazolo[4,3-a]pyrazin-7(8H)-yl]-2-oxoethoxy}-2,3-dihydro-1H-inden-4-yl)urea |
| 59 | 1-[3-tert-butyl-1-(4-methylphenyl)-1H-pyrazol-5-yl]-3-{7-[2-(3-oxo-4-propylpiperazin-1-yl)ethoxy]-2,3-dihydro-1H-inden-4-yl}urea |
| 60 | 1-[3-tert-butyl-1-(4-fluorophenyl)-1H-pyrazol-5-yl]-3-(7-{2-[4-(cyclopropylmethyl)-3-oxopiperazin-1-yl]ethoxy}-2,3-dihydro-1H-inden-4-yl)urea |
| 61 | 1-(3-tert-butyl-1-phenyl-1H-pyrazol-5-yl)-3-(7-{2-[4-(cyclopropylmethyl)-3-oxopiperazin-1-yl]ethoxy}-2,3-dihydro-1H-inden-4-yl)urea |
| 62 | 1-[3-tert-butyl-1-(2-methylphenyl)-1H-pyrazol-5-yl]-3-(7-{2-[4-(cyclopropylmethyl)-3-oxopiperazin-1-yl]ethoxy}-2,3-dihydro-1H-inden-4-yl)urea |
| 63 | 1-[3-tert-butyl-1-(3-chloro-4-hydroxyphenyl)-1H-pyrazol-5-yl]-3-(7-{2-[3-(2,4-dihydroxyphenyl)-5,6-dihydro[1,2,4]triazolo[4,3-a]pyrazin-7(8H)-yl]ethoxy}-2,3-dihydro-1H-inden-4-yl)urea |
| 64 | N-(5-tert-butyl-3-{[(7-{2-[4-(cyclopropylmethyl)-3-oxopiperazin-1-yl]ethoxy}-2,3-dihydro-1H-inden-4-yl)carbamoyl]amino}-2-methoxyphenyl)cyclopropanecarboxamide |
| 65 | 1-[3-tert-butyl-1-(3-chloro-4-hydroxyphenyl)-1H-pyrazol-5-yl]-3-{7-[2-(3-cyclohexyl-5,6-dihydro[1,2,4]triazolo[4,3-a]pyrazin-7(8H)-yl)ethoxy]-2,3-dihydro-1H-inden-4-yl}urea |
| 66 | 1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-6-methyl-2,3-dihydro-1H-inden-4-yl)urea |
| 67 | 1-[3-tert-butyl-1-(4-methylphenyl)-1H-pyrazol-5-yl]-3-(7-{2-[3-(naphthalen-1-yl)-5,6-dihydro[1,2,4]triazolo[4,3-a]pyrazin-7(8H)-yl]ethoxy}-2,3-dihydro-1H-inden-4-yl)urea |
| 68 | 1-[3-tert-butyl-1-(4-methylphenyl)-1H-pyrazol-5-yl]-3-{7-[2-(3-cyclohexyl-5,6-dihydro[1,2,4]triazolo[4,3-a]pyrazin-7(8H)-yl)ethoxy]-2,3-dihydro-1H-inden-4-yl}urea |
| 69 | 1-[3-tert-butyl-1-(4-methylphenyl)-1H-pyrazol-5-yl]-3-(7-{2-[3-(3-methyl-1-benzofuran-2-yl)-5,6-dihydro[1,2,4]triazolo[4,3-a]pyrazin-7(8H)-yl]ethoxy}-2,3-dihydro-1H-inden-4-yl)urea |
| 70 | 1-[3-tert-butyl-1-(3,4,5-trimethoxyphenyl)-1H-pyrazol-5-yl]-3-(7-{2-[4-(cyclopropylmethyl)-3-oxopiperazin-1-yl]ethoxy}-2,3-dihydro-1H-inden-4-yl)urea |
| 71 | 1-[3-tert-butyl-1-(4-methylphenyl)-1H-pyrazol-5-yl]-3-(7-{2-[4-(cyclopropylmethyl)-3-oxopiperazin-1-yl]ethoxy}-2,3-dihydro-1H-inden-4-yl)urea methanesulfonate (1:1) |
| 72 | N-{5-tert-butyl-3-[({7-[2-(3-cyclohexyl-5,6-dihydro[1,2,4]triazolo[4,3-a]pyrazin-7(8H)-yl)ethoxy]-2,3-dihydro-1H-inden-4-yl}carbamoyl)amino]-2-methoxyphenyl}methanesulfonamide |
| 73 | N-(5-tert-butyl-3-{[(7-{2-[3-(5-chloro-2-hydroxyphenyl)-5,6-dihydro[1,2,4]triazolo[4,3-a]pyrazin-7(8H)-yl]ethoxy}-6-methyl-2,3-dihydro-1H-inden-4-yl)carbamoyl]amino}-2-methoxyphenyl)methanesulfonamide |
| 74 | N-(5-tert-butyl-2-methoxy-3-{[(7-{2-[3-(naphthalen-1-yl)-5,6-dihydro[1,2,4]triazolo[4,3-a]pyrazin-7(8H)-yl]ethoxy}-2,3-dihydro-1H-inden-4-yl)carbamoyl]amino}phenyl)methanesulfonamide |
| 75 | 1-[3-tert-butyl-1-(4-methylphenyl)-1H-pyrazol-5-yl]-3-(7-{2-[4-(ethylsulfonyl)-3-oxopiperazin-1-yl]ethoxy}-2,3-dihydro-1H-inden-4-yl)urea |
| 76 | 2-[7-(2-{[7-({[3-tert-butyl-1-(4-methylphenyl)-1H-pyrazol-5-yl]carbamoyl}amino)-2,3-dihydro-1H-inden-4-yl]oxy}ethyl)-5,6,7,8-tetrahydro[1,2,4]triazolo[4,3-a]pyrazin-3-yl]-4-chlorophenyl hexopyranosiduronic acid |
| 77 | N-{[3-tert-butyl-1-(4-methylphenyl)-1H-pyrazol-5-yl]carbamoyl}-N-(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)hexopyranuronosylamine |
| 78 | N-[3-tert-butyl-1-(4-methylphenyl)-1H-pyrazol-5-yl]-N-[(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)carbamoyl]hexopyranuronosylamine |
| 79 | 2-{4-[2-({7-[({5-tert-butyl-2-methoxy-3-[(methylsulfonyl)amino]phenyl}carbamoyl)amino]-2,3-dihydro-1H-inden-4-yl}oxy)ethyl]-2-oxopiperazin-1-yl}-N,N-dimethylacetamide |

-continued

| Compd. No. | Chemical Name |
|---|---|
| 80 | 2-[4-(2-{[7-({[3-tert-butyl-1-(4-methylphenyl)-1H-pyrazol-5-yl]carbamoyl}amino)-2,3-dihydro-1H-inden-4-yl]oxy}ethyl)-2-oxopiperazin-1-yl]-N,N-dimethylacetamide |
| 81 | N-{5-tert-butyl-3-[({7-[2-(4-cyclopropyl-3-oxopiperazin-1-yl)ethoxy]-2,3-dihydro-1H-inden-4-yl}carbamoyl)amino]-2-methoxyphenyl}methanesulfonamide |
| 82 | N-(5-tert-butyl-3-{[({7-{2-[4-(cyclopropylmethyl)-3-oxopiperazin-1-yl]ethoxy}-2,3-dihydro-1H-inden-4-yl)carbamoyl]amino}-2-hydroxyphenyl)ethanesulfonamide |
| 83 | N-(5-tert-butyl-3-{[({7-{2-[4-(cyclopropylmethyl)-3-oxopiperazin-1-yl]ethoxy}-2,3-dihydro-1H-inden-4-yl)carbamoyl]amino}-2-methoxyphenyl)ethenesulfonamide |
| 84 | 1-[3-tert-butyl-1-(4-methylphenyl)-1H-pyrazol-5-yl]-3-[7-(2-{3-[2-(hydroxymethyl)phenyl]-5,6-dihydro[1,2,4]triazolo[4,3-a]pyrazin-7(8H)-yl}ethoxy)-2,3-dihydro-1H-inden-4-yl]urea |
| 85 | 1-[3-tert-butyl-1-(4-methylphenyl)-1H-pyrazol-5-yl]-3-(7-{3-[3-(5-chloro-2-hydroxyphenyl)-5,6-dihydro[1,2,4]triazolo[4,3-a]pyrazin-7(8H)-yl]propoxy}-2,3-dihydro-1H-inden-4-yl)urea |
| 86 | 1-[3-tert-butyl-1-(4-methylphenyl)-1H-pyrazol-5-yl]-3-(7-{2-[3-(pyridin-2-yl)-5,6-dihydro[1,2,4]triazolo[4,3-a]pyrazin-7(8H)-yl]ethoxy}-2,3-dihydro-1H-inden-4-yl)urea |
| 87 | 1-[3-tert-butyl-1-(4-methylphenyl)-1H-pyrazol-5-yl]-3-(7-{2-[3-(2-ethylphenyl)-5,6-dihydro[1,2,4]triazolo[4,3-a]pyrazin-7(8H)-yl]ethoxy}-2,3-dihydro-1H-inden-4-yl)urea |
| 88 | 1-[3-tert-butyl-1-(4-methylphenyl)-1H-pyrazol-5-yl]-3-(7-{2-[3-(4-chloro-2-hydroxyphenyl)-5,6-dihydro[1,2,4]triazolo[4,3-a]pyrazin-7(8H)-yl]ethoxy}-2,3-dihydro-1H-inden-4-yl)urea |
| 89 | 1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)urea methanesulfonate |
| 90 | 1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)urea hydrochloride |

Definitions

The following definitions apply to the terms as used throughout this specification, unless otherwise limited in specific instances:

The term "compound" employed herein refers to any compound encompassed by the generic formula disclosed herein. The compounds described herein may contain one or more double bonds and therefore, may exist as isomers, stereoisomers, such as geometric isomers, E and Z isomers, and may possess asymmetric carbon atoms (optical centers) and therefore may exist as enantiomers or diastereoisomers. Accordingly, the chemical structures described herein encompasses all possible stereoisomers including the stereoisomerically pure form (e.g., geometrically pure) and stereoisomeric mixtures (racemates). The compound described herein, may exist as a conformational isomers such as chair or boat form. The compound described herein may also exist as atropisomers. The compounds may also exist in several tautomeric forms including the enol form, the keto form and mixtures thereof. Accordingly, the chemical structures described herein encompass all possible tautomeric forms of the compounds. The compounds described also include isotopically labeled compounds where one or more atoms have an atomic mass different from the atomic mass conventionally found in nature. Examples of isotopes that may be incorporated into the compounds of the invention include, but are not limited to $^2H$, $^3H$, $^{13}C$, $^{14}C$, $^{15}N$, $^{18}O$, $^{17}O$, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present invention.

The use of the terms "a" & "an" & "the" and similar referents in the context of describing the invention (especially in the context of the following claims) are to be construed to cover both the singular and the plural, unless otherwise indicated herein or clearly contradicted by context.

The nomenclature of the compounds of the present invention as indicated herein is according to ACD/Lab's Name Program (Version 12.0).

"Pharmaceutically acceptable salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, carbonic acid, phosphoric acid, and the like; or formed with organic acids such as acetic acid, propionic acid, isobutyric acid, hexanoic acid, cyclopentanepropionic acid, oxalic acid, glycolic acid, pyruvic acid, lactic acid, malonic acid, succinic acid, suberic acid, malic acid, maleic acid, fumaric acid, tartaric acid, citric acid, benzoic acid, 3-(4-hydroxybenzoyl) benzoic acid, phthalic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glucuronic acid, galactunoric acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. Also included are salts of amino acids such as arginate and the like (see, for example, Berge, S. M., et al., "Pharmaceutical Salts", Journal of Pharmaceutical Science, 1977, 66, 1-19). Alternatively, compounds of present invention can also form co-crystal with the mentioned acids, base or ions, which is included within the scope of pharmaceutically acceptable salt.

As used herein, the term "polymorph" pertains to compounds having the same chemical formula, the same salt type and having the same form of hydrate/solvate but having different crystallographic properties.

As used herein, the term "hydrate" pertains to a compound having a number of water molecules bonded to the compound.

As used herein, the term "solvate" pertains to a compound having a number of solvent molecules bonded to the compound.

The present invention also encompasses compounds which are in a prodrug form. Prodrugs of the compounds described herein are those compounds that readily undergo chemical changes under physiological conditions (in vivo) to provide the compounds of the present invention. Additionally, prodrugs can be converted to the compounds of the present invention by chemical or biochemical methods in an ex vivo environment, for example, transdermal patch reservoir with a suitable enzyme or chemical. Prodrugs are, in some situation, easier to administer than the parent drug. They may, for instance, be bioavailable by oral administration whereas the parent drug is not. The prodrug may also have improved solubility in pharmacological composition over the parent drug. Esters, peptidyl derivatives and the like, of the compounds are the examples of prodrugs of the present invention. In vivo hydrolysable (or cleavable) ester of a compound of the present invention that contains a carboxy group is, for example, a pharmaceutically acceptable ester which is hydrolysed in the human or animal body to produce the parent acid.

The term "substituted", as used herein, includes mono- and poly-substitution by a named substituent to the extent such single and multiple substitution (including multiple substitution at the same site) is chemically allowed and which means that any one or more hydrogens on the designated atom is replaced with a selection from the indicated group, provided that the designated atom's normal valence is not exceeded, and that the substitution results in a stable compound, for example, when a substituent is keto, then the two hydrogens on the atom are replaced. All substituents (R, $R_1$, $R_2$ . . . ) and their further substituents described herein may be attached to the main structure at any heteroatom or carbon atom which results in formation of stable compound.

As used herein, a "halogen" substituent is a monovalent halogen radical chosen from chloro, bromo, iodo and fluoro.

The term "$(C_1-C_3)$alkyl" or "$(C_1-C_6)$alkyl" used either alone or in attachment with another group refers to a saturated aliphatic hydrocarbon radical having the 1 to 3 or 1 to 6 carbon atoms respectively and that is unsubstituted or substituted. Said "$(C_1-C_3)$alkyl" or "$(C_1-C_6)$alkyl" is straight chain for example, methyl, ethyl, n-propyl, n-butyl, n-pentyl, n-hexyl and it may contain one or two double or triple bonds. Said "$(C_1-C_3)$alkyl" or $(C_1-C_6)$alkyl may also contain $(C_3-C_6)$cycloalkyl ring in a spiro manner.

The term "branched$(C_3-C_6)$alkyl" as used herein refers to a saturated aliphatic hydrocarbon radical having the 3 to 6 carbon atoms that is unsubstituted or substituted. Said alkyl includes branched chain for example isopropyl, isobutyl, sec-butyl, tert-butyl and it may suitably contain one or two double or triple bonds.

The term "$(C_3-C_6)$ cycloalkyl" used either alone or in attachment with another group refers to a cyclic ring system having the 3 to 6 carbon atoms and that may be unsubstituted or substituted. The "$(C_3-C_6)$cycloalkyl" means a cyclic ring system containing only carbon atom in the ring system backbone such as cyclopropyl, cyclobutyl, cyclopentyl, cyclohexyl. Cycloalkyl may have any degree of saturation provided that at least one ring in the ring system is not aromatic.

The term "aryl" refers to an aromatic group for example, which is a 6 to 10 membered monocyclic or bicyclic carbon-containing ring system. The aryl groups include, but are not limited to, phenyl, naphthyl, biphenyl, tetrahydronaphthyl and indanyl. Preferably, aryl is phenyl, indanyl or naphthyl.

The term "heteroaryl" refers to an aromatic group for example, which is a 5 to 14 membered monocyclic or bicyclic ring system, which has at least one heteroatom. The term "heteroatom" as used herein includes O, N, $S(O)_n$, wherein n is as defined above. In bicyclic ring system, ring can be fused through a bridge heteroatom. The heteroaryl groups include, but are not limited to pyrrolyl, furanyl (furyl), thiophenyl (thienyl), pyrazolyl, imidazolyl, oxazolyl, isoxazolyl, thiazolyl, triazolyl, oxadiazolyl, thiadiazolyl, tetrazolyl, pyridinyl (pyridyl), pyridazinyl, pyrimdinyl, pyrazinyl, triazinyl, indolyl, benzofuranyl, benzothiophenyl (benzothienyl), indazolyl, benzimidazolyl, benzoxazolyl, benzisoxazolyl, benzothiazolyl, quinolinyl, isoquinolinyl, cinnolinyl, quinazolinyl, quinoxalinyl, phthalazinyl or naphthyridinyl. Preferably heteroaryl is pyridinyl, thiophenyl, furanyl, pyrazolyl, imidazolyl, triazinyl or benzofuranyl.

The term "heterocyclic" or "heterocycle ring" refers to a fully or partially saturated cyclic group, for example, which is a 3 to 14 membered monocyclic or bicyclic ring system, which has at least one heteroatom. The term "heteroatom" as used herein includes O, N, $S(O)_n$ wherein n is as defined above. In bicyclic heterocyclic system, at least one ring is not aromatic and the rings can also be attached to each other in a spiro manner. The heterocycle groups include, but are not limited, oxiranyl, aziridinyl, oxetanyl, azetidinyl, pyrrolidinyl, dihydropyrrolyl, tetrahydrofuranyl, dihydrofuranyl, tetrahydrothiophenyl, dihydrothiophenyl, pyrazolidinyl, imidazolidinyl, oxazolidinyl, isoxazoiidinyl, thiazoiidinyl, triazolidinyl, oxadiazolidinyl, piperidinyl, tetrahydropyridinyl, dihydropyridinyl, piperazinyl, piperzinone, tetrahydropyranyl, dioxanyl, morpholinyl, thiomorpholinyl, triazinanyl, azepanyl, diazepanyl, diazepinyl, oxepanyl, dioxepanyl, oxazepanyl, oxazepinyl, indolinyl, benzomorpholinyl, tetrahydroquinolyl or tetrahydrisoquinolyl. Preferably heterocyclic is piperazinyl, piperzinone, morpholinyl, thiomorpholinyl, pyrrolidinyl or piperidinyl.

As used herein, "hydroxyl" refers to —OH group.

As used herein, "room temperature" refers to a temperature between 20° C. and 30° C.

As used herein, the term "mammal" means a human or an animal such as monkeys, primates, dogs, cats, horses, cows, etc.

The terms "treating" or "treatment" of any disease or disorder as used herein to mean administering a compound to a mammal in need thereof. The compound may be administered thereby providing a prophylactic effect in terms of completely or partially preventing or delaying the onset of a disease or disorder or sign or symptom thereof; and/or the compound may be administered thereby providing a partial or complete cure for a disease or disorder and/or adverse effect attributable to the disorder.

The phrase "a therapeutically effective amount" means the amount of a compound that, when administered to a patient for treating a disease, is sufficient to effect such treatment for the disease. The "therapeutically effective amount" will vary depending on the compound, mode of administration, the disease and its severity and the age, weight, etc., of the patient to be treated.

Throughout this specification and the appended claims it is to be understood that the words "comprise" "has" and "include" and variations such as "comprises", "comprising", "having", "includes", "including" are to be interpreted inclusively, unless the context requires otherwise. That is, the use of these words may imply the inclusion of an element or elements not specifically recited.

Also included within the scope of the invention are metabolites of compounds of formula (I), that is, compounds formed in vivo upon administration of the drug. Some examples of metabolites in accordance with the invention include following compounds—

| Compd. No. | Chemical Name |
|---|---|
| 91 | N-(5-tert-butyl-3-{[(4-{2-[4-(cyclopropylmethyl)-3-oxopiperazin-1-yl]ethoxy}-1H-inden-7-yl)carbamoyl]amino}-2-methoxyphenyl)ethenesulfonamide |
| 92 | N-(5-tert-butyl-3-{[(7-{2-[4-(cyclopropylmethyl)-3-oxopiperazin-1-yl]ethoxy}-2-hydroxy-2,3-dihydro-1H-inden-4-yl)carbamoyl]amino}-2-methoxyphenyl)ethanesulfonamide |
| 93 | N-(5-tert-butyl-3-{[(7-{2-[4-(cyclopropylmethyl)-3-oxopiperazin-1-yl]ethoxy}-3-hydroxy-2,3-dihydro-1H-inden-4-yl)carbamoyl]amino}-2-methoxyphenyl)ethanesulfonamide |
| 94 | N-(5-tert-butyl-3-{[(7-{2-[4-(cyclopropylmethyl)-3-oxopiperazin-1-yl]ethoxy}-2,3-dihydro-1H-inden-4-yl)carbamoyl]amino}-2-methoxyphenyl)-2-hydroxyethanesulfonamid |
| 95 | N-(5-tert-butyl-3-{[(7-{2-[4-(cyclopropylmethyl)-3-oxopiperazin-1-yl]ethoxy}-1-hydroxy-2,3-dihydro-1H-inden-4-yl)carbamoyl]amino}-2-methoxyphenyl)ethanesulfonamide |
| 96 | N-(5-tert-butyl-3-{[(7-{2-[4-(cyclopropylmethyl)-3-oxopiperazin-1-yl]ethoxy}-1H-inden-4-yl)carbamoyl]amino}-2-methoxyphenyl)ethanesulfonamide |
| 97 | N-(5-tert-butyl-3-{[(7-{2-[4-(cyclopropylmethyl)-3-oxopiperazin-1-yl]ethoxy}-1H-inden-4-yl)carbamoyl]amino}-2-methoxyphenyl)ethenesulfonamide |
| 98 | 1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-3-hydroxy-2,3-dihydro-1H-inden-4-yl)urea |
| 99 | 1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-1-hydroxy-2,3-dihydro-1H-inden-4-yl)urea |
| 100 | 1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-2-hydroxy-2,3-dihydro-1H-inden-4-yl)urea |
| 101 | 1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-2,3-dihydroxy-2,3-dihydro-1H-inden-4-yl)urea |
| 102 | 1-[3-tert-butyl-1-(4-methylphenyl)-1H-pyrazol-5-yl]-3-(4-{2-[3-(5-chloro-2-hydroxyphenyl)-5,6-dihydro[1,2,4]triazolo[4,3-a]pyrazin-7(8H)-yl]ethoxy}-1-hydroxy-1H-inden-7-yl)urea |
| 103 | 1-[3-tert-butyl-1-(4-methylphenyl)-1H-pyrazol-5-yl]-3-[7-{2-[3-(5-chloro-2-hydroxyphenyl)-5,6-dihydro[1,2,4]triazolo[4,3-a]pyrazin-7(8H)-yl]ethoxy}-2-hydroxy-1-(hydroxymethyl)-2,3-dihydro-1H-inden-4-yl]urea |
| 104 | 1-[3-tert-butyl-1-(4-methylphenyl)-1H-pyrazol-5-yl]-3-[7-{2-[3-(5-chloro-2-hydroxyphenyl)-5,6-dihydro[1,2,4]triazolo[4,3-a]pyrazin-7(8H)-yl]ethoxy}-1-(hydroxymethyl)-1H-inden-4-yl]urea |
| 105 | 1-{3-tert-butyl-1-[4-(hydroxymethyl)phenyl]-1H-pyrazol-5-yl}-3-(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)urea |
| 106 | 1-{3-tert-butyl-1-[4-(hydroxymethyl)phenyl]-1H-pyrazol-5-yl}-3-(7-{2-[3-(5-chloro-2-hydroxyphenyl)-5,6-dihydro[1,2,4]triazolo[4,3-a]pyrazin-7(8H)-yl]ethoxy}-1H-inden-4-yl)urea |
| 107 | 1-{3-tert-butyl-1-[4-(hydroxymethyl)phenyl]-1H-pyrazol-5-yl}-3-(4-{2-[3-(5-chloro-2-hydroxyphenyl)-5,6-dihydro[1,2,4]triazolo[4,3-a]pyrazin-7(8H)-yl]ethoxy}-1H-inden-7-yl)urea |

In another embodiment, present invention provides the process for preparing the compounds of formula (I).

The following reaction schemes are given to disclose the synthesis of the compounds according to the present invention.

Accordingly, the compounds of formula (I) of the present invention may be prepared as described in the schemes below.

Illustrative embodiments of compounds of formula I include compounds of formula I-A, formula I-B, formula I-C and formula I-D. In which the substituents are as defined in connection with general formula I and schemes 1-3.

amine of formula VI in the presence of suitable amine such as N,N-diisopropylethylamine (DIEA) in aprotic solvent such as isopropyl acetate, ethyl acetate or THF at room to reflux temperature. Compound of formula VI can be prepared by the Boc deprotection of compound of formula V using strong acids such as trifluoroacetic acid (TFA) in suitable solvent such as methylene dichloride (MDC) at 0° C. to room temperature. Compound of formula V is prepared by the reaction of hydroxyindane compound of formula IV with appropriate chloro compound of formula III. This reaction is carried out in the presence of suitable base such as potassium carbonate ($K_2CO_3$) and solvent such as Scheme 1:

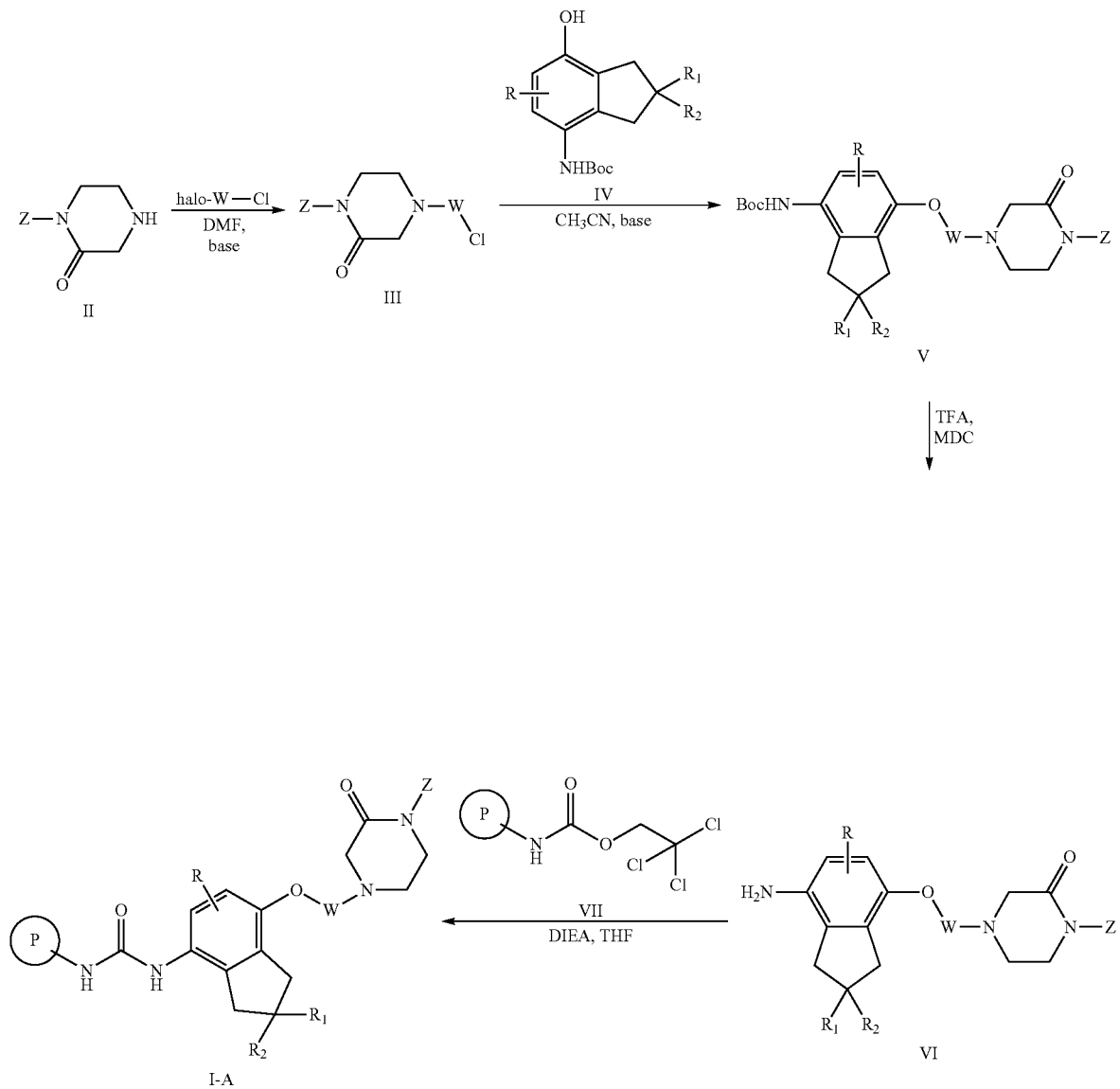

Synthesis of compounds of formula I-A, where substituents of general formula (I) such as $R_3$ is hydrogen, Y is C=O and Q is N, is shown in scheme 1. Other substitutions of formula (I) such as R, $R_1$, $R_2$, Z, P and W are same as defined above. Compound of formula I-A can be prepared by the reaction of appropriate carbamate of formula VII and acetonitrile ($CH_3CN$), THF, DMF or Dioxane at room temperature to 80° C. Compound of formula III is prepared by the N-alkylation of compound of formula II with suitable halides. The reaction is carried out in the presence of suitable base such as $K_2CO_3$ and solvent such as dimethyl formamide (DMF) at 0° C. to room temperature.

Scheme 2:

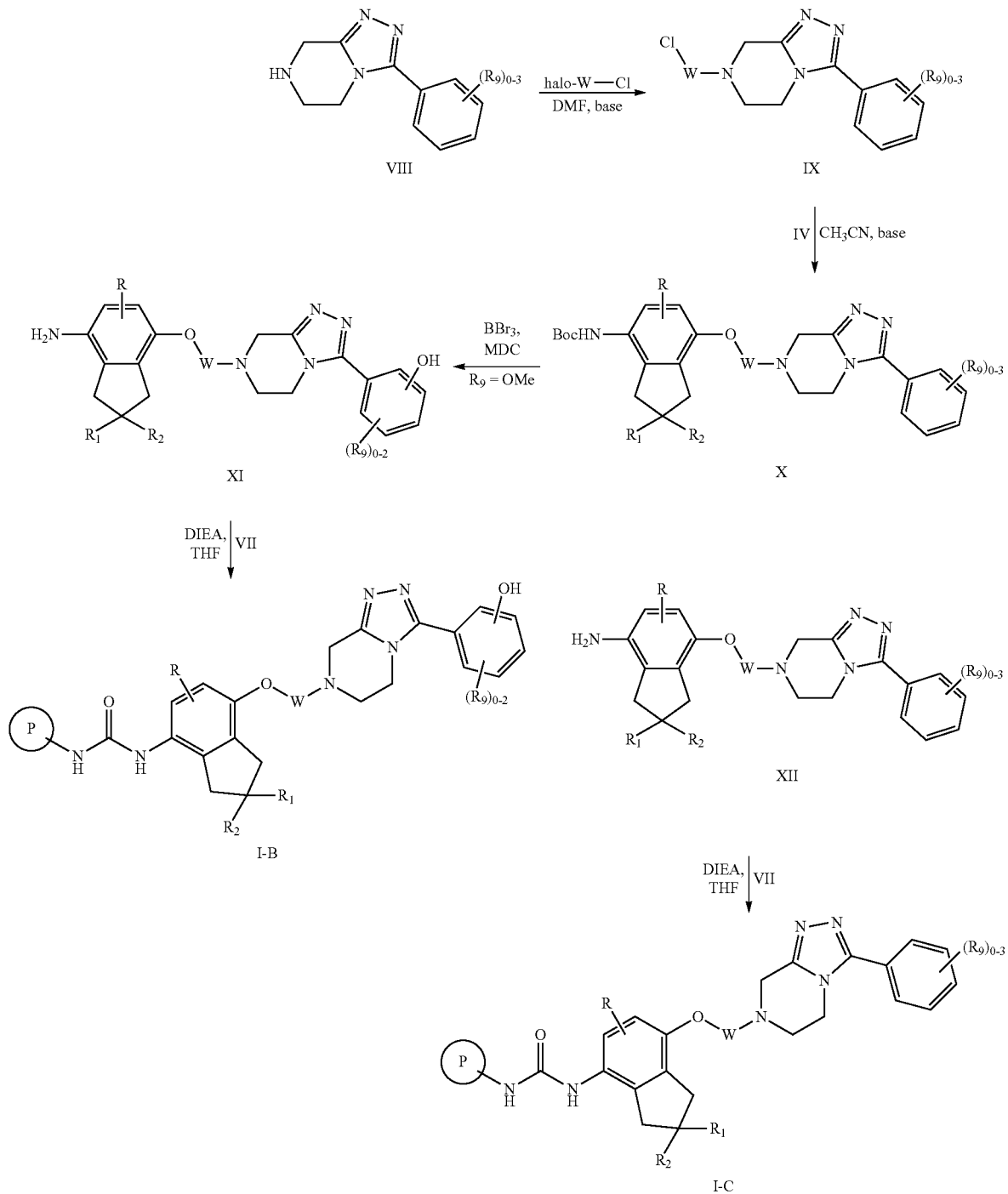

Synthesis of various compounds of formula I-B and I-C is shown in scheme 2, wherein substituents of general formula (I) are defined such as $R_8$ is phenyl, $R_3$ is hydrogen, Q is N, Y is C(Z') and Z and Z' forms a heteroaryl ring. Other substitutions of formula (I) such as R, $R_1$, $R_2$, P, $R_9$ and W are same as defined above. Compound of formula XI or XII is reacted, separately, with appropriate carbamate VII to obtain the compound of formula I-B and I-C, respectively, using similar condition as described for compounds of formula I-A as shown in scheme 1. Compound of formula X, where one of $R_9$ is OMe, is demethylated to yield the compound of formula XI. This reaction is performed using boron tribromide ($BBr_3$) in suitable solvent such as MDC at 0° C. to room temperature. In this case, Boc deprotection also occurs in situ. Boc deprotection of formula X is carried out in trifluoroacteic acid in solvent MDC to yield the compound of formula XII. Compounds of formula X is synthesized from compounds of formula IX using similar condition as described for compounds of formula V as shown in scheme 1. Similarly, compounds of formula IX is obtained from compounds of formula VIII using similar procedure as described for compounds of formula III as delineated in scheme 1. The OH group of formula I—B can be further derivatized using conventional methods known to a person skilled in the art.

sized from reaction of compounds of formula XIII and compounds of formula XIV. The reaction is carried out in the presence of suitable base such as triethyl amine and suitable solvent such as THF, dioxane and MDC.

Compounds of formula II, VIII and XIII are either commercially available or synthesized using conventional methods known to one of skill in the art. Some of compounds of Scheme 3:

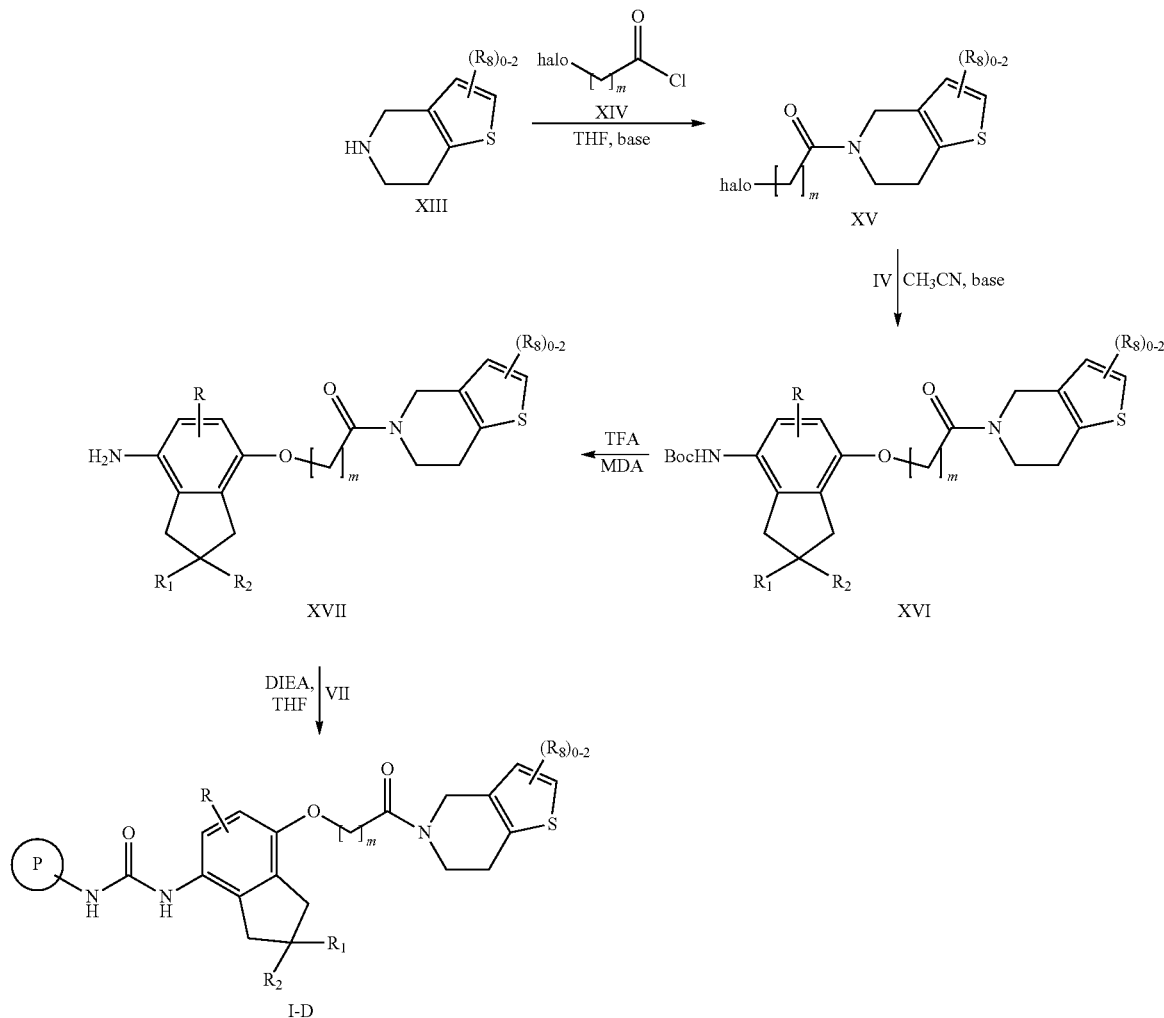

Compounds of formula I-D, wherein substituents of general formula (I) are defined such as $R_3$ is hydrogen, Q is C, W is —$(CH_2)_mCO$, Y is C(Z') and Z and Z' forms a heteroaryl ring, are synthesized as shown in scheme 3. Other substitutions of formula (I) such as R, $R_1$, $R_2$, P, m and $R_8$ are same as defined above. Compound of formula XVII is reacted with appropriate carbamate VII to obtain the compound of formula I-D using similar condition as described for compounds of formula I-A as shown in scheme 1. Boc deprotection of compounds of formula XVI is carried out to yield the compounds of formula XVII using similar condition as described for compounds of formula VI. Compounds of formula XVI is synthesized from reaction of compounds of formula XV and compound of formula IV using similar condition as described for compounds of formula V as shown in scheme 1. Compounds of formula XV is syntheformula VIII are synthesized from appropriate starting material using similar procedure as described in Modern Drug Synthesis, Edited by Jie Jack Li and Douglas S. Johnson, 2010, pp 131, Published by John Wiley & Sons. Several compounds of formula XIII are synthesized using the procedure as described in Indian Journal of Chemistry, 47B(1), 97-105 (2008), J. Heterocyclic Chem., 46, 975-979 (2009) and Chem Ber, 99, 94 (1966).

Schemes 1-3 given herein above provide general method of preparation of compounds of present invention. One of ordinary skill will recognize to introduce various substituents such as R, $R_1$, $R_2$, $R_3$, $R_8$, $R_9$, $R_a$, $R_b$, $R_c$, W, P, Q, Y, Z and Z' etc in appropriately modified starting material containing the various substituents. Alternative to the given schemes, one of ordinary skill will readily synthesize the compounds according to the present invention using conventional synthetic organic techniques from suitable starting material which are either commercially available or may be readily prepared.

It is within the purview of a person skilled in the art that variations in reaction time, temperature, solvents and/or reagents could increase the yields.

In present specification some general terms are used with their known intended meaning which are defined herein below:

| | |
|---|---|
| DMF | Dimethyl formamide |
| BoC | tert-butoxycarbonyl |
| MDC | Methylene dichloride |
| THF | Tetrahydrofuran |
| DIEA | N,N-diisopropylethylamine |
| TFA | Trifluoroacetic acid |
| ESMS | Electrospray Mass Spectrometry |
| ESI | Electro spray ionization |
| APCI | Atmospheric pressure chemical ionization |
| μM | Micro Molar |
| NM | Nano Molar |

Mass of compounds prepared according to present invention is measured using Single quadrupole mass spectrometer (Water ZQ 2000 instrument) using APCI ionization technique (Electro spray chemical ionization Probe) or Finnigan LXQ, thermo instrument Technique using either ESI or APCI.

The novel compounds of the present invention were prepared according to the procedure of the schemes as described herein above, using appropriate materials and are further exemplified by the following specific examples. The examples are not to be considered or construed as limiting the scope of the invention set forth.

EXAMPLES FOR PREPARATION OF INTERMEDIATES

Example 1

Tert-butyl (7-hydroxy-2,3-dihydro-1H-inden-4-yl) carbamate (Intermediate 1)

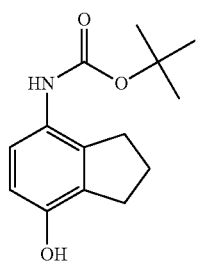 [SMILES: CC(C)(C)OC(=O)Nc1ccc(O)c2c1CCC2]

To a stirred solution of 7-amino-2,3-dihydro-1H-inden-4-ol (40 gm, 161 mmol) (prepared by the procedure as described in U.S. Pat. No. 6,203,580) and triethyl amine (26.71 ml, 192 mmol) in ethyl acetate (500 ml), di-tert-butylpyrocarbonate (37 ml, 161 mmol) was added over a period of 1 h at room temperature. The reaction mixture was further stirred at room temperature for 1 h. The reaction mixture was quenched by water, stirred and ethyl acetate layer was separated, dried over sodium sulfate and concentrated under vacuum to get residual solid. The residue was stirred in hexane (500 ml) for 1 h at room temperature. The solid appeared, was filtered and dried under vacuum to get 38.0 gm of title compound as solid.

$^1$H-NMR (400 MHz, CDCl$_3$): δ 7.19 (1H, d), 6.48 (1H, d), 6.11 (1H, s), 5.82 (1H, bs), 2.80 (4H, q), 2.03-2.10 (2H, m), 1.50 (9H, s).
ESMS: 250.08

Example 2

2,2,2-trichloroethyl[3-tert-butyl-1-(4-methylphenyl)-1H-pyrazol-5-yl]carbamate (Intermediate 2)

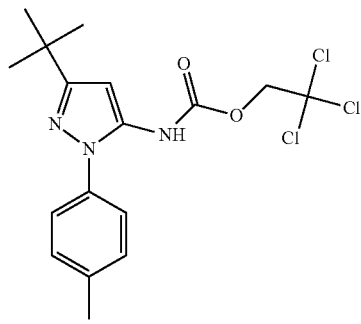 [SMILES: Cc1ccc(-n2nc(C(C)(C)C)cc2NC(=O)OCC(Cl)(Cl)Cl)cc1]

To a stirred solution of 3-tert-butyl-1-(4-methylphenyl)-1H-pyrazol-5-amine (80 gm, 349 mmol) (*J. Med. Chem.*, 2002, 45, 2994-3008) and sodium bicarbonate (80 gm, 952.38 mmol) in tetrahydrofuran (500 ml), 2,2,2-trichloroethyl chloroformate (57 ml, 420 mmol) was added at 5-10° C. The reaction mixture was stirred at room temperature for 4 h. The reaction mixture was poured into water and extracted by ethyl acetate. Ethyl acetate layer was separated, dried over sodium sulfate and evaporated under vacuum to get crude compound.

The crude compound was suspended in hexane (500 ml), stirred at 0-5° C. and separated solid was filtered and dried to get 102.0 gm of title compound as solid.

$^1$H-NMR (400 MHz, DMSO-d$_6$): δ 9.90 (1H, s), 7.35 (2H, d), 7.25 (2H, d), 6.26 (1H, s), 4.85 (2H, s), 2.33 (3H, s), 1.27 (9H, s).
ESMS: 403.90, 405.91

Example 3

2,2,2-trichloroethyl{5-tert-butyl-3-[(ethylsulfonyl) amino]-2-methoxyphenyl} carbamate (Intermediate 3)

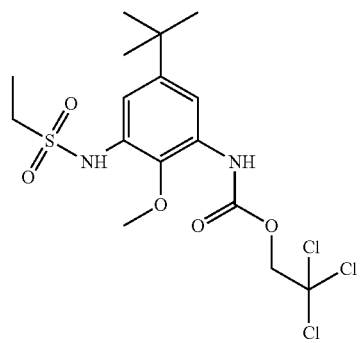 [SMILES: CCS(=O)(=O)Nc1cc(C(C)(C)C)cc(NC(=O)OCC(Cl)(Cl)Cl)c1OC]

Using the similar procedure as described for 2,2,2-trichloroethyl[3-tert-butyl-1-(4-methylphenyl)-1H-pyrazol-5-yl] carbamate (Intermediate 2) in Example 2, the title compound was synthesized from N-(3-amino-5-tert-butyl-2-methoxyphenyl)ethanesulfonamide (J. Med. Chem., 2007, 50, 4016-4026) and 2,2,2-trichloroethyl chloroformate.

$^1$H-NMR (400 MHz, DMSO-d$_6$): δ 9.44 (1H, s), 9.11 (1H, s), 7.34 (1H, s), 7.18 (1H, d), 4.93 (2H, s), 3.70 (3H, s), 3.09-3.20 (2H, m), 1.28 (12H, m)

ESMS: 460.95

Using the similar procedure as described for 2,2,2-trichloroethyl[3-tert-butyl-1-(4-methylphenyl)-1H-pyrazol-5-yl] carbamate (Intermediate 2), 2,2,2-trichloroethyl [3-tert-butyl-1-(3-chloro-4-hydroxyphenyl)-1H-pyrazol-5-yl] carbamate (Intermediate 4), 2,2,2-trichloroethyl[3-tert-butyl-1-(3-chloro-4-methoxyphenyl)-1H-pyrazol-5-yl] carbamate (Intermediate 5), 2,2,2-trichloroethyl [3-tert-butyl-1-(4-methoxyphenyl)-1H-pyrazol-5-yl]carbamate (Intermediate 6) and 2,2,2-trichloroethyl [3-tert-butyl-1-(3-chloro-4-methylphenyl)-1H-pyrazol-5-yl] carbamate (Intermediate 7) were synthesized from corresponding aminopyrazole compound.

Example 4

Tert-butyl 2-nitro-6,7-dihydrothieno[3,2-c]pyridine-5(4H)-carboxylate (Intermediate 8)

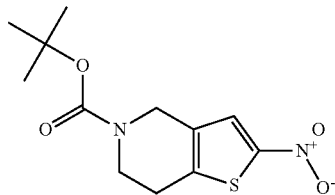

To a stirred solution of 2-nitro-4,5,6,7-tetrahydrothieno [3,2-c]pyridine (50 gm, 271.73 mmol) and triethyl amine (86.57 ml, 600 mmol) in tetrahydrofuran (500 ml), di-tert-butyl pyrocarbonate (69 ml, 300 mmol) was added at room temperature. The reaction mixture was stirred at room temperature for 3 h and concentrated under vacuum. The residue was dissolved in ethyl acetate and washed by water. Ethyl acetate layer was separated, dried over Na$_2$SO$_4$ and concentrated under vacuum to get 52.0 gm of title compound as solid.

Example 5

Tert-butyl 2-(acetylamino)-6,7-dihydrothieno[3,2-c]pyridine-5(4H)-carboxylate (Intermediate 9)

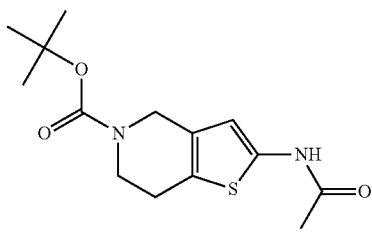 [SMILES: CC(=O)Nc1cc2c(s1)CCN(C(=O)OC(C)(C)C)C2]

To a stirred solution of tert-butyl 2-nitro-6,7-dihydrothieno[3,2-c]pyridine-5(4H)-carboxylate (Intermediate 8) (52 gm, 183.09 mmol) and acetic anhydride (52 ml, 520 mmol) in acetic acid (500 ml), iron powder (52.08 gm, 930 mmol) was added at room temperature. The reaction mixture was stirred at room temperature for 5 h and quenched by water. The reaction mixture was basified to pH 8-9 by aqueous sodium bicarbonate solution and extracted by ethyl acetate. Ethyl acetate layer was separated, dried over Na$_2$SO$_4$ and concentrated under vacuum to get 45.0 gm of title compound as solid.

Example 6

N-[5-(chloroacetyl)-4,5,6,7-tetrahydrothieno[3,2-c] pyridin-2-yl]acetamide (Intermediate 10)

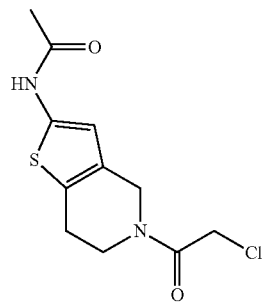 [SMILES: CC(=O)Nc1cc2c(s1)CCN(C(=O)CCl)C2]

To a stirred solution of tert-butyl 2-(acetylamino)-6,7-dihydrothieno[3,2-c]pyridine-5(4 H)-carboxylate (Intermediate 9) (45 gm, 152.02 mmol) in dichloromethane (500 ml), trifluoroacetic acid (58.54 ml, 760 mmol) was added at room temperature. The reaction mixture was stirred at room temperature for 1 h. The reaction mixture was concentrated under vacuum to get 40 gm of TFA salt of N-(4,5,6,7-tetrahydrothieno[3,2-c]pyridin-2-yl)acetamide. To a stirred solution of obtained residue of N-(4,5,6,7-tetrahydrothieno [3,2-c]pyridin-2-yl)acetamide and triethyl amine (65.8 ml, 456.08 mmol) in dichloromethane (500 ml), chloroacetyl chloride (13.39 ml, 168 mmol) was added and the reaction mixture was stirred at room temperature for 1 h. The reaction mixture was concentrated under vacuum and water was added to the residue. The solution stirred at room temperature for 15 minute. The solid thus obtained was filtered and dried under vacuum to get 40.0 gm of title compound as solid.

ESMS: 273.33, 271.41

Example 7

7-(2-chloroethyl)-3-(5-chloro-2-methoxyphenyl)-5,6,7,8-tetrahydro[1,2,4]triazolo [4,3-a]pyrazine (Intermediate 11)

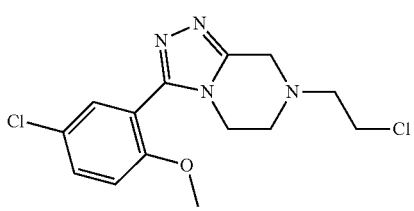 [SMILES: COc1ccc(Cl)cc1-c1nnc2n1CCN(CCCl)C2]

To a stirred solution of 3-(5-chloro-2-methoxyphenyl)-5,6,7,8-tetrahydro[1,2,4]triazolo [4,3-a]pyrazine (88 gm, 333.33 mmol) and potassium carbonate (138 gm, 1000 mmol) in dimethyl formamide (700 ml), 1-bromo-2-chloroethane (138 ml, 1659 mmol) was added at room temperature. The reaction mixture was stirred at room temperature for 36 h. The reaction mixture was quenched with water and extracted with toluene. Toluene layer was separated, dried over sodium sulfate and concentrated under vacuum. The residue was stirred in 50 ml toluene at room temperature for 30 min. The solid thus obtained was filtered and dried under vacuum to get 40.0 gm of title compound as solid.

$^1$H-NMR (400 MHz, DMSO-$d_6$): δ 7.58-7.61 (1H, dd), 7.42 (1H, d), 7.24 (1H, d), 3.89 (2H, s), 3.82 (3H, s), 3.77-3.80 (4H, m), 2.91-2.94 (4H, m).

ESMS: 326.91, 328.86

Example 8

4-(2-chloroethyl)-1-(cyclopropylmethyl)piperazin-2-one (Intermediate 12)

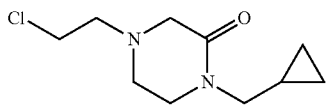 [SMILES: O=C1CN(CCCl)CCN1CC1CC1]

Using the similar procedure as described for 7-(2-chloroethyl)-3-(5-chloro-2-methoxyphenyl)-5,6,7,8-tetrahydro[1,2,4]triazolo [4,3-a]pyrazine (Intermediate 11) in example 7, the title compound was synthesized from 1-(cyclopropylmethyl)piperazin-2-one and 1-bromo-2-chloro ethane.

$^1$H-NMR (400 MHz, CDCl$_3$): 3.63 (2H, t), 3.48 (2H, t), 3.00-3.32 (4H, m), 2.82-2.85 (4H, m), 0.89 (1H, m), 0.47-0.56 (2H, m), 0.25-0.31 (2H, m).

ESMS: 217.06, 219.08

Example 9

Tert-butyl(7-{2-[3-(5-chloro-2-methoxyphenyl)-5,6-dihydro[1,2,4]triazolo[4,3-a]pyrazin-7(8H)-yl]ethoxy}-2,3-dihydro-1H-inden-4-yl)carbamate (Intermediate 13)

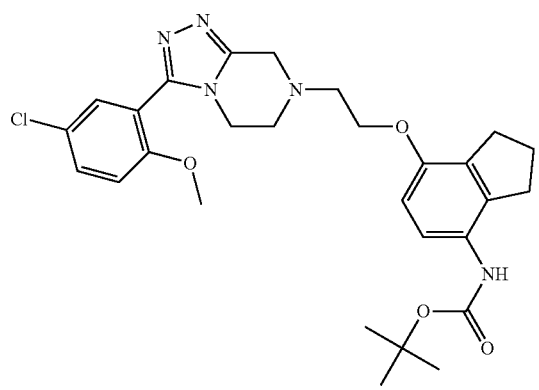 [SMILES: COc1ccc(Cl)cc1-c1nnc2n1CCN(CCOc1ccc(NC(=O)OC(C)(C)C)c3c1CCC3)C2]

To a stirred solution of 7-(2-chloroethyl)-3-(5-chloro-2-methoxyphenyl)-5,6,7,8-tetra hydro[1,2,4]triazolo[4,3-a] pyrazine (Intermediate 11) (40 gm, 122.32 mmol) and tert-butyl(7-hydroxy-2,3-dihydro-1H-inden-4-yl)carbamate (Intermediate 1) (30.45 gm, 122.32 mmol) in acetonitrile, potassium carbonate (50.5 gm, 366 mmol) was added at room temperature. The reaction mixture was stirred at 75-85° C. for 24 h. The reaction mixture was quenched with water and extracted with toluene. Toluene layer was separated, dried over sodium sulfate and concentrated under vacuum. The residue was stirred in 50 ml toluene at room temperature for 1 h. The solid obtained was filtered and dried under vacuum to get 40.0 gm of title compound as solid.

$^1$H-NMR (400 MHz, DMSO-$d_6$): δ 8.46 (1H, s), 7.59 (1H, d), 7.42 (1H, s), 7.23 (2H, d), 6.74 (1H, d), 4.16 (2H, t), 3.95 (2H, s), 3.82 (3H, s), 3.80 (2H, m), 2.97 (4H, m), 2.78 (4H, t), 1.96 (2H, m), 1.44 (9H, s).

ESMS: 540.05

Example 10

Tert-butyl(7-{2-[4-(cyclopropylmethyl)-3-oxopiperazin-1-yl]ethoxy}-2,3-dihydro-1H-inden-4-yl)carbamate (Intermediate 14)

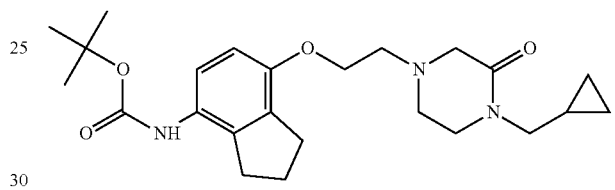

Using the similar procedure as described for tert-butyl(7-{2-[3-(5-chloro-2-methoxyphenyl)-5,6-dihydro[1,2,4]triazolo[4,3-a]pyrazin-7(8H)-yl]ethoxy}-2,3-dihydro-1H-inden-4-yl) carbamate (Intermediate 13) in example 9, the title compound was synthesized from 4-(2-chloroethyl)-1-(cyclopropylmethyl)piperazin-2-one (Intermediate 12) and tert-butyl 7-hydroxy-2,3-dihydro-1H-inden-4-yl) carbamate (Intermediate 1).

$^1$H-NMR (400 MHz, DMSO-$d_6$): δ 8.45 (1H, s), 7.09 (1H, d), 6.70 (1H, d), 4.07 (2H, t), 3.35-3.36 (2H, m, partially merged with water peak), 3.16-3.13 (4H, m), 2.74-2.79 (8H, m), 1.91-1.99 (2H, m), 1.44 (9H, s), 0.90-0.93 (1H, m), 0.37-0.45 (2H, m), 0.17-0.19 (2H, m).

ESMS: 430.09

Example 11

Tert-butyl(7-{2-[2-(acetylamino)-6,7-dihydrothieno[3,2-c]pyridin-5(4H)-yl]-2-oxo ethoxy}-2,3-dihydro-1H-inden-4-yl)carbamate (Intermediate 15)

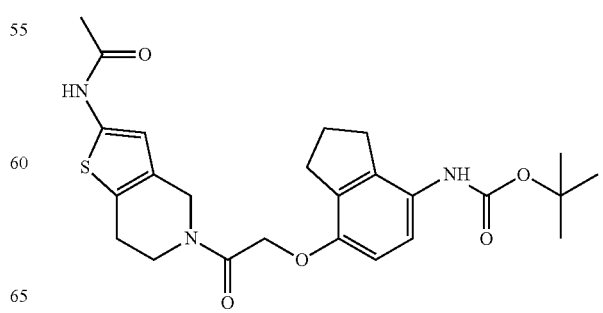

Using the similar procedure as described for tert-butyl(7-{2-[3-(5-chloro-2-methoxy phenyl)-5,6-dihydro[1,2,4]triazolo[4,3-a]pyrazin-7(8H)-yl]ethoxy}-2,3-dihydro-1H-inden-4-yl)carbamate (Intermediate 13) in example 9, the title compound was synthesized from N-[5-(chloroacetyl)-4,5,6,7-tetrahydrothieno[3,2-c]pyridin-2-yl]acetamide (Intermediate 10) and tert-butyl(7-hydroxy-2,3-dihydro-1H-inden-4-yl)carbamate (Intermediate 1).

Example 12

7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-amine (Intermediate 16)

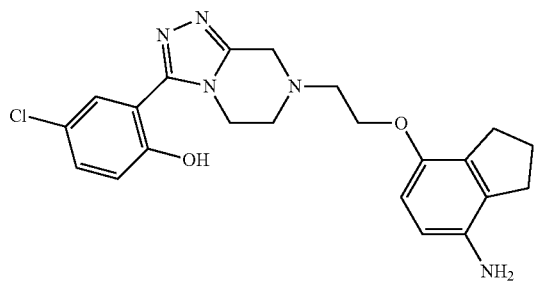 [SMILES: Nc1ccc(OCCN2CCn3c(nnc3-c3cc(Cl)ccc3O)C2)c2c1CCC2]

To a stirred solution of tert-butyl(7-{2-[3-(5-chloro-2-methoxyphenyl)-5,6-dihydro [1,2,4]triazolo[4,3-a]pyrazin-7(8H)-yl]ethoxy}-2,3-dihydro-1H-inden-4-yl)carbamate (Intermediate 13) (40 gm, 74.07 mmol), in dichloromethane (400 ml), boron tribromide (35 ml, 370 mmol) was added drop wise over a period of 30 min. at room temperature. The reaction mixture was stirred at room temperature for 10-12 h. The reaction mixture was quenched with water. Dichloromethane layer was separated and the pH of aqueous layer was adjusted to 8-9 by aqueous sodium bicarbonate solution. The solid obtained was filtered and dried under vacuum to get 25.0 gm of title compound as solid.

$^1$H-NMR (400 MHz, DMSO-$d_6$): δ 10.91 (1H, s), 7.40-7.43 (2H, m), 7.03 (1H, d), 6.54 (1H, d), 6.35 (1H, d), 4.43 (2H, bs), 4.00-4.05 (4H, m), 3.94 (2H, s), 2.98 (2H, m), 2.93 (2H, m), 2.74 (2H, t), 2.63 (2H, t), 1.94-1.98 (2H, m).
ESMS: 426.00

Example 13

4-{2-[(7-amino-2,3-dihydro-1H-inden-4-yl)oxy]ethyl}-1-(cyclopropylmethyl)piperaz-in-2-one (Intermediate 17)

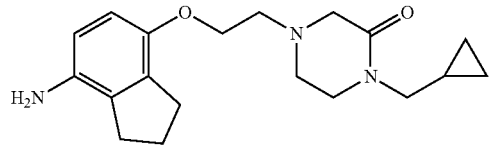 [SMILES: Nc1ccc(OCCN2CCN(CC3CC3)C(=O)C2)c2c1CCC2]

To a stirred solution of tert-butyl(7-{2-[4-(cyclopropylmethyl)-3-oxopiperazin-1-yl]ethoxy}-2,3-dihydro-1H-inden-4-yl)carbamate (Intermediate 14) (58 gm, 135.19 mmol) in dichloromethane (500 ml), trifluoroacetic acid (31.2 ml, 405 mmol) was added at 0° C. The reaction mixture was stirred at room temperature for 6 h. The reaction mixture was quenched with water and basified to pH-8 by sodium bicarbonate in water. Dichloromethane layer was separated, dried over sodium sulfate and concentrated under vacuum and further stirred in di-isopropyl ether. The resultant solid was filtered and dried under vacuum to get 55.0 gm of title compound as solid.

$^1$H-NMR (400 MHz, DMSO-$d_6$): δ 7.02 (1H, d), 6.85 (1H, d), 4.25 (2H, bs), 3.66 (2H, bs), 3.54 (2H, bs), 3.21-3.29 (6H, m), 2.81-2.87 (4H, m), 2.05 (2H, m), 0.95 (1H, m), 0.45 (2H, d), 0.22 (2H, bs).
ESMS: 330.12

Example 14

N-(5-{[(7-amino-2,3-dihydro-1H-inden-4-yl)oxy]acetyl}-4,5,6,7-tetrahydrothieno [3,2-c]pyridin-2-yl)acetamide (Intermediate 18)

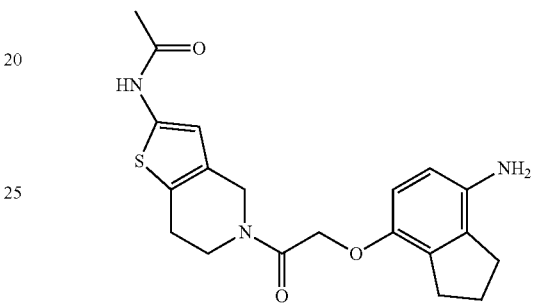

Using the similar procedure as described for 4-{2-[(7-amino-2,3-dihydro-1H-inden-4-yl)oxy]ethyl}-1-(cyclopropylmethyl)piperaz-in-2-one (Intermediate 17), the title compound was synthesized from tert-butyl(7-{2-[2-(acetylamino)-6,7-dihydrothieno[3,2-c]pyridin-5(4H)-yl]-2-oxoethoxy}-2,3-dihydro-1H-inden-4-yl)carbamate (Intermediate 15) and trifluoroacetic acid.

Other intermediate compounds useful for the preparation of compounds of the present invention can also be prepared in analogous manner by using the synthetic schemes as described above:

EXAMPLES FOR PREPARATION OF COMPOUNDS ACCORDING TO PRESENT INVENTION

Example 15

1-[3-tert-butyl-1-(4-methylphenyl)-1H-pyrazol-4-yl]-3-(7-{2-[3-(5-chloro-2-hydroxy phenyl)-5,6-dihydro[1,2,4]triazolo[4,3-a]pyrazin-7(8H)-yl]ethoxy}-2,3-dihydro-1H-inden-4-yl)urea
(Compound No. 38)

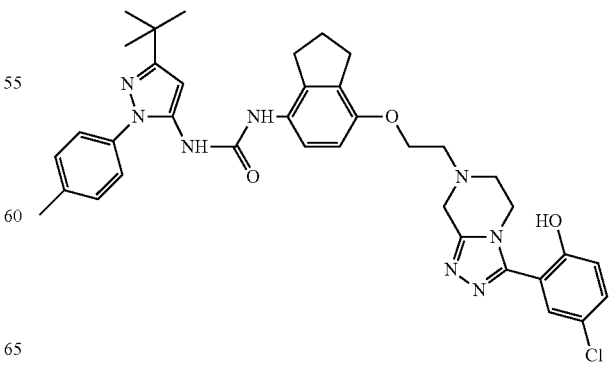

To a stirred solution of 7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-amine (Intermediate 16) (25 gm, 58.82 mmol) and N,N-diisopropylethylamine (31.50 ml, 176 mmol) in ethyl acetate (250 ml), 2,2,2-trichloro ethyl[3-tert-butyl-1-(4-methylphenyl)-1H-pyrazol-5-yl]carbamate (Intermediate 2) (28.28 gm, 70 mmol) was added at room temperature. The reaction mixture was refluxed for 8-12 h. The reaction mixture was cooled to room temperature and the separated solid was filtered, washed with di-isopropyl ether (500 ml), dried under vacuum and crystallized by Ethanol to get 22.0 gm of title compound as white solid.

$^1$H-NMR (400 MHz, DMSO-$d_6$): δ 10.91 (1H, s), 8.50 (1H, s), 8.20 (1H, s), 7.51 (1H, d), 7.38-7.43 (4H, m), 7.33 (2H, d), 7.03 (1H, d), 6.75 (1H, d), 6.32 (1H, s), 4.15 (2H, bs), 4.01 (2H, bs), 3.96 (2H, s), 2.98-3.00 (4H, m), 2.80 (2H, t), 2.72 (2H, t), 2.37 (3H, s), 2.00 (2H, t), 1.26 (9H, s)

ESMS: 681.28 (M$^+$)

Example 16

N-(5-tert-butyl-3-{[(7-{2-[4-(cyclopropylmethyl)-3-oxopiperazin-1-yl]ethoxy}-2,3-di hydro-1H-inden-4-yl)carbamoyl]amino}-2-methoxyphenyl)ethanesulfonamide (Compound No. 43)

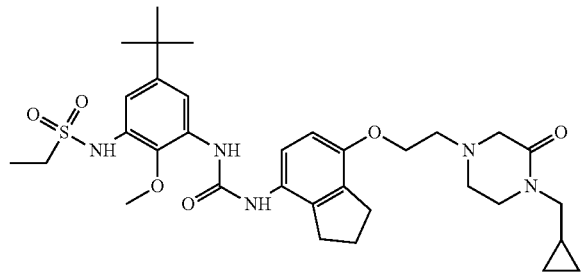 [SMILES: CCS(=O)(=O)Nc1cc(C(C)(C)C)cc(NC(=O)Nc2ccc(OCCN3CCN(CC4CC4)C(=O)C3)c3c2CCC3)c1OC]

To a stirred solution of 4-{2-[(7-amino-2,3-dihydro-1H-inden-4-yl)oxy]ethyl})-1-(cyclo propylmethyl)piperazin-2-one (Intermediate 17) (55 gm, 129.13 mmol) and N,N-diisopropyethylamine (70.33 ml, 545 mmol) in isopropyl acetate (300 ml), 2,2,2-trichloroethyl {5-tert-butyl-3-[(ethylsulfonyl)amino]-2-methoxyphenyl}carbamate (Intermediate 3) (74.46 gm, 161.25 mmol) was added at room temperature. The reaction mixture was refluxed for 8-12 h. The reaction mixture was cooled to room temperature and the separated solid was filtered, washed with di-isopropyl ether (500 ml), dried under vacuum and crystallized by ethanol to get 50.0 gm of title compound as white solid.

$^1$H-NMR (400 MHz, DMSO-$d_6$): δ 9.05 (1H, s), 8.59 (1H, s), 8.43 (1H, s), 8.08 (1H, d), 7.61 (1H, d), 6.95 (1H, d), 6.73 (1H, d), 4.08 (2H, t), 3.71 (3H, s), 3.33 (2H, partially merged with water signal), 3.10-3.17 (6H, m), 2.74-2.84 (8H, m), 2.02 (2H, m), 1.28 (3H, t), 1.23 (9H, s), 0.94 (1H, m), 0.41-0.46 (2H, m), 0.19 (2H, m).

ESMS: 642.10 (M+1)

Example 17

N-[5-({[7-({[3-tert-butyl-1-(4-methylphenyl)-1H-pyrazol-5-yl]carbamoyl}amino)-2,3-dihydro-1H-inden-4-yl]oxy}acetyl)-4,5,6,7-tetrahydrothieno[3,2-c]pyridin-2-yl]acetamide (Compound No. 52)

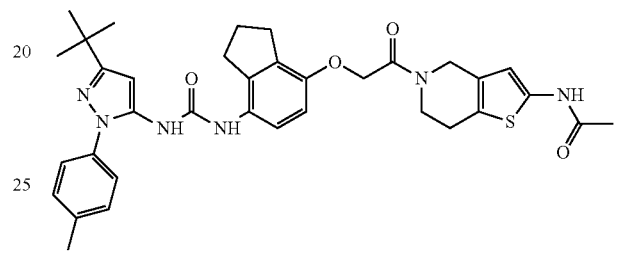

To a stirred solution of N-(5-{[(7-amino-2,3-dihydro-1H-inden-4-yl)oxy]acetyl}-4,5,6,7-tetrahydrothieno[3,2-c]pyridin-2-yl)acetamide (Intermediate 18) (25 gm, 64.93 mmol) and N,N-diisopro-pylethylamine (33.09 ml, 195 mmol) in tetrahydrofuran (250 ml), 2,2,2-trichloroethyl[3-tert-butyl-1-(4-methylphenyl)-1H-pyrazol-5-yl]carbamate (Intermediate 2) (31.51 gm, 78 mmol) was added. The reaction mixture was refluxed for 8-12 h. The reaction mixture was cooled to room temperature and quenched with water. The reaction mixture was extracted by ethyl acetate. Ethyl acetate layer was dried over sodium sulphate and concentrated under vacuum. The concentrate was stirred with di-isopropyl ether (500 ml), filtered, dried under vacuum and crystallized by ethanol to get 20.0 gm of title compound as white solid.

$^1$H-NMR (400 MHz, DMSO-$d_6$): δ 11.03 (1H, s), 8.48 (1H, s), 8.19 (1H, s), 7.43 (1H, t), 7.38 (2H, d), 7.33 (2H, d), 6.64 (1H, t), 6.37 (1H, s), 6.32 (1H, s), 4.83 (2H, d), 4.43-4.50 (2H, d), 3.73 (2H, m), 2.65-2.82 (6H, m), 2.37 (3H, s), 1.88-1.91 (5H, m), 1.26 (9H, s).

ESMS: 641.57 (M+1), 639.59 (M−1)

The following representative compounds of the present invention were prepared in analogous manner by using the synthetic schemes as described above:

TABLE 1

| Comp. No. | $^1$H-NMR (400 MHz, DMSO-$d_6$) | MASS |
|---|---|---|
| 1 | NMR (CDCl3) δ 7.26-7.30 (2H, m), 7.16 (2H, d), 6.85-6.93 (2H, m), 6.55 (1H, d), 6.32 (1H, s), 4.98-5.08 (2H, m), 4.74 (2H, s), 3.94-4.19 (4H, m), 2.81 (2H, m), 2.56 (2H, m), 2.32 (3H, s), 1.98-2.00 (2H, m), 1.32 (9H, s) | 635.59 (M − 1) |
| 2 | NMR (CDCl3) δ 7.43 (2H, d), 7.29-7.36 (3H, m), 6.63 (1H, m), 6.48 (1H, m), 6.33 (2H, s), 5.04-5.12 (2H, m), 4.77 (2H, s), 4.08-4.14 (4H, m), 2.85 (2H, m), 2.62 (2H, m), 2.03 (2H, m), 1.34 (9H, s), 1.31 (9H, s) | 679.64 (M + 1) |
| 3 | NMR (CDCl3) δ 8.34 (1H, s), 7.92 (1H, m), 7.67 (1H, d), 7.47 (2H, d), 7.31 (2H, d), 6.66 (1H, m), 6.46 (1H, s), 5.15 (1H, s), 5.04 (1H, s), 4.80 (2H, s), 4.24 (1H, s), 4.10-4.13 (2H, m), 2.88 (2H, t), 2.76 | 705.61 (M + 1) |

TABLE 1-continued

| Comp. No. | ¹H-NMR (400 MHz, DMSO-d₆) | MASS |
|---|---|---|
| | (2H, m), 2.58 (5H, m), 2.07 (2H, m), 1.75-1.85 (4H, m), 1.42-1.48 (3H, m), 1.32 (9H, s) | |
| 4 | NMR (CDCl3) δ 7.36-7.42 (4H, m), 7.30 (1H, d), 7.24 (1H, m), 6.58-6.62 (3H, m), 6.35 (1H, s), 5.02-5.09 (2H, m), 4.75 (2H, s), 4.13-4.20 (2H, m), 4.06 (2H, m), 2.83 (2H, t), 2.60 (2H, m), 2.01 (2H, m), 1.34 (9H, s) | 623.65 (M + 1), 621.67 (M − 1) |
| 5 | δ 8.55 (1H, s), 8.21 (1H, s), 7.52-7.58 (5H, m), 7.41-7.47 (3H, m), 7.21 (1H, d), 7.10 (1H, t), 6.69 (1H, d), 6.34 (1H, s), 4.85-5.00 (4H, m), 3.77-3.90 (7H, m), 2.82 (2H, t), 2.73 (2H, t), 2.01 (2H, m), 1.27 (9H, s) | 661.56 (M + 1) |
| 6 | δ 8.49 (1H, s), 8.18 (1H, s), 7.49 (1H, d), 7.34-7.38 (4H, m), 6.71 (1H, d), 6.32 (1H, s), 4.45-4.70 (2H, m), 4.06 (2H, bs), 3.49 (2H, bs), 3.32 (2H, m, merged with water peak), 3.12 (2H, s), 2.75 (6H, bs), 2.37(3H, s), 1.99 (2H, bs), 1.26 (9H, s), 1.03 (2H, d) | 574.36 (M⁺) |
| 7 | δ 8.55 (1H, s), 8.20 (1H, s), 7.68-7.70 (1H, m), 7.52-7.56 (5H, m), 7.40-7.47 (3H, m), 7.31 (1H, m), 6.67 (1H, d), 6.34 (1H, s), 5.02-4.87 (3H, m), 3.90 (3H, bs), 2.81 (2H, t), 2.73 (2H, t), 2.43 (3H, s), 2.00 (2H, t), 1.27 (9H, s), 1.23 (2H, m) | 675(M − 1), 677.08(M + 1) |
| 8 | δ 10.53 (1H, s), 8.43 (1H, s), 8.18 (1H, s), 7.56 (1H, t), 7.46 (1H, d), 7.41 (2H, d), 7.28 (1H, d), 7.21 (1H, d), 7.07-7.12 (2H, m), 6.69 (1H, d), 6.28 (1H, s), 4.96-5.00 (2H, d), 4.85-4.92 (2H, m), 3.87-3.90 (3H, m), 3.81 (3H, s), 3.77 (1H, m), 2.82 (2H, t), 2.73 (2H, t), 2.01 (2H, t), 1.25 (9H, s) | 709.17(M − 1), 711 (M + 1) |
| 9 | δ 8.45 (1H, s), 8.18 (1H, s), 7.54-7.56 (1H, m), 7.46 (2H, m), 7.37-7.42 (2H, m), 7.26-7.31 (2H, m), 7.08 (1H, d), 6.67 (1H, d), 6.28 (1H, s), 4.87-5.01 (4H, m), 3.75-3.90 (4H, s), 2.81 (2H, t), 2.73 (2H, t), 2.43 (3H, s), 2.00 (2H, t), 1.25 (9H, s) | 725.17 (M − 1) |
| 10 | δ 8.49 (1H, s), 8.19 (1H, s), 7.54-7.56 (1H, m), 7.47 (2H, m), 7.32-7.39 (6H, m), 6.67 (1H, d), 6.32 (1H, s), 4.87-5.01 (4H, m), 3.75-3.90 (4H, m), 2.80 (2H, t), 2.72 (2H, t), 2.43 (3H, s), 2.37 (3H, s), 2.00 (2H, m), 1.26 (9H, s) | 691.25 (M + 1) |
| 11 | δ 8.55 (1H, s), 8.20 (1H, s), 7.52-7.44 (10H, m), 6.68 (1H, m), 6.34 (1H, s), 4.88-5.02 (4H, m), 3.76-3.90 (4H, m), 3.51 (6H, bs), 3.05 (2H, m), 2.81 (2H, t), 2.72 (2H, t), 2.33 (4H, bs), 2.00 (2H, t), 1.27 (9H, s) | 774(M − 1), 776.42(M + 1) |
| 12 | δ 8.50 (1H, s), 8.19 (1H, s), 7.51 (1H, d), 7.39 (2H, d), 7.32 (2H, d), 6.71 (1H, d), 6.33 (1H, s), 4.06 (2H, t), 3.33-3.35 (2H, m), 3.13-3.16 (4H, m), 2.72-2.79 (8H, m), 2.36 (3H, s), 1.97-2.03 (2H, m), 1.27 (9H, s), 0.93 (1H, m), 0.43 (2H, d), 0.18 (2H, d) | 585.48 (M + 1) |
| 13 | δ 8.50 (1H, s), 8.20 (1H, s), 7.50-7.57 (2H, m), 7.45 (1H, d), 7.38-7.40 (3H, m), 7.28-7.34 (3H, m), 6.75 (1H, d), 6.33 (1H, s), 4.15 (2H, t), 3.97 (2H, s), 3.77 (2H, t), 2.98 (4H, bs), 2.79 (2H, t), 2.72 (2H, t), 2.43 (3H, s), 2.37 (3H, s), 2.00 (2H, m), 1.27 (9H, s) | 675.16 (M − 1) |
| 14 | δ 8.50 (1H, s), 8.20 (1H, s), 7.50-7.56 (2H, m), 7.38-7.40 (3H, m), 7.33 (2H, d), 7.20 (1H, d), 7.09 (1H, t), 6.76 (1H, d), 6.33 (1H, s), 4.16 (2H, t), 3.95 (2H, s), 3.82 (3H, s), 3.78 (2H, t), 2.95-2.99 (4H, m), 2.80 (2H, t), 2.73 (2H, t), 2.37 (3H, s), 1.99-2.04 (2H, m), 1.27 (9H, s) | 661.22 (M + 1), 659.15 (M − 1) |
| 15 | δ 10.71 (1H, bs), 8.50 (1H, s), 8.19 (1H, s), 7.50 (1H, d), 7.46 (1H, d), 7.32-7.40 (5H, m), 7.01 (1H, d), 6.94 (1H, t), 6.75 (1H, d), 6.32 (1H, s), 4.16 (2H, t), 4.03 (2H, t), 3.81 (2H, s), 2.98-3.02 (4H, m), 2.80 (2H, t), 2.72 (2H, t), 2.37 (3H, s), 1.98-2.04 (2H, m), 1.26 (9H, s) | 647.03 (M + 1) |
| 16 | δ 8.48 (1H, s), 8.18 (1H, s), 7.49 (1H, d), 7.38 (2H, m), 7.33 (4H, m), 7.27 (1H, d), 7.22 (2H, d), 6.71 (1H, d), 6.32 (1H, s), 4.51 (2H, s), 4.06 (2H, t), 3.23 (2H, s), 3.18 (2H, t), 2.69-2.76 (8H, m), 2.37 (3H, s), 1.98 (2H, m), 1.26 (9H, s) | 621.44 (M + 1) |
| 17 | δ 8.44 (1H, s), 8.17 (1H, s), 7.49 (1H, d), 7.40 (2H, d), 7.07 (2H, d), 6.72 (1H, d), 6.30 (1H, s), 4.07 (2H, m), 3.81 (3H, s), 3.33 (2H, partially merged with water peak), 3.13-3.17 (4H, m), 2.72-2.77 (8H, m), 1.99-2.01 (2H, m), 1.26 (9H, s), 0.93 (1H, m), 0.43 (2H, d), 0.20 (2H, m) | 601.48 (M + 1) |
| 18 | δ 9.77 (1H, s), 8.40 (1H, s), 8.20 (1H, s), 7.50 (1H, d), 7.26 (2H, d), 6.88 (2H, d), 6.72 (1H, d), 6.29 (1H, s), 4.07 (2H, bs), 3.33-3.36 (2H, m, partially merged with water peak), 3.13-3.17 (4H, m), 2.70-2.77 (8H, m), 1.99 (2H, t), 1.25 (9H, s), 0.93 (1H, m), 0.43 (2H, d), 0.19 (2H, d) | 587.43 (M + 1) |
| 19 | NMR (DMSO-d6 + D2O) δ 7.46-7.53 (3H, m), 7.34-7.39 (7H, m), 6.81 (1H, d), 6.33 (1H, s), 4.38 (2H, bs), 4.20 (2H, s), 3.96 (2H, s), 3.73 (4H, m, partially merged with water signal), 2.85-2.90 (2H, m), 2.73 (2H, m), 2.37 (3H, s), 1.99-2.04 (2H, m), 1.27 (9H, s) | 607.46 (M + 1) |
| 20 | δ 8.50 (1H, s), 8.19 (1H, s), 7.70 (1H, m), 7.49-7.51 (2H, d), 7.39 (2H, d), 7.33 (2H, d), 7.20 (1H, d), 7.07 (1H, t), 6.74 (1H, d), 6.32 (1H, s), 4.13-4.14 (4H, m), 3.94 (4H, bs), 3.50 (4H, bs), 2.98 (4H, bs), 2.79 (2H, t), 2.72 (2H, t), 2.58 (2H, t), 2.37 (3H, s), 2.33 (4H, m), 2.00 (2H, m), 1.26 (9H, s) | 760.35 (M⁺) |
| 21 | δ 8.50 (1H, s), 8.19 (1H, s), 7.49 (1H, d), 7.39 (2H, d), 7.33 (2H, d), 6.71 (1H, d), 6.32 (1H, s), 4.07 (2H, bs), 3.27 (2H, t), 3.22 (2H, d), | 613.51 (M + 1) |

TABLE 1-continued

| Comp. No. | $^1$H-NMR (400 MHz, DMSO-$d_6$) | MASS |
|---|---|---|
|  | 3.13 (2H, bs), 2.70-2.77 (8H, m), 2.37 (3H, s), 2.13-2.19 (1H, m), 1.97-2.01 (2H, m), 1.59 (4H, m), 1.47 (2H, m), 1.26 (9H, s), 1.14-1.16 (2H, m) |  |
| 22 | δ 8.49 (1H, s), 8.18 (1H, s), 7.49 (1H, d), 7.38 (2H, d), 7.33 (2H, d), 6.71 (1H, d), 6.32 (1H, s), 4.00-4.07 (2H, m), 3.22 (2H, t), 3.11 (2H, s), 2.70-2.78 (8H, m), 2.37 (3H, s), 1.95-2.01 (5H, m), 1.77-1.85 (2H, m), 1.65-1.71 (2H, m), 1.26 (9H, s), 1.17 (2H, t) | 599.55 (M + 1) |
| 23 | δ 8.53 (1H, s), 8.20 (1H, s), 7.50-7.56 (2H, m), 7.35-7.42 (5H, m), 7.19 (1H, d), 7.08 (1H, t), 6.75 (1H, d), 6.33 (1H, s), 4.16 (2H, t), 3.94 (2H, s), 3.81 (3H, s), 3.77 (2H, t), 2.96 (4H, m), 2.79 (2H, t), 2.64-2.74 (4H, m), 2.00 (2H, m), 1.26 (9H, s), 1.22 (3H, t) | 675.67(M + 1) |
| 24 | δ 10.55 (1H, s), 8.44 (1H, s), 8.17 (1H, s), 7.54 (1H, t), 7.43-7.47 (3H, m), 7.38 (1H, d), 7.26-7.31 (2H, m), 7.08 (1H, d), 6.75 (1H, d), 6.29 (1H, s), 4.15 (2H, t), 3.96 (2H, s), 3.76 (2H, t), 2.98 (4H, m), 2.79 (2H, t), 2.73 (2H, t), 2.50 (3H, s), 1.97-2.03 (2H, m), 1.25 (9H, s) | 713.43 (M$^+$) |
| 25 | δ 10.54 (1H, s), 8.43 (1H, s), 8.17 (1H, s), 7.54 (1H, t), 7.45-7.47 (2H, m), 7.38 (1H, d), 7.28 (1H, m), 7.19 (1H, d), 7.07-7.09 (2H, m), 6.75 (1H, d), 6.29 (1H, s), 4.16 (2H, t), 3.94 (2H, s), 3.81 (3H, s), 3.77 (2H, m), 2.96 (4H, m), 2.80 (2H, t), 2.73 (2H, t), 2.00 (2H, m), 1.25 (9H, s) | 697.34 (M$^+$) |
| 26 | δ 10.71 (1H, bs), 8.44 (1H, s), 8.17 (1H, s), 7.45-7.47 (3H, m), 7.36 (1H, t), 7.28 (1H, dd), 7.08 (1H, d), 7.01 (1H, d), 6.94 (1H, t), 6.75 (1H, d), 6.29 (1H, s), 4.15 (2H, t), 4.02 (2H, t), 3.96 (2H, s), 2.98-3.01 (4H, m), 2.80 (2H, t), 2.73 (2H, t), 2.00 (2H, m), 1.25 (9H, s) | 683.39 (M$^+$) |
| 27 | δ 10.54 (1H, s), 8.43 (1H, s), 8.17 (1H, s), 7.49-7.51 (1H, m), 7.45 (2H, bs), 7.37 (1H, d), 7.27 (1H, d), 7.18 (1H, d), 7.08 (2H, m), 6.75 (1H, d), 6.29 (1H, s), 4.15 (2H, m), 3.95-3.99 (4H, m), 3.80 (2H, t), 2.97 (4H, bs), 2.73-2.79 (4H, m), 1.99 (2H, t), 1.64 (2H, q), 1.25 (9H, s), 0.85 (3H, t) | 725.43(M$^+$) |
| 28 | NMR (DMSO-d6 + D2O) δ 7.39-7.45 (5H, m), 6.75 (1H, d), 6.35 (1H, s), 4.02 (2H, partially merged with water signal), 3.42 (2H, bs), 3.22 (2H, d), 3.06 (2H, s), 2.80-2.82 (2H, t), 2.71-2.75 (4H, m), 2.55-2.59 (2H, partially merged with solvent signal), 2.42 (3H, s), 2.04 (2H, t), 1.91 (2H, t), 1.32 (9H, s), 0.99 (1H, bs), 0.50 (2H, d), 0.26 (2H, d) | 599.59 (M + 1) |
| 29 | δ 8.50 (1H, s), 8.19 (1H, s), 7.63 (1H, d), 7.53 (2H, dd), 7.39 (2H, d), 7.33 (2H, d), 7.00 (1H, t), 6.75 (1H, d), 6.32 (1H, s), 4.22 (2H, t), 4.16 (2H, t), 4.02 (2H, s), 3.06 (2H, t), 3.00 (2H, t), 2.80 (2H, t), 2.72 (2H, t), 2.37 (3H, s), 2.00 (2H, m), 1.26 (9H, s) | 681.53 (M$^+$), 683.51 (M + 2) |
| 30 | δ 8.49 (1H, s), 8.19 (1H, s), 7.50 (2H, d), 7.34-7.40 (5H, m), 7.19 (1H, d), 7.07 (1H, t), 6.75 (1H, d), 6.32 (1H, s), 4.91 (1H, bs), 4.15 (2H, bs), 4.08 (2H, bs), 3.90-3.95 (4H, m), 3.66 (2H, bs), 2.97 (4H, bs), 2.79 (2H, t), 2.72 (2H, t), 2.37 (3H, s), 2.00 (2H, m), 1.26 (9H, s). | 691.22 (M + 1) |
| 31 | δ 10.71(1H, s), 8.50 (1H, s), 8.20 (1H, s), 7.74 (1H, s), 7.53 (2H, dd), 7.36 (4H, dd), 7.09 (1H, d), 6.75 (1H, d), 6.32 (1H, s), 4.11-4.15 (4H, m), 3.94 (2H, s), 2.98-3.00 (4H, m), 2.80 (2H, t), 2.73 (2H, t), 2.37 (3H, s), 1.98-2.02 (2H, m), 1.26 (9H, s) | 681.53 (M$^+$), 679.58 (M − 2) |
| 32 | δ 8.48 (1H, s), 8.18 (1H, s), 7.50 (2H, m), 7.32-7.39 (5H, m), 7.18 (1H, d), 7.08 (1H, t), 6.74 (1H, s), 6.32 (1H, s), 4.15 (2H, t), 4.02 (2H, t), 3.95 (2H, s), 3.80 (2H, t), 2.98 (4H, t), 2.79 (2H, t), 2.72 (2H, t), 2.37 (3H, s), 1.99 (2H, t), 1.61 (2H, t), 1.30 (2H, m), 1.26 (9H, s), 0.83 (3H, t) | 702.84 (M$^+$) |
| 33 | δ 8.49 (1H, s), 8.19 (1H, s), 7.49-7.53 (3H, m), 7.39-7.32 (6H, m), 6.75 (1H, d), 6.32 (1H, s), 4.15 (2H, t), 3.97 (2H, s), 3.75 (2H, t), 2.98 (4H, bs), 2.88 (2H, t), 2.79 (2H, t), 2.72 (2H, t), 2.37 (3H, s), 1.98-2.01(2H, m), 1.49-1.54 (2H, m), 1.26 (9H, s), 0.90 (3H, t) | 705.67 (M + 1) |
| 34 | δ 8.54 (1H, s), 8.23 (1H, s), 7.61 (2H, d), 7.51 (1H, d), 7.39 (2H, d), 7.33 (2H, d), 6.93 (2H, d), 6.76 (1H, d), 6.32 (1H, s), 4.20-4.14 (6H, m), 3.15 (4H, d), 2.81 (2H, t), 2.73 (2H, t), 2.37 (3H, s), 2.01 (2H, m), 1.26 (9H, s) | 647.17 (M$^+$) |
| 35 | δ 8.45 (1H, s), 8.18 (1H, s), 7.52 (2H, m), 7.46 (2H, d), 7.38 (1H, d), 7.31-7.33 (1H, m), 7.27 (1H, dd), 7.07 (1H, d), 6.75 (1H, d), 6.29 (1H, s), 4.15 (2H, t), 3.97 (2H, s), 3.75 (2H, t), 2.98 (4H, bs), 2.88 (2H, t), 2.79 (2H, t), 2.72 (2H, t), 1.99 (2H, m), 1.49-1.54 (2H, m), 1.25 (9H, s), 0.90 (3H, t) | 741.06 (M + 1) |
| 36 | δ 9.73 (1H, s), 8.49 (1H, s), 8.19 (1H, s), 7.51 (1H, d), 7.39 (2H, d), 7.29-7.34 (3H, m), 7.17 (2H, d), 6.89 (1H, d), 6.75 (1H, d), 6.32 (1H, s), 4.16 (2H, t), 4.11 (2H, t), 3.95 (2H, s), 2.98-3.01 (4H, m), 2.80 (2H, t), 2.72 (2H, t), 2.37 (3H, s), 2.00 (2H, t), 1.26 (9H, s) | 647.12 (M + 1) |
| 37 | δ 10.84 (1H, s), 9.79 (1H, s), 8.49 (1H, s), 8.18 (1H, s), 7.50 (1H, d), 7.39 (2H, d), 7.29-7.34 (3H, m), 6.75 (1H, d), 6.42 (1H, s), 6.36 (1H, d), 6.32 (1H, s), 4.15 (2H, t), 4.03 (2H, t), 3.93 (2H, s), 2.97-3.00 (4H, m), 2.80 (2H, t), 2.72 (2H, t), 2.37 (3H, s), 2.00 (2H, m), 1.26 (9H, s) | 663.16 (M + 1) |
| 39 | δ 9.07 (1H, s), 8.59 (1H, s), 8.44 (1H, s), 8.10 (1H, d), 7.61 (1H, d), 6.96 (1H, d), 6.74 (1H, d), 4.08 (2H, t), 3.71 (3H, s), 3.36 (2H, t), 3.16 (2H, d), 3.14 (2H, s), 3.06 (3H, s), 2.75-2.89 (8H, m), 1.98-2.07 | 628.42 (M + 1) |

TABLE 1-continued

| Comp. No. | $^1$H-NMR (400 MHz, DMSO-d$_6$) | MASS |
|---|---|---|
| | (2H, m), 1.24 (9H, s), 0.94 (1H, m), 0.41-0.46 (2H, q), 0.19-0.21 (2H, q) | |
| 40 | δ 9.09 (1H, s), 8.61 (1H, s), 8.46 (1H, s), 8.10 (1H, s), 7.63 (1H, d), 7.46 (1H, d), 7.36 (1H, t), 7.01 (2H, d), 6.92-6.96 (2H, m), 6.77 (1H, d), 4.17 (2H, bs), 4.04 (2H, bs), 3.97 (2H, s), 3.71 (3H, s), 3.06 (3H, s), 3.00 (4H, m), 2.82 (4H, t), 2.04 (2H, m), 1.24 (9H, s) | 690.44 (M + 1) |
| 41 | NMR (DMSO-d6 + D2O) δ 8.06 (1H, s), 7.60 (1H, d), 7.02 (1H, s), 6.77 (1H, d), 4.03 (2H, m), 3.76 (3H, bs, partially merged with water peak), 3.42 (2H, s), 3.22 (2H, d), 3.06 (5H, m), 2.86 (4H, m), 2.71 (2H, bs), 2.57 (2H, partially merged with solvent peak), 2.08 (2H, t), 1.92 (2H, t), 1.28 (9H, s), 0.99 (1H, m), 0.49 (2H, d), 0.24 (2H, d) | 642.64 (M + 1) |
| 42 | δ 9.07 (1H, s), 8.60 (1H, s), 8.45 (1H, s), 8.10 (1H, s), 7.62 (1H, d), 7.52 (2H, d), 7.39-7.32 (2H, m), 6.96 (1H, s), 6.76 (1H, d), 4.16 (2H, bs), 3.98 (2H, s), 3.75 (2H,bs), 3.71 (3H, s), 3.06 (3H, s), 2.99 (4H, bs), 2.88 (2H, t), 2.82 (4H, m), 2.03 (2H, m), 1.49-1.55 (2H, m), 1.24 (9H, s), 0.90 (3H, t) | 748.13 (M + 1) |
| 44 | NMR (DMSO-d6 + D2O) δ 8.06 (1H, s), 7.59 (1H, d), 7.02 (1H, s), 6.80 (1H, d), 4.13 (2H, bs), 3.76 (3H, bs), 3.31 (4H, bs), 3.20 (2H, s), 3.08 (3H, s), 2.83-2.87 (8H, m), 2.04-2.10 (2H, m), 1.48-1.51 (2H, m), 1.29 (11H, m), 0.92 (3H, t) | 630.16 (M + 1) |
| 45 | δ 9.06 (1H, s), 8.60 (1H, s), 8.44 (1H, s), 8.09 (1H, s), 7.63 (1H, d), 7.54 (1H, t), 7.45 (1H, t), 7.38 (1H, d), 7.29 (1H, t), 6.96 (1H, s), 6.76 (1H, d), 4.16 (2H, t), 3.97 (2H, s), 3.76 (2H, t), 3.71 (3H,s), 3.13 (2H, q), 2.99 (4H, bs), 2.82 (4H, bs), 2.42 (3H, s), 1.99-2.05 (2H, m), 1.28 (3H, t), 1.23 (9H, s) | 734.20 (M$^+$) |
| 46 | δ 9.75 (1H, s), 9.08 (1H, s), 8.61 (1H, s), 8.47 (1H, s), 8.10 (1H, s), 7.63 (1H, d), 7.31 (1H, t), 7.17 (2H, s), 6.96 (1H, s), 6.90 (1H, d), 6.77 (1H, d), 4.17- 4.12 (4H, m), 3.97 (2H, s), 3.71 (3H, s), 3.06 (3H, s), 3.01 (4H, m), 2.83 (4H, m), 2.04 (2H, t), 1.26 (9H, s) | 690.12 (M + 1) |
| 47 | δ 9.08 (1H, s), 8.60 (1H, s), 8.45 (1H, s), 8.10 (1H, s), 7.71 (2H, d), 7.63 (1H, d), 7.45 (2H, d), 6.96 (1H, s), 6.77 (1H, d), 5.00 (1H, bs), 4.14-4.17 (4H, m), 3.97 (2H, s), 3.71 (3H, s), 3.61 (2H, bs), 3.11 (2H, t), 3.06 (3H, s), 3.02 (4H, m), 2.82 (4H, m), 2.08 (2H, m), 1.24 (9H, s) | 750.27 (M + 1) |
| 48 | δ 10.90 (1H, s), 9.08 (1H, s), 8.60 (1H, s), 8.45 (1H, s), 8.10 (1H, s), 7.62 (1H, d), 7.40-7.44 (2H, m), 7.03 (1H, d), 6.96 (1H, s), 6.77 (1H, d), 4.17 (2H, bs), 4.01 (2H, bs), 3.97 (2H, s), 3.71 (3H, s), 3.06 (3H, s), 3.00 (4H, m), 2.82 (4H, t), 2.04 (2H, m), 1.24 (9H, s) | 724.20 (M$^+$) |
| 49 | δ 9.87 (1H, s), 9.05 (1H, s), 8.60 (1H, s), 8.46 (1H, s), 8.08 (1H, s), 7.62 (1H, d), 7.31 (1H, d), 6.95 (1H, d), 6.77 (1H, d), 6.44 (1H, s), 6.38 (1H, dd), 4.18 (2H, t), 4.06 (2H, t), 4.01 (2H, bs), 3.71 (3H, s), 3.13 (2H, q), 3.02-3.06 (4H, m), 2.83 (4H, t), 2.04 (2H, m), 1.28 (3H, t), 1.23 (9H, s) | 720.19 (M + 1) |
| 50 | δ 9.05 (1H, bs), 8.60 (1H, s), 8.45 (1H, s), 8.09 (1H, s), 7.62 (1H, d), 7.52 (2H, d), 7.38 (1H, d), 7.30-7.33 (1H, m), 6.95 (1H, s), 6.76 (1H, d), 4.16 (2H, t), 3.98 (2H, s), 3.75 (2H, t), 3.71 (3H, s), 3.13 (2H, q), 2.99 (4H, bs), 2.88 (2H, t), 2.81-2.82 (4H, m), 2.03 (2H, t), 1.49-1.55 (2H, m), 1.28 (3H, t), 1.23 (9H, s), 0.90 (3H, t) | 762.05 (M + 1) |
| 51 | δ 10.91 (1H, bs), 9.06 (1H, bs), 8.59 (1H, s), 8.44 (1H, s), 8.08 (1H, s), 7.62 (1H, d), 7.40-7.43 (2H, m), 7.03 (1H, d), 6.95 (1H, s), 6.77 (1H, d), 4.17 (2H, bs), 4.02 (2H, bs), 3.97 (2H, s), 3.71 (3H, s), 3.13 (2H, q), 3.00 (4H, m), 2.82 (4H, t), 2.04 (2H, m), 1.28 (3H, t), 1.23 (9H, s) | 738.08 (M$^+$) |
| 53 | δ (CDCl3) 7.41 (1H, m), 7.29-7.34 (1H, m), 7.08-7.13 (1H, m), 6.88 (1H, d), 6.49-6.51 (1H, m), 6.31(1H, s), 5.05 (1H, s), 4.91(1H, s), 4.72 (2H, m), 4.13-4.22 (2H, m), 4.04 (2H, m), 3.83 (3H, s), 2.77 (2H, t), 2.52-2.54 (2H, m), 1.94-1.95 (2H, m), 1.29 (9H, s), | 687.62 (M+) |
| 54 | δ (CDCl3) 11.42-11.48 (1H, m), 7.29 (2H, m), 7.21-7.23 (1H, m), 7.16 (2H, m), 6.45-6.51 (1H, m), 6.39 (1H, d), 4.68 (2H, s), 4.59-4.61 (2H, m), 4.33-4.38 (2H, q), 3.73-3.76 (2H, m), 2.85-2.98 (4H, m), 2.46-2.54 (2H, m), 2.34 (3H, s), 1.93-1.97 (2H, m), 1.68 (1H, m), 1.37-1.42 (3H, m), 1.33 (9H, s), 1.16 (2H, m), .0.95-.0.97 (2H, m), | 739.59 (M + 1) |
| 55 | δ 11.03 (1H, s), 8.56 (1H, s), 8.20 (1H, s), 7.36-7.44 (4H, m), 6.66 (1H, m), 6.37 (1H, s), 6.32 (1H, s), 4.82-4.89 (2H, m), 4.43-4.50 (2H, m), 3.73 (2H, bs), 2.57-2.82 (8H, m), 2.02 (6H, m), 1.80-1.82 (4H, m), 1.37-1.46 (4H, m), 1.25 (9H, s) | 709.65 (M + 1) |
| 56 | δ (CDCl3) 7.45 (1H, s), 7.26 (1H, m, merged with solvent peak), 6.65 (1H, m), 6.40 (1H, m), 6.35 (1H, s), 5.05-5.12 (2H, m), 4.78 (2H, s), 4.15 (2H, m), 4.09 (2H, m), 2.85 (2H, t), 2.66 (2H, m), 2.38 (3H, s), 2.04 (2H, m), 1.33 (9H, s), | 671.57 (M + 1) |
| 57 | δ (CDCl3) 7.60-7.61 (2H, m), 7.50 (3H, m), 7.29 (1H, m), 7.15 (2H, d), 6.84-6.90 (2H, m), 6.61 (1H, m), 6.33 (1H, s), 4.98-5.08 (2H, m), 4.76-4.79 (2H, m), 4.03-4.13 (2H, m), 3.97-3.98 (2H, m), 2.84 (2H, t), 2.54-2.65 (2H, m), 2.32 (3H, s), 1.93-1.96 (2H, m), 1.33 (9H, s) | 643.61 (M − 1) |
| 58 | δ 8.55 (1H, s), 8.20 (1H, s), 7.79 (1H, s), 7.68 (1H, m), 7.53-7.52 (4H, m), 7.45 (1H, d), 7.40 (1H, m), 7.32-7.34 (1H, m), 6.70 (1H, d), 6.34 (1H, s), 5.00 (1H, s), 4.95 (2H, s), 4.86 (1H, s), 4.25 (1H, bs), | 695.17 (M+) |

TABLE 1-continued

| Comp. No. | $^1$H-NMR (400 MHz, DMSO-d$_6$) | MASS |
|---|---|---|
| | 4.10 (1H, bs), 3.92-3.93 (5H, m), 2.82-2.84 (2H, m), 2.73 (2H, m), 2.01 (2H, m), 1.27 (9H, s) | |
| 59 | δ 8.49 (1H, s), 8.18 (1H, s), 7.49 (1H, d), 7.32-7.39 (4H, dd), 6.71 (1H, d), 6.32 (1H, s), 4.06 (2H, t), 3.20-3.26 (4H, m), 3.12 (2H, s), 2.70-2.76 (8H, m), 2.37 (3H, s), 1.99 (2H, m), 1.44-1.50 (2H, m), 1.26 (9H, s), 0.81 (3H, t) | 573.42 (M + 1) |
| 60 | δ 8.51 (1H, s), 8.14 (1H, s), 7.53-7.57 (2H, m), 7.46 (1H, d), 7.36 (2H, t), 6.71 (1H, d), 6.32 (1H, s), 4.07 (2H, t), 3.35 (2H, m, merged with water signal), 3.16 (2H, d), 3.13 (2H, s), 2.63-2.79 (8H, m), 1.99 (2H, m), 1.24 (9H, s), 0.93 (1H, m), 0.43 (2H, d), 0.19 (2H, m). | 589.45 (M + 1) |
| 61 | δ 8.54 (1H, s), 8.18 (1H, s), 7.47-7.53 (5H, m), 7.31 (1H, m), 6.72 (1H, m), 6.34 (1H, s), 4.07 (2H, t), 3.33 (2H, merged with water signal), 3.13-3.17 (4H, m), 2.70-2.79 (8H, m), 1.97-2.01 (2H, m), 1.27 (9H, s), 0.93 (1H, m), 0.43 (2H, d), 0.20 (2H, d) | 571.43 (M + 1) |
| 62 | δ 8.28 (1H, s), 8.13 (1H, s), 7.48 (1H, d), 7.32-7.37 (2H, m), 6.71 (1H, d), 6.32 (1H, s), 4.02-4.06 (2H, m), 3.33 (2H, merged with water signal), 3.13-3.17 (4H, m), 2.76 (6H, m), 2.68 (2H, t), 2.02 (3H, s), 1.95-1.99 (2H, m), 1.25 (9H, s), 0.93 (1H, m), 0.43 (2H, d), 0.19 (2H, d) | 583.45 (M − 1) |
| 63 | δ 10.83 (1H, s), 10.54 (1H, s), 9.79 (1H, s), 8.44 (1H, s), 8.18 (1H, s), 7.45 (1H, m), 7.27-7.31 (2H, m), 7.08 (1H, d), 6.75(1H, d), 6.42 (1H, s), 6.36 (1H, d), 6.29 (1H, s), 4.15 (2H, t), 4.03 (2H, s), 3.93 (2H, s), 2.97-3.00 (4H, m), 2.80 (2H, t), 2.73 (2H, t), 2.00 (2H, m), 1.25 (9H, s) | 699.15 (M+) |
| 64 | δ 9.50 (1H, s), 8.48 (2H, d), 8.01 (1H, s), 7.59 (2H, d), 6.74 (1H, d), 4.08 (2H, t), 3.68 (3H, s), 3.16 (4H, t), 2.80-2.83 (10H, m), 2.54 (3H, partially merged with solvent peak), 2.03-2.05 (4H, m), 1.22 (9H, s), 0.94 (1H, m), 0.43 (2H, m), 0.19 (2H, m) | 618.21 (M + 1) |
| 65 | δ 10.54 (1H, s), 8.43 (1H, s), 8.16 (1H, s), 7.44-7.46 (2H, m), 7.27 (1H, d), 7.08 (1H, d), 6.74 (1H, d), 6.29 (1H, s), 4.13(2H, t), 3.91 (2H, t), 3.82 (2H, s), 2.93--2.97 (4H, m), 2.67-2.80 (5H, m), 1.99 (2H, m), 1.86 (2H, d), 1.77 (2H, d), 1.66-1.69 (1H, m), 1.48 (2H, q), 1.33-1.35 (3H, m), 1.23 (9H, s) | 673.11(M+) |
| 66 | δ 8.83 (1H, s), 8.38 (1H, s), 7.44(1H, s), 7.38 (2H, d), 7.30 (2H, d), 7.19 (1H, s), 7.13 (1H, m), 6.67 (1H, m), 6.32 (1H, s), 4.02 (2H, s), 3.94 (2H, s), 3.86 (2H, s), 2.85-2.93 (6H, m), 2.63 (2H, m), 2.35 (3H, s), 2.15 (3H, s), 1.95 (2H, t), 1.26 (9H, s) | 695.05 (M+) |
| 67 | δ 8.55 (1H, s), 8.23 (1H, s), 8.12(1H, s), 8.05 (1H, d), 7.86 (1H, d), 7.73 (1H, d), 7.63-7.74 (1H, t), 7.55-7.60 (2H, m), 7.58 (1H, d), 7.40(2H, d), 7.32 (2H, d), 6.75 (1H, d), 6.32 (1H, s), 4.16 (2H, t), 4.04 (2H, s), 3.80 (2H, t), 2.99-3.00 (4H, m), 2.79 (2H, t), 2.72 (2H, t), 2.29 (3H, s), 1.99 (2H, t), 1.26 (9H, s). | 681.17 (M + 1) |
| 68 | δ 8.50 (1H, s), 8.19 (1H, s), 7.50 (1H, d), 7.39 (2H, d), 7.32 (2H, d), 6.73 (1H, d), 6.32 (1H, s), 4.13(2H, t), 3.91 (2H, t), 3.81 (2H, s), 3.60 (3H, m), 2.93--2.97 (4H, m), 2.67-2.80 (5H, m), 2.37 (3H, s), 1.99 (2H, quintet), 1.86 (2H, d), 1.67 (1H, d), 1.42-1.50 (2H, m), 1.32-1.38 (2H, m), 1.26 (9H, s) | 637.19 (M + 1) |
| 69 | δ 8.49 (1H, s), 8.19 (1H, s), 7.74(1H, m), 7.62 (1H, d), 7.51 (1H, d), 7.32-7.44 (6H, m), 6.76 (1H, d), 6.32 (1H, s), 4.36 (2H, t), 4.17(2H, t), 4.00 (2H, s), 3.09 (2H, t), 3.00 (2H, t), 2.81 (2H, t), 2.73 (2H, t), 2.55 (3H, s), 2.37 (3H, s), 2.00 (2H, t), 1.26 (9H, s). | 683.37 (M − 1) |
| 70 | δ 8.51 (1H, s), 8.25 (1H, s), 7.49 (1H, d), 6.79 (2H, s), 6.72 (1H, d), 6.35 (1H, s), 4.07 (2H, t), 3.81 (6H, s), 3.71 (3H, s), 3.35 (2H, merged with water signal), 3.16 (2H, d), 3.13 (2H, s), 2.70-2.79 (8H, m), 1.99 (2H, m), 1.27 (9H, s), 0.93 (1H, m), 0.41-0.45 (2H, q), 0.14-0.21 (2H, q). | 661.20 (M + 1) |
| 71 | δ 10.33 (1H, s), 8.56 (1H, s), 8.27 (1H, s), 7.55 (1H, d), 7.40 (2H, d), 7.33 (1H, d), 6.78 (1H, d), 6.33 (1H, s), 4.33 (2H, bs), 4.04 (2H, bs), 3.58-3.63 (4H, m), 2.83 (2H, t), 2.74 (2H, t), 2.37 (3H, s), 2.36 (7H, s), 2.02 (2H, t), 1.27 (9H, s), 0.97 (1H, m), 0.47 (2H, d), 0.24 (2H, d). | 584.97 (M+) |
| 72 | δ 9.08 (1H, s), 8.60 (1H, s), 8.45 (1H, s), 8.10 (1H, s), 7.62 (1H, d), 6.96 (1H, d), 6.75 (1H, d), 4.14 (2H, t), 3.92 (2H, t), 3.83 (2H, s), 3.71(3H, s), 3.06 (3H, s), 2.94-2.98 (4H, m), 2.81-2.82 (4H, q), 2.70 (1H, m), 2.03 (2H, m), 1.86 (2H, d), 1.78 (2H, d), 1.65 (1H, m), 1.45-1.51 (2H, q), 1.28-1.35 (3H, m), 1.24 (9H, s). | 680.10 (M + 1) |
| 73 | δ 10.9 (1H, s), 9.10 (1H, s), 8.65(1H, s), 8.45 (1H, s), 8.09 (1H, s), 7.56 (1H, s), 7.41-7.44 (2H, m), 7.03 (1H, d), 6.96 (1H, s), 3.96-4.02 (6H, m), 3.71 (3H, s), 3.06 (3H, s), 3.00 (2H, t), 2.91-2.94 (4H, m), 2.78 (2H, t), 2.20 (3H, s), 2.04 (2H, m), 1.24 (9H, s). | 737.96 (M+) |
| 74 | δ 9.07 (1H, s), 8.60 (1H, s), 8.45(1H, s), 8.10-8.14 (2H, m), 8.05 (1H, d), 7.86 (1H, d), 7.74 (1H, d), 7.59-7.67 (4H, m), 6.96 (1H, s), 6.77(1H, d), 4.18 (2H, t), 4.05 (2H, t), 3.81 (2H, t), 3.71 (3H, s), 3.06 (3H, s), 3.02 (4H, m), 2.82 (4H, t), 2.03 (2H, t), 1.24 (9H, s). | 724.07 (M + 1) |

Pharmaceutical Compositions

In another embodiment present invention provides a pharmaceutical composition comprising a therapeutically effective amount of one or more of a compound of formula (I). While it is possible to administer therapeutically effective quantity of compounds of formula (I) either individually or in combination, directly without any formulation, it is common practice to administer the compounds in the form of pharmaceutical dosage forms comprising pharmaceutically acceptable excipient(s)/adjuvant(s)/carrier(s) and at least one active ingredient. These dosage forms may be administered by a variety of routes including oral, topical, transdermal, subcutaneous, intramuscular, intravenous, intraperitoneal, intranasal, pulmonary etc.

Oral compositions may be in the form of solid or liquid dosage form. Solid dosage form may comprise pellets, pouches, sachets or discrete units such as tablets, multiparticulate units, capsules (soft & hard gelatin) etc. Liquid dosage forms may be in the form of elixirs, suspensions, emulsions, solutions, syrups etc. Composition intended for oral use may be prepared according to any method known in the art for the manufacture of the composition and such pharmaceutical compositions may contain in addition to active ingredients, excipients such as diluents, disintegrating agents, binders, solubilizers, lubricants, glidants, surfactants, suspending agents, emulsifiers, chelating agents, stabilizers, flavours, sweeteners, colours etc. Some example of suitable excipients include lactose, cellulose and its derivatives such as microcrystalline cellulose, methylcellulose, hydroxy propyl methyl cellulose & ethylcellulose, dicalcium phosphate, mannitol, starch, gelatin, polyvinyl pyrrolidone, various gums like acacia, tragacanth, xanthan, alginates & its derivatives, sorbitol, dextrose, xylitol, magnesium stearate, talc, colloidal silicon dioxide, mineral oil, glyceryl mono stearate, glyceryl behenate, sodium starch glycolate, cross povidone, crosslinked carboxymethylcellulose, various emulsifiers such as polyethylene glycol, sorbitol, fatty acid esters, polyethylene glycol alkylethers, sugar esters, polyoxyethylene polyoxypropyl block copolymers, polysorbate, polyethoxylated fatty acid monoesters, diesters and mixtures thereof.

Intranasal or pulmonary compositions according to present invention can be in the form of liquid or solid or semisolid composition suitable for nasal administration. Liquid composition can be aqueous, non-aqueous composition, suspension or emulsion; solid composition can be in the form of powder and the like and semi solid composition can be in form of gel and the like. Nasal/pulmonary compositions may also form in-situ gel. Said nasal or pulmonary composition comprises compounds of formula (I) optionally with one or more suitable excipients selected from in-situ gelling agent, mucoadhesive agent, polymer, humectant, buffering agent, stabilizer, surfactant, preservative, thickening agent, solvents, co-solvents, permeation enhancer, chelating agent, viscosity modifying agent, sweetener, taste masking agent, solubilizer, flavoring agent, emulsifier and isotonicity agent.

Sterile compositions for injection can be formulated according to conventional pharmaceutical practice by dissolving or suspending the active substance in a vehicle such as water for injection, N-Methyl-2-Pyrrolidone, propylene glycol and other glycols, alcohols, a naturally occurring vegetable oil like sesame oil, coconut oil, peanut oil, cotton seed oil or a synthetic fatty vehicle like ethyl oleate or the like. Buffers, anti-oxidants, preservatives, complexing agents like cellulose derivatives, peptides, polypeptides and cyclodextrins and the like can be incorporated as required.

The dosage form can have a slow, delayed or controlled release of active ingredients in addition to immediate release dosage forms.

The amount of active ingredient which is required to achieve a therapeutic effect will, of course, vary with the particular compound, the route of administration, the subject under treatment, and the particular disorder or disease being treated. The compounds of the invention may be administered by oral, inhalation or parenteral route at a dose of from 0.0005 to 100 mg/kg per day, preferably from 0.0005 to 50 mg/kg per day, more preferably from 0.001 to 20 mg/kg per day, most preferably from 0.001 to 10 mg/kg per day. The dose range for adult humans is generally from 5 μg to 5 g per day, preferably dose range is 10 μg to 2 g per day.

Dosage forms of presentation provided in discrete units may conveniently contain an amount of compound of the invention which is effective at such dosage or as a multiple of the same, for example units containing 5 μg to 1000 mg.

In another embodiment present invention provides method of treating allergic and non-allergic airway disease by administering a therapeutically effective amount of a compound of formula (I) to a mammal, including human being, in need thereof. Allergic and non-allergic airway diseases include allergic and non-allergic asthma, chronic obstructive pulmonary disease (COPD), rhinitis, chronic bronchitis, emphysema, or asthma-like syndrome such as coughing, wheezing or dyspnea.

In a preferred embodiment present invention provides a method for treating chronic obstructive pulmonary disease and asthma by administering a therapeutically effective amount of a compound of formula (I) to a mammal, including human being, in need thereof.

In a most preferred embodiment present invention provides a method for treating chronic obstructive pulmonary disease by administering a therapeutically effective amount of a compound of formula (I) to a mammal, including human being, in need thereof.

In another embodiment present invention provides the use of a compound of formula (I) for the preparation of a medicament for treating allergic and non-allergic airway disease.

In a preferred embodiment present invention provides the use of a compound of formula (I) for the preparation of a medicament for treating chronic obstructive pulmonary disease and asthma.

In a most preferred embodiment present invention provides the use of a compound of formula (I) for the preparation of a medicament for treating chronic obstructive pulmonary disease.

Biological Testing

Biological Example 1: In-Vitro Studies

Inhibition of p38 Alpha MAPK Activity: Time-Resolved Fluorescence Resonance Energy Transfer Kinase Standard Assay (TR-FRET Assay)

Compounds of present invention at various concentrations were premixed with DMSO. The experiment was initiated by mixing 0.5%-1.0% DMSO as vehicle/compounds with purified recombinant human p38 alpha MAPK (Millipore, USA) in the wells and 15 min incubation at room temperature. Thereafter, 30 nM of Biotinylated GST-ATF2 (Activation transcription Factor2) and 100 μM of ATP were added in to the wells containing reaction mixture, followed by reincubation for 60 minutes at RT. Reaction was terminated by addition of 10 mM of EDTA and detection reagent containing anti-phosphotheronine ATF2 antibody (PerkinElmer®, USA) labeled with europium chelate and APC (Allophycocyanin) labeled streptavidin, into the reaction mixture which was further incubated for 60 minutes at room temperature. The degree of phosphorylation of the substrate (GST-ATF2) was measured using Envision multimode reader (PerkinElmer®). Percentage inhibition of p38 kinase activity was calculated by determining ratio of specific europium 665 nm energy transfer signal to reference 615 nm signal. Results are summarized in the table 2.

Table 2

TABLE 2

| Compound No | Concentration | P38α Inhibition |
|---|---|---|
| 1 | 1 µM | +++++ |
| 2 | 1 µM | ++ |
| 3 | 1 µM | ++ |
| 4 | 1 µM | ++++ |
| 5 | 1 µM | +++++ |
| 6 | 1 µM | +++++ |
| 7 | 1 µM | +++++ |
| 8 | 1 µM | +++++ |
| 9 | 1 µM | +++++ |
| 10 | 1 µM | +++++ |
| 11 | 1 µM | +++++ |
| 12 | 1 µM | +++++ |
| 13 | 1 µM | +++++ |
| 14 | 1 µM | +++++ |
| 15 | 1 µM | +++++ |
| 16 | 1 µM | +++++ |
| 17 | 1 µM | ++++ |
| 18 | 1 µM | +++++ |
| 19 | 1 µM | +++++ |
| 20 | 1 µM | +++++ |
| 21 | 1 µM | +++++ |
| 22 | 1 µM | +++++ |
| 23 | 1 µM | +++++ |
| 24 | 1 µM | +++++ |
| 25 | 1 µM | +++++ |
| 26 | 1 µM | +++++ |
| 27 | 1 µM | +++++ |
| 28 | 1 µM | +++++ |
| 29 | 1 µM | +++++ |
| 30 | 1 µM | +++++ |
| 31 | 1 µM | +++++ |
| 32 | 1 µM | +++++ |
| 33 | 1 µM | +++++ |
| 34 | 1 µM | +++++ |
| 35 | 1 µM | +++++ |
| 36 | 1 µM | +++++ |
| 37 | 1 µM | +++++ |
| 38 | 1 µM | +++++ |
| 39 | 1 µM | +++++ |
| 40 | 1 µM | +++++ |
| 41 | 1 µM | ++++ |
| 42 | 1 µM | +++++ |
| 43 | 1 µM | +++++ |
| 44 | 1 µM | +++++ |
| 45 | 100 nM | +++++ |
| 46 | 100 nM | ++++ |
| 47 | 100 nM | ++++ |
| 48 | 1 µM | +++++ |
| 49 | 1 µM | +++++ |
| 50 | 1 µM | +++++ |
| 51 | 1 µM | +++++ |
| 52 | 1 µM | ++++ |
| 53 | 1 µM | +++ |
| 54 | 1 µM | + |
| 55 | 1 µM | + |
| 56 | 1 µM | +++ |
| 57 | 1 µM | ++++ |
| 58 | 1 µM | +++ |
| 59 | 1 µM | ++++ |
| 60 | 1 µM | ++++ |
| 61 | 1 µM | ++++ |
| 62 | 1 µM | +++ |
| 63 | 100 nM | ++++ |
| 64 | 1 µM | ++ |
| 65 | 1 µM | ++ |
| 66 | 1 µM | + |
| 67 | 1 µM | ++++ |
| 68 | 1 µM | +++ |
| 69 | 1 µM | +++ |
| 70 | 1 µM | +++ |
| 72 | 1 µM | +++ |
| 73 | 1 µM | +++ |
| 74 | 1 µM | ++++ |

Criteria:
+++++ = Inhibition ≥80% ≥ 100%;
++++ = Inhibition ≥60% < 80%;
+++ = Inhibition ≥40% < 60%;
++ = Inhibition ≥20% < 40%

Observation: in-vitro data shows that compounds of present invention effectively inhibits p38 MAP kinase activity.

Biological Example 2: In-Vivo Studies

In vivo efficacy evaluation of compounds in animal model of airway inflammation: The tobacco smoke induced airway inflammation model is used for in-vivo efficacy of compound. Many investigators have used acute tobacco smoke (TS) exposure in rodents as models of airway inflammation for quick screening of anti-inflammatory therapies (*J Pharmacol Exp Ther.* 2008; 324(3):921-9; *J Pharmacol Exp Ther.* 2010; 332(3):764-75; *Journal of Inflammation* 2013, 10(Suppl 1):31 and *Eur Respir J Suppl* 2006; 663s:3850).

Given its position as predominant cause of COPD, animal models using TS exposure would appear to be the logical choice for investigation (*Respir Res.* 2004; 2; 5:18).

A: Efficacy Studies in Acute Mouse Model of Airway Inflammation

Mice were exposed to tobacco smoke (TS) in an acrylic chamber. Animals were exposed to TS from 8, 12, 16 cigarettes on day 1, day 2, day 3 respectively. From day 4 onwards till day 11, animals were exposed to TS from 20 cigarettes per day. Like human COPD associated inflammation, acute exposure of mice to TS induced significant inflammatory cell, predominantly neutrophil recruitment to lungs as compared to air exposed control mice (BALF neutrophil levels, nil in air control group vs 178±29.1*10$^3$ cells/animal in smoke exposed vehicle group).

Lung delivery of test compound was achieved by whole body aerosol exposure for 25 minutes in a chamber. Mice were divided in different dose groups and exposed in a chamber for 25 minutes with vehicle or Compound 12 (0.3 mg/ml) or Compound 12 (3 mg/ml). A total quantity of 3.5 ml of either vehicle or test compound formulation was nebulized in a chambers to respective groups over 25 mins period. Test compounds were administered 2 hr prior to TS exposure from day 6 to day 11. Bronchoalveolar lavage (BAL) was performed 24 hr post last TS exposure.

Trachea of animal was cannulated using catheter. Phosphate Buffer Saline (PBS) was used as lavage fluid. A volume of 0.5 ml was gently instilled and withdrawn and collected in microcentrifuge tube placed on ice. This procedure was repeated further 2 times.

Lavage fluid was separated from cells by centrifugation and supernatant separated. The cell pallet was resuspended in known volume of PBS. Cells in aliquot were stained using Turk solution and total cell numbers were calculated by counting Turk stained aliquot under microscope using haemocytometer.

The residual cell suspension was resuspended and slides prepared using cyto centrifuge technique (Cytospin 4, Thermo Shandon). The slides were then fixed with methanol, air dried and stained with May Grunwald Giemsa stain. Up to 300 cells were counted and differentiated using standard morphometric techniques under light microscopy.

All results are presented at individual data for each animal and mean value calculated for each group. Percentage inhibition for the neutrophil was calculated for Compound 12 treatment group against vehicle group. Results are summarized herein below:

The effect of treatment Compound 12 on cigarette smoke induced Neutrophil accumulation in BAL Fluid.

TABLE 3

| Treatment | Formulation strength | Exposure Duration (Minutes) | Neutrophil ($*10^3$ cells/animal) | % Inhibition |
|---|---|---|---|---|
| Vehicle | NA | 25 | 178 ± 29.1 | — |
| Compound 12 | 0.3 mg/ml | 25 | 107 ± 18.5 | 40 |
| Compound 12 | 3 mg/ml | 25 | 69.6 ± 11.1 | 61 |

Values are Mean ± SEM;
NA: Not applicable

Observation: It was observed that compound of present invention was found effective in inhibition of neutophil influx, an index of pulmonary inflammation. These results indicate that compounds of present invention possess pulmonary anti-inflammatory activity.

B. (I) Efficacy Studies in Acute Guinea Pig Model of Airway Inflammation

Guinea pigs were exposed to tobacco smoke (TS) in an acrylic chamber. Animals were exposed to TS from 5, 10, 15 cigarettes on day 1, day 2, day 3 respectively. From day 4 onwards till day 11, animals were exposed to TS from 15 cigarettes per day. On 11 days of exposure of guinea pig to TS, significant inflammatory cell recruitment, predominantly neutrophils, to lungs was observed as compared to air exposed control guinea pig (BALF neutrophil levels, $0.23\pm0.052*10^6$ cells/animal in air control group vs $1.9\pm0.42*10^6$ cells/animal in smoke exposed vehicle group).

Lung delivery of test compound was achieved by whole body aerosol exposure for 75 minutes in a chamber. Guinea pig were divided in different dose groups and exposed in a chamber for 75 minutes with vehicle or Compound No 43 (6 mg/ml). A total quantity of 7.0 ml of either vehicle or test compound formulation (suspension formulation with D90<5μ, with Malvern Mastersizer®) was nebulized in chambers to respective groups over 75 mins period. Test compound was administered 2 hr prior to TS exposure from day 6 to day 11. Bronchoalveolar lavage (BAL) was performed 24 hr post last TS exposure.

Trachea of animal was cannulated using catheter. Phosphate Buffer Saline (PBS) was used as lavage fluid. A volume of 5.0 ml was gently instilled and withdrawn and collected in microcentrifuge tube placed on ice. This procedure was repeated further 5 times.

Lavage fluid was separated from cells by centrifugation and supernatant separated. The cell pallet was resuspended in known volume of PBS. Cells in aliquot were stained using Turk solution and total cell numbers were calculated by counting Turk stained aliquot under microscope using haemocytometer.

The residual cell suspension was resuspended and slides prepared using cyto centrifuge technique (Cytospin 4, Thermo Shandon). The slides were then fixed with methanol, air dried and stained with May Grunwald Giemsa stain. Up to 300 cells were counted and differentiated using standard morphometric techniques under light microscopy. All results are presented at individual data for each animal and mean value calculated for each group. Percentage inhibition for the neutrophil was calculated for compound no 43 treatment group against vehicle group. Results are summarized herein below:

The effect of treatment compound no 43 on cigarette smoke induced inflammatory cell accumulation in BAL Fluid.

TABLE 4

| Treatment | Concentration | Exposure Duration (Minutes) | Effect on inflammatory cell influx Neutrophil ($*10^6$ cells) | % inhib" |
|---|---|---|---|---|
| Vehicle | NA | 75 | 1.9 ± 0.42 | |
| Compound no 43 | 6 mg/ml | 75 | 0.8 ± 0.20 | 57 |

Values are Mean ± SEM;
NA: Not applicable

Observation: It was observed that compound of present invention was found effective in inhibition of neutrophil influx, an index of pulmonary inflammation in guinea pig model of airway inflammation. These results indicate that compounds of present invention possess pulmonary anti-inflammatory activity.

(II) Efficacy Studies in Chronic Model of COPD in Guinea Pigs.

Guinea pigs were exposed to tobacco smoke (TS) and Lipopolysaccharide (LPS) in an acrylic chamber. Exposure to TS and LPS is given in following manner in a week for a total of 18 weeks.

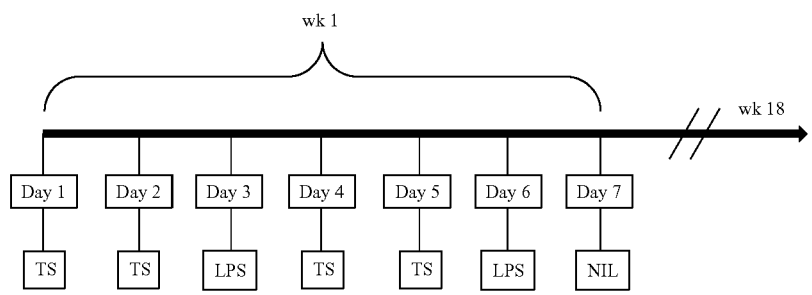

Lung delivery of test material was achieved by whole body aerosol exposure for 50 minutes in a chamber. Guinea pig were divided in different dose groups and exposed to either vehicle or compound no 43 (3 mg/ml). A total quantity of 7.0 ml of either vehicle or compound no 43 (suspension formulation with D90<5μ, with Malvern Mastersizer®) was nebulized in chambers to respective groups over 50 mins period. Compound no 43 or vehicle was administered 2 hr prior to TS/LPS exposure once daily from week 9 to week 18. Control animals were exposed to room air instead of TS and PBS instead of LPS. Lung function and bronchoalveolar lavage (BAL) for each animal was performed 24 hr post last TS exposure.

Lung function assessment in anesthetized and tracheotomized animal was carried out using PFT maneuvers (BUXCO, USA) for determination of various parameters such as Functional Residual Capacity (FRC), Residual volume (RV), Pressure volume and flow volume relationships.

Trachea of animal was cannulated using catheter. Phosphate Buffer Saline (PBS) was used as lavage fluid. A volume of 5.0 ml was gently instilled and withdrawn and collected in microcentrifuge tube placed on ice. This procedure was repeated further 5 times.

Lavage fluid was separated from cells by centrifugation and supernatant separated. The cell pallet was resuspended in known volume of PBS. Cells in aliquot were stained using Turk solution and total cell numbers were calculated by counting Turk stained aliquot under microscope using haemocytometer.

The residual cell suspension was resuspended and slides prepared using cyto centrifuge technique (Cytospin 4, Thermo Shandon). The slides were then fixed with methanol, air dried and stained with May Grunwald Giemsa stain. Up to 300 cells were counted and differentiated using standard morphometric techniques under light microscopy.

All results are presented at individual data for each animal and mean value calculated for each group. Percentage inhibition for the neutrophil was calculated for compound no 43 treatment group against vehicle group. Results are summarized herein below:

A. Effect of treatment of compound no 43, on BALF fluid inflammatory cell influx in guinea pigs.

TABLE 5

| Treatment | Concentration (mg/ml) | Exposure Duration (Minutes) | Neutrophil (*10⁶cells) | % inhib" |
|---|---|---|---|---|
| Air | NA | NA | 0.47 ± 0.10 | |
| Vehicle | NA | 50 | 5.9 ± 0.75 | |
| compound no 43 | 3 | 50 | 4.0 ± 0.70 | 32 |

Values are Mean ± SEM;
NA: Not applicable

Figure 1B:
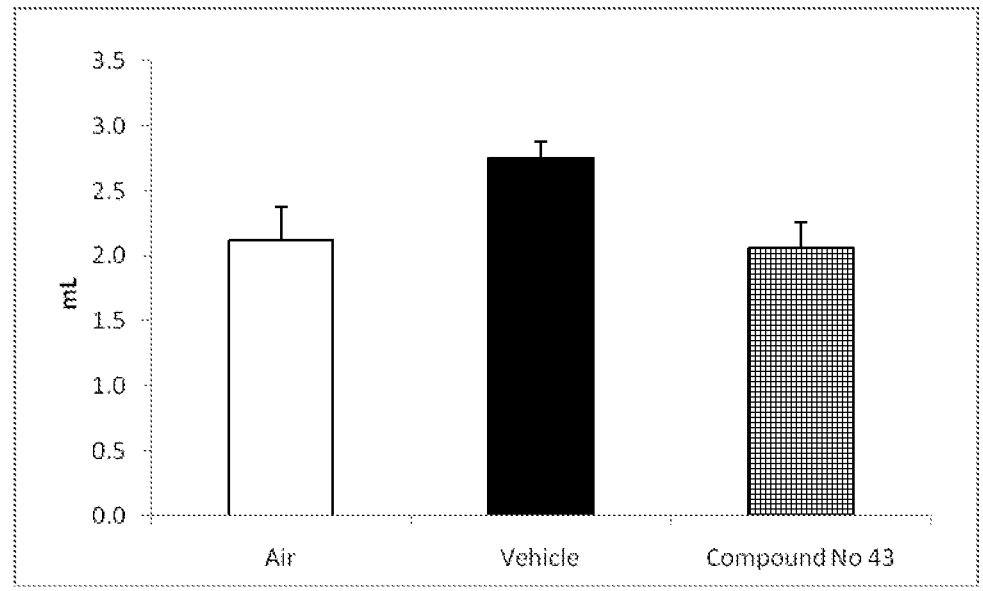
FIG. 1B illustrates the effect of treatment of compound no. 43 on the lung function parameter of residual volume of lungs.
Figure 2A:
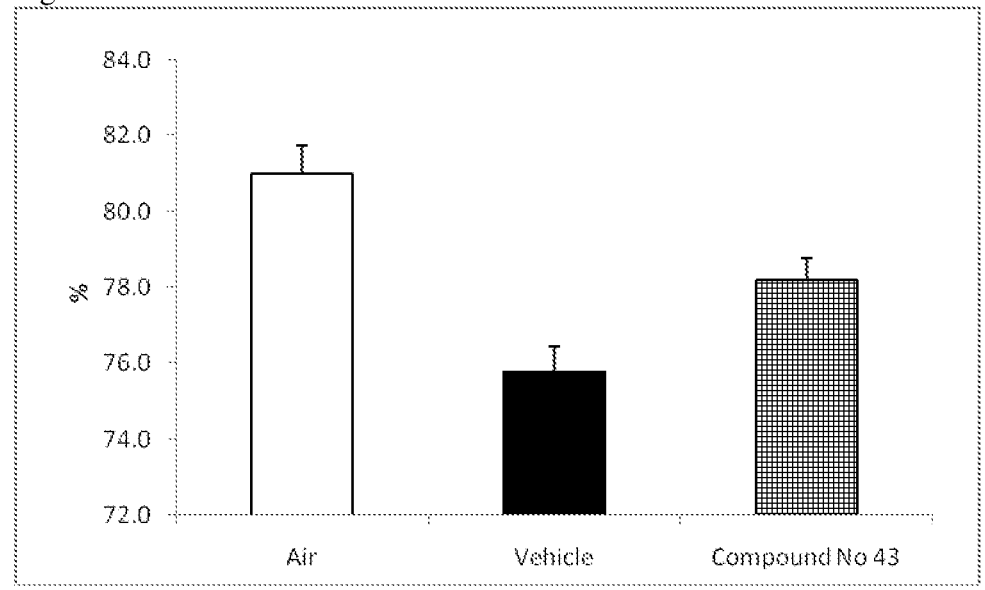
FIG. 2A illustrates the effect of treatment of compound no. 43 on the lung function parameter of inspiratory capacity (IC) to total lung capacity (TLC) ratio.
Figure 2B:
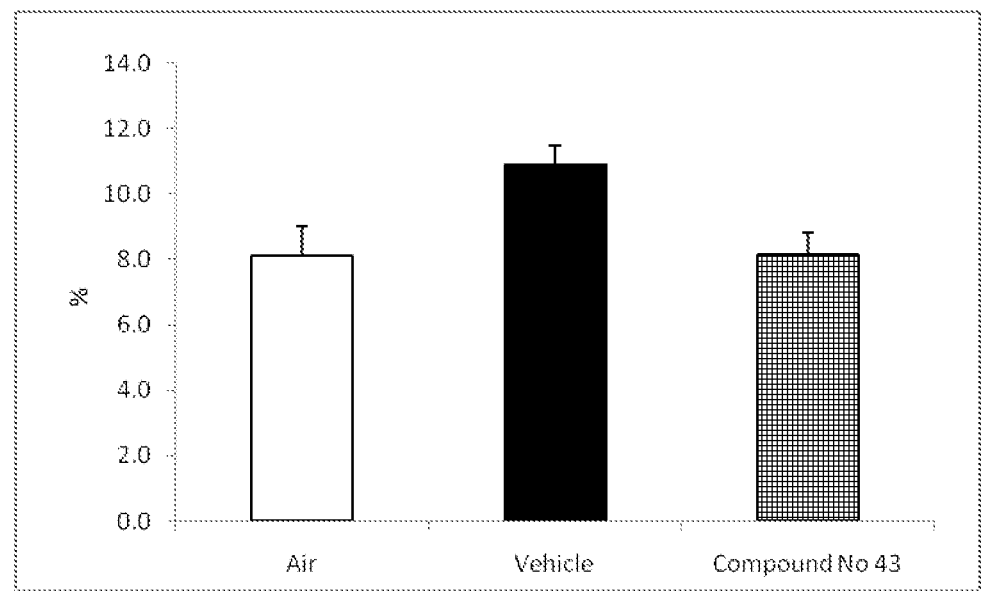
FIG. 2B illustrates the effect of treatment of compound no. 43 on the lung function parameter of residual volume (RV) to total lung capacity (TLC) ratio.

B. Effect of treatment of compound no 43, on lung function parameters, Functional Residual Capacity (FRC), Residual Volume (RV), Inspiratory Capacity (IC) to Total Lung Capacity (TLC) ratio and Residual volume (RV) to total lung capacity (TLC) ratio is given in FIGS. 1A, 1B, 2A, and 2B. (Values are Mean+SEM)

Observation: In a chronic COPD model, compound of present invention exerted effect in reduction of neutrophil influx to lung tissue, significantly improves lung function aspects associated with COPD.

The invention claimed is:
1. A compound of formula (I):

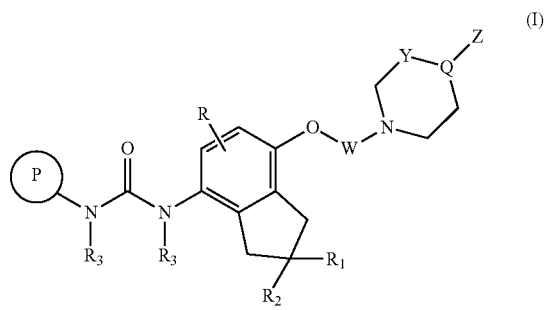

(I)

or a pharmaceutically acceptable salt, stereoisomer or tautomer thereof,
wherein:
Y is C=O or C(Z');
Q is C or N;
when Y is C=O, then Q is N;
when Y is C=O, Z is selected from hydrogen, —($C_1$-$C_6$)alkyl, branched-($C_3$-$C_6$)alkyl, —($C_3$-$C_6$)cycloalkyl, —($C_1$-$C_3$)alkyl($C_3$-$C_6$)cycloalkyl, —($C_1$-$C_6$)alkyl-OH, —($C_1$-$C_6$)alkyl-SH, —C(O)$CH_2R_4$, —($C_1$-$C_6$)alkyl-$NR_5R_6$, —($C_1$-$C_6$)alkyl-aryl, —($C_1$-$C_6$)alkyl-heteroaryl, —($C_1$-$C_6$)alkyl-$CO_2$H, —($C_1$-$C_6$)alkyl-$CO_2R_7$, —($C_1$-$C_6$)alkyl-C(O)$NR_5R_6$, —C(O)$NR_5R_6$, —$CO_2R_7$, —$COR_7$, —($C_1$-$C_6$)alkyl-$OR_7$, —($C_1$-$C_6$)alkyl-S(O)$_nR_7$, —S(O)$_m$—$R_7$, —S(O)$_m$N($R_3$)—$R_7$, —S(O)$_m$$NR_5R_6$, aryl and heteroaryl, wherein: said aryl or heteroaryl may be further optionally substituted by 1-3 substituents independently selected from $R_8$;
or when Y is C(Z'), Z and Z' together forms a 5 or 6 membered aromatic ring system having 1 to 3 heteroatoms independently selected from O, S(O)$_n$ or N and said ring is optionally substituted by 1-3 substituents independently selected from $R_8$;
P is a cyclic ring, which is selected from

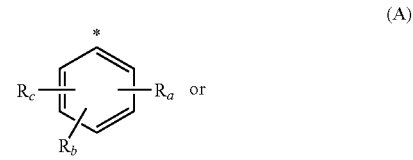

(A)

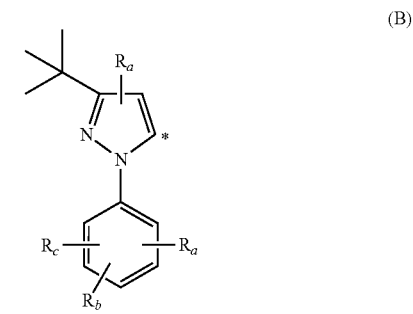

(B)

where * denotes the point of attachment to the urea nitrogen in formula (I):
$R_a$, $R_b$, and $R_c$ are independently selected from hydrogen, halogen, —($C_1$-$C_6$)alkyl, branched-($C_3$-$C_6$)alkyl, —(C₃-C₆)cycloalkyl, aryl, heteroaryl, heterocyclyl, —(C₁-C₆)alkyl-aryl, —(C₁-C₆)alkyl-heteroaryl, hydroxy, —CF₃, —OCF₃, —NO₂, —C(O)—(C₁-C₆)alkyl, —C(O)—(C₃-C₆)cycloalkyl, —C(O)CH₂R₄, —NR₅R₆, —N(R₃)C(O)—R₇, —N(R₃)S(O)ₘ—R₇, —N(R₃)C(O)—N(R₃)—R₇, —N(R₃)C(S)N(R₃)—R₇, —OR₇, —CO₂H, —CO₂R₇, —C(O)—NR₅R₆, —SH, —S(O)ₙ—R₇, —S(O)ₘN(R₃)—R₇, —S(O)ₘ—NR₅R₆, —CN, —CHO, —(C₁-C₆)alkyl-R₄ and —(C₁-C₆)alkyl-NR₅R₆, wherein each aryl, heterocyclyl or heteroaryl may be further optionally substituted with 1-3 substituents independently selected from halogen, —(C₁-C₆)alkyl, branched-(C₃-C₆)alkyl, aryl, heteroaryl, heterocyclyl, hydroxy, —CF₃, —OCF₃, —OR₇, —O—(C₁-C₆)alkyl-R₈, —NO₂, —C(O)—(C₁-C₆)alkyl, —C(O)CH₂R₄, —NR₅R₆, —CO₂H, —CO₂R₇, —C(O)NR₅R₆, —N(R₃)C(O)—R₇, —N(R₃)S(O)ₘ—R₇, —SH, —S(O)ₙ—R₇, —S(O)ₘN(R₃)—R₇, —CN, —CHO, —(C₁-C₆)alkyl-OR₇, —(C₁-C₆)alkyl-halogen and —(C₁-C₆)alkyl-NR₅R₆; or any two substituents of Rₐ, R_b, and R_c may form a saturated, partially saturated or unsaturated monocyclic ring, which may contain 0, 1, 2 or 3 ring heteroatoms selected from O, S(O)ₙ or N;

W is —(CH₂)ₜ, —(CH₂)ₘCO or —(CH₂)ₘS(O)ₘ;

R is selected from hydrogen, —(C₁-C₆)alkyl, branched-(C₃-C₆)alkyl, halogen, —O(C₁-C₆)alkyl, —CF₃, —OCF₃ and hydroxy;

R₁ and R₂ are independently selected from hydrogen, hydroxy, —(C₁-C₃)alkyl, branched-(C₃-C₆)alkyl and —(C₃-C₆)cycloalkyl;

R₃ is independently selected from hydrogen, —(C₁-C₃)alkyl, branched-(C₃-C₆)alkyl, —(C₁-C₃)alkyl(C₃-C₆)cycloalkyl and glucuronate;

R₄ is independently selected from hydroxy, —SH, —OR₇, —NR₅R₆, —S(O)ₙ—R₇, —S(O)ₙ—(C₁-C₆)alkyl-CO₂(C₁-C₆)alkyl, —S(O)ₙ—(C₁-C₆)alkyl-OH, —S(O)ₙ—(C₁-C₆)alkyl-CO₂H, —N(R₃)C(O)—R₇, —N(R₃)S(O)ₘ—R₇, —O—(C₁-C₆)alkyl-CO₂(C₁-C₆)alkyl, —O—(C₁-C₆)alkyl-OH and —O—(C₁-C₆)alkyl-CO₂H;

R₅ and R₆ are independently selected from hydrogen, —(C₁-C₆)alkyl, branched-(C₃-C₆)alkyl, —COR₇, —C(O)NR₅R₆, —S(O)ₘR₇, —(C₁-C₆)alkyl-(C₃-C₆)cycloalkyl, —(C₃-C₆)cycloalkyl, aryl and heteroaryl or R₅ and R₆ are taken together with nitrogen to form a 3 to 8 membered monocyclic or 8 to 12 membered bicyclic heterocycle ring, wherein said monocyclic or bicyclic ring contains 0, 1, 2 or 3 ring heteroatoms selected from O, S(O)ₙ or N and said monocyclic or bicyclic ring is optionally substituted by 1-3 substituents independently selected from R₈;

R₇ is independently selected from —(C₁-C₆)alkyl, —(C₁-C₆)alkyl-OH, branched-(C₃-C₆)alkyl, —(C₃-C₆)cycloalkyl, —(C₁-C₆)alkyl-(C₃-C₆)cycloalkyl, aryl and heteroaryl;

R₈ is independently selected from hydrogen, halogen, hydroxy, —CN, —CHO, —NO₂, —(C₁-C₆)alkyl, —(C₃-C₆)cycloalkyl, —(C₁-C₆)alkyl-(C₃-C₆)cycloalkyl, aryl, heteroaryl, heterocyclyl, —C(O)CH₂R₄, —OR₇, —SH, —S(O)ₙ—R₇, —CF₃, —OCF₃, —CO₂H, —COR₇, —CO₂R₇, —C(O)NR₅R₆, —S(O)ₘN(R₃)—R₇ and —NR₅R₆, wherein said (C₁-C₆)alkyl, aryl, heterocyclyl and heteroaryl may be further substituted with 1-3 substituents independently selected from R₉;

R₉ is independently selected from R₇, halogen, hydroxy, —(C₁-C₆)alkyl-OH, —NO₂, —SH, —OR₇, —O(C₁-C₆)alkyl-R₄, —OC(O)—R₇, —O(C₁-C₆)alkyl-CO₂R₇, —O(C₁-C₆)alkyl-CO₂H, —O(C₁-C₆)alkyl-C(O)—NR₅R₆, —OS(O)ₘ—R₇, —CO₂R₇, —CO₂H, —C(O)—R₇, —C(O)—NR₅R₆, —S(O)ₙ—R₇, —S(O)ₙ(C₁-C₆)alkyl-R₄, —S(O)ₙ(C₁-C₆)alkyl-C(O)NR₅R₆, —S(O)ₙ(C₁-C₆)alkyl-CO₂R₇, —S(O)ₙ(C₁-C₆)alkyl-CO₂H, —NR₅R₆, —S(O)ₘ—NR₅R₆, —N(R₃)C(O)—R₇, —N(R₃)C(O)N(R₃)—R₇, —N(R₃)C(S)N(R₃)—R₇, —N(R₃)C(O)(C₁-C₆)alkyl-aryl, —N(R₃)S(O)ₘ—R₇, OSO₃H and O-glucuronate;

m is 1 or 2;
n is 0, 1 or 2; and
t is 2 or 3.

2. The compound as claimed in claim 1, wherein Q is N.

3. The compound as claimed in claim 1, wherein:
Y is C=O or C(Z');
Q is C or N;
when Y is C=O, then Q is N;
when Y is C=O, Z is selected from hydrogen, —(C₁-C₆)alkyl, branched-(C₃-C₆)alkyl, —(C₃-C₆)cycloalkyl, —(C₁-C₃)alkyl(C₃-C₆)cycloalkyl, —(C₁-C₆)alkyl-OH, —(C₁-C₆)alkyl-aryl, —(C₁-C₆)alkyl-C(O)NR₅R₆, S(O)ₘ—R₇ and aryl;
or when Y is C(Z'), Z and Z' together forms a 5 or 6 membered aromatic ring system having 1 to 3 heteroatoms independently selected from S(O)ₙ or N and said ring is optionally substituted by 1-2 substituents independently selected from R₈;
P is a cyclic ring, which is selected from

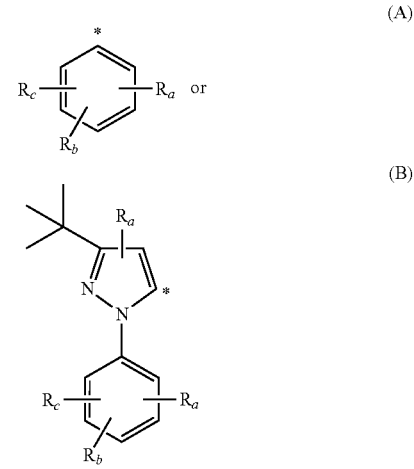

where * denotes the point of attachment to the urea nitrogen in formula (I);

Rₐ, R_b, and R_c are independently selected from hydrogen, halogen, —(C₁-C₆)alkyl, branched-(C₃-C₆)alkyl, —(C₃-C₆)cycloalkyl, hydroxy, —N(R₃)S(O)ₘ—R₇, —N(R₃)COR₇ and —OR₇;

W is —(CH₂)ₜ or —(CH₂)ₘCO;

R is hydrogen or —(C₁-C₆)alkyl;

R₁ and R₂ are independently selected from hydrogen and hydroxy;

R₃ is independently selected from hydrogen and glucuronate;

R₄ is selected from hydroxy, and —NR₅R₆;

R$_5$ and R$_6$ are independently selected from hydrogen, —(C$_1$-C$_6$)alkyl and —COR$_7$; or R$_5$ and R$_6$ are taken together with nitrogen to form a 3 to 8 membered monocyclic heterocycle ring, wherein said monocyclic ring contains 0, 1, 2 or 3 ring heteroatoms selected from O or N;

R$_7$ is independently selected from —(C$_1$-C$_6$)alkyl, —(C$_3$-C$_6$)cycloalkyl, —(C$_1$-C$_6$)alkyl-OH and branched-(C$_3$-C$_6$)alkyl;

R$_8$ is independently selected from hydrogen, —(C$_3$-C$_6$) cycloalkyl, aryl, heteroaryl, —CF$_3$, —CO$_2$R$_7$ and —NR$_5$R$_6$, wherein said aryl or heteroaryl may be further substituted with 1-3 substituents selected from R$_9$;

R$_9$ is independently selected from halogen, R$_7$, hydroxy, —OR$_7$, —O(C$_1$-C$_6$)alkyl-R$_4$, —S(O)$_n$—R$_7$, —S(O)$_n$ (C$_1$-C$_6$)alkyl-R$_4$, —(C$_1$-C$_6$)alkyl-OH and O-glucuronate;

m is 1 or 2;

n is 0; and t is 2 or 3.

4. The compound as claimed in claim 1, which is selected from the group consisting of:

1-[3-tert-butyl-1-(4-methylphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-tert-butylphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-cyclohexylphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea;

1-(3-tert-butyl-1-phenyl-1H-pyrazol-5-yl)-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea;

1-(3-tert-butyl-1-phenyl-1H-pyrazol-5-yl)-3-(7-{2-[3-(2-methoxyphenyl)-5,6-dihydro[1,2,4]triazolo[4,3-a]pyrazin-7(8H)-yl]-2-oxoethoxy}-2,3-dihydro-1H-inden-4-yl)urea;

1-[3-tert-butyl-1-(4-methylphenyl)-1H-pyrazol-5-yl]-3-(7-{2-[4-(2-hydroxyethyl)-3-oxopiperazin-1-yl]ethoxy}-2,3-dihydro-1H-inden-4-yl)urea;

1-(3-tert-butyl-1-phenyl-1H-pyrazol-5-yl)-3-[7-(2-{3-[2-(methylsulfanyl)phenyl]-5,6-dihydro[1,2,4]triazolo[4,3-a]pyrazin-7(8H)-yl})-2-oxoethoxy)-2,3-dihydro-1H-inden-4-yl]urea;

1-[3-tert-butyl-1-(3-chloro-4-hydroxyphenyl)-1H-pyrazol-5-yl]-3-(7-{2-[3-(2-methoxyphenyl)-5,6-dihydro[1,2,4]triazolo[4,3-a]pyrazin-7(8H)-yl]-2-oxoethoxy}-2,3-dihydro-1H-inden-4-yl)urea;

1-[3-tert-butyl-1-(3-chloro-4-hydroxyphenyl)-1H-pyrazol-5-yl]-3-[7-(2-{3-[2-(methylsulfanyl)phenyl]-5,6-dihydro[1,2,4]triazolo[4,3-a]pyrazin-7(8H)-yl]-2-oxoethoxy)-2,3-dihydro-1H-inden-4-yl]urea;

1-[3-tert-butyl-1-(4-methylphenyl)-1H-pyrazol-5-yl]-3-[7-(2-{3-[2-(methylsulfanyl)phenyl]-5,6-dihydro[1,2,4]triazolo[4,3-a]pyrazin-7(8H)-yl})-2-oxoethoxy)-2,3-dihydro-1H-inden-4-yl]urea;

1-(3-tert-butyl-1-phenyl-1H-pyrazol-5-yl)-3-(7-{2-[3-(2-{[2-(morpholin-4-yl)ethyl]sulfanyl}phenyl]-5,6-dihydro[1,2,4]triazolo[4,3-a]pyrazin-7(8H)-yl]-2-oxoethoxy}-2,3-dihydro-1H-inden-4-yl)urea;

1-[3-tert-butyl-1-(4-methylphenyl)-1H-pyrazol-5-yl]-3-(7-{2-[4-(cyclopropylmethyl)-3-oxopiperazin-1-yl]ethoxy}-2,3-dihydro-1H-inden-4-yl)urea;

1-[3-tert-butyl-1-(4-methylphenyl)-1H-pyrazol-5-yl]-3-[7-(2-{3-[2-(methylsulfanyl)phenyl]-5,6-dihydro[1,2,4]triazolo[4,3-a]pyrazin-7(8H)-yl}ethoxy)-2,3-dihydro-1H-inden-4-yl]urea;

1-[3-tert-butyl-1-(4-methylphenyl)-1H-pyrazol-5-yl]-3-(7-{2-[3-(2-methoxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-(7-{2-[3-(2-hydroxyphenyl)-5,6-dihydro[1,2,4]triazolo[4,3-a]pyrazin-7(8H)-yl]ethoxy}-2,3-dihydro-1H-inden-4-yl)urea;

1-{7-[2-(4-benzyl-3-oxopiperazin-1-yl)ethoxy]-2,3-dihydro-1H-inden-4-yl}-3-[3-tert-butyl-1-(4-methylphenyl)-1H-pyrazol-5-yl]urea;

1-[3-tert-butyl-1-(4-methoxyphenyl)-1H-pyrazol-5-yl]-3-(7-{2-[4-(cyclopropylmethyl)-3-oxopiperazin-1-yl]ethoxy}-2,3-dihydro-1H-inden-4-yl)urea;

1-[3-tert-butyl-1-(4-hydroxyphenyl)-1H-pyrazol-5-yl]-3-(7-{2-[4-(cyclopropylmethyl)-3-oxopiperazin-1-yl]ethoxy}-2,3-dihydro-1H-inden-4-yl)urea;

1-[3-tert-butyl-1-(4-methylphenyl)-1H-pyrazol-5-yl]-3-{7-[2-(3-oxo-4-phenylpiperazin-1-yl)ethoxy]-2,3-dihydro-1H-inden-4-yl}urea;

1-[3-tert-butyl-1-(4-methylphenyl)-1H-pyrazol-5-yl]-3-(7-{2-[3-{2-[2-(morpholin-4-yl)ethoxy]phenyl}-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-(7-{2-[4-(cyclopentylmethyl)-3-oxopiperazin-1-yl]ethoxy}-2,3-dihydro-1H-inden-4-yl)urea;

1-[3-tert-butyl-1-(4-methylphenyl)-1H-pyrazol-5-yl]-3-(7-{2-[4-(cyclobutylmethyl)-3-oxopiperazin-1-yl]ethoxy}-2,3-dihydro-1H-inden-4-yl)urea;

1-[3-tert-butyl-1-(4-ethylphenyl)-1H-pyrazol-5-yl]-3-(7-{2-[3-(2-methoxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(3-chloro-4-hydroxyphenyl)-1H-pyrazol-5-yl]-3-[7-(2-{3-[2-(methylsulfanyl)phenyl]-5,6-dihydro[1,2,4]triazolo[4,3-a]pyrazin-7(8H)-yl}ethoxy)-2,3-dihydro-1H-inden-4-yl]urea;

1-[3-tert-butyl-1-(3-chloro-4-hydroxyphenyl)-1H-pyrazol-5-yl]-3-(7-{2-[3-(2-methoxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(3-chloro-4-hydroxyphenyl)-1H-pyrazol-5-yl]-3-(7-{2-[3-(2-hydroxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(3-chloro-4-hydroxyphenyl)-1H-pyrazol-5-yl]-3-(7-{2-[3-(2-propoxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-(7-{3-[4-(cyclopropylmethyl)-3-oxopiperazin-1-yl]propoxy}-2,3-dihydro-1H-inden-4-yl)urea;

1-[3-tert-butyl-1-(4-methylphenyl)-1H-pyrazol-5-yl]-3-(7-{2-[3-(3-chloro-2-hydroxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-[7-(2-{3-[2-(2-hydroxyethoxy)phenyl]-5,6-dihydro[1,2,4]triazolo[4,3-a]pyrazin-7(8H)-yl}ethoxy)-2,3-dihydro-1H-inden-4-yl]urea;

1-[3-tert-butyl-1-(4-methylphenyl)-1H-pyrazol-5-yl]-3-(7-{2-[3-(3-chloro-4-hydroxyphenyl)-5,6-dihydro[1,2,4]triazolo[4,3-a]pyrazin-7(8H)-yl]ethoxy}-2,3-dihydro-1H-inden-4-yl)urea;

1-(7-{2-[3-(2-butoxyphenyl)-5,6-dihydro[1,2,4]triazolo[4,3-a]pyrazin-7(8H)-yl]ethoxy}-2,3-dihydro-1H-inden-4-yl)-3-[3-tert-butyl-1-(4-methylphenyl)-1H-pyrazol-5-yl]urea;

1-[3-tert-butyl-1-(4-methylphenyl)-1H-pyrazol-5-yl]-3-[7-(2-{3-[2-(propylsulfanyl)phenyl]-5,6-dihydro[1,2,4]triazolo[4,3-a]pyrazin-7(8H)-yl}ethoxy)-2,3-dihydro-1H-inden-4-yl]urea;

1-[3-tert-butyl-1-(4-methylphenyl)-1H-pyrazol-5-yl]-3-(7-{2-[3-(4-hydroxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(3-chloro-4-hydroxyphenyl)-1H-pyrazol-5-yl]-3-[7-(2-{3-[2-(propylsulfanyl)phenyl]-5,6-dihydro[1,2,4]triazolo[4,3-a]pyrazin-7(8H)-yl}ethoxy)-2,3-dihydro-1H-inden-4-yl]urea;

1-[3-tert-butyl-1-(4-methylphenyl)-1H-pyrazol-5-yl]-3-(7-{2-[3-(3-hydroxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-(7-{2-[3-(2,4-dihydroxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-4-yl]-3-(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)urea;

N-(5-tert-butyl-3-{[(7-{2-[4-(cyclopropylmethyl)-3-oxopiperazin-1-yl]ethoxy}-2,3-dihydro-1H-inden-4-yl)carbamoyl]amino}-2-methoxyphenyl)methanesulfonamide;

N-(5-tert-butyl-3-{[(7-{2-[3-(2-hydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)methanesulfonamide;

N-(5-tert-butyl-3-{[(7-{3-[4-(cyclopropylmethyl)-3-oxopiperazin-1-yl]propoxy}-2,3-dihydro-1H-inden-4-yl)carbamoyl]amino}-2-methoxyphenyl) methanesulfonamide;

N-[5-tert-butyl-2-methoxy-3-({[7-(2-{3-[2-(propylsulfanyl)phenyl]-5,6-dihydro[1,2,4]triazolo[4,3-a]pyrazin-7(8H)-yl}ethoxy)-2,3-dihydro-1H-inden-4-yl]carbamoyl}amino)phenyl]methanesulfonamide;

N-(5-tert-butyl-3-{[(7-{2-[4-(cyclopropylmethyl)-3-oxopiperazin-1-yl]ethoxy}-2,3-dihydro-1H-inden-4-yl)carbamoyl]amino}-2-methoxyphenyl)ethanesulfonamide;

N-{5-tert-butyl-3-[({7-[2-(4-butyl-3-oxopiperazin-1-yl)ethoxy]-2,3-dihydro-1H-inden-4-yl}carbamoyl)amino]-2-methoxyphenyl} methanesulfonamide;

N-[5-tert-butyl-2-methoxy-3-({[7-(2-{3-[2-(methylsulfanyl)phenyl]-5,6-dihydro[1,2,4]triazolo[4,3-a]pyrazin-7(8H)-yl}ethoxy)-2,3-dihydro-1H-inden-4-yl]carbamoyl}amino)phenyl]ethanesulfonamide;

N-(5-tert-butyl-3-{[(7-{2-[3-(3-hydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)methanesulfonamide;

N-(5-tert-butyl-3-{[(7-{2-[3-{4-[(2-{4-[(2-hydroxyethyl)sulfanyl]phenyl}-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)methanesulfonamide;

N-(5-tert-butyl-3-{[(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)methanesulfonamide;

N-(5-tert-butyl-3-{[(7-{2-[3-(2,4-dihydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)ethanesulfonamide;

N-[5-tert-butyl-2-methoxy-3-({[7-(2-{3-[2-(propylsulfanyl)phenyl]-5,6-dihydro[1,2,4]triazolo[4,3-a]pyrazin-7(8H)-yl}ethoxy)-2,3-dihydro-1H-inden-4-yl]carbamoyl}amino)phenyl]ethanesulfonamide;

N-(5-tert-butyl-3-{[(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)carbamoyl]amino}-2-methoxyphenyl)ethanesulfonamide;

N-[5-({[7-({[3-tert-butyl-1-(4-methylphenyl)-1H-pyrazol-5-yl]carbamoyl}amino)-2,3-dihydro-1H-inden-4-yl]oxy}acetyl)-4,5,6,7-tetrahydrothieno[3,2-c]pyridin-2-yl]acetamide;

1-[3-tert-butyl-1-(3-chloro-4-methoxyphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea;

ethyl 6-({[7-({[3-tert-butyl-1-(4-methylphenyl)-1H-pyrazol-5-yl]carbamoyl}amino)-2,3-dihydro-1H-inden-4-yl]oxy}acetyl)-2-[(cyclopropylcarbonyl)amino]-4,5,6,7-tetrahydrothieno[2,3-c]pyridine-3-carboxylate;

N-[5-({[7-({[3-tert-butyl-1-(4-cyclohexylphenyl)-1H-pyrazol-5-yl]carbamoyl}amino)-2,3-dihydro-1H-inden-4-yl]oxy}acetyl)-4,5,6,7-tetrahydrothieno[3,2-c]pyridin-2-yl]acetamide;

1-[3-tert-butyl-1-(3-chloro-4-methylphenyl)-1H-pyrazol-5-yl]-3-(7-{2-oxo-2-[3-(trifluoromethyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-{7-[2-oxo-2-(3-phenyl-5,6-dihydro[1,2,4]triazolo[4,3-a]pyrazin-7(8H)-yl)ethoxy]-2,3-dihydro-1H-inden-4-yl}urea;

1-(3-tert-butyl-1-phenyl-1H-pyrazol-5-yl)-3-(7-{2-[3-(3-chloro-4-methoxyphenyl)-5,6-dihydro[1,2,4]triazolo[4,3-a]pyrazin-7(8H)-yl]-2-oxoethoxy}-2,3-dihydro-1H-inden-4-yl)urea;

1-[3-tert-butyl-1-(4-methylphenyl)-1H-pyrazol-5-yl]-3-{7-[2-(3-oxo-4-propylpiperazin-1-yl)ethoxy]-2,3-dihydro-1H-inden-4-yl}urea;

1-[3-tert-butyl-1-(4-fluorophenyl)-1H-pyrazol-5-yl]-3-(7-{2-[4-(cyclopropylmethyl)-3-oxopiperazin-1-yl]ethoxy}-2,3-dihydro-1H-inden-4-yl)urea;

1-(3-tert-butyl-1-phenyl-1H-pyrazol-5-yl)-3-(7-{2-[4-(cyclopropylmethyl)-3-oxopiperazin-1-yl]ethoxy}-2,3-dihydro-1H-inden-4-yl)urea;

1-[3-tert-butyl-1-(2-methylphenyl)-1H-pyrazol-5-yl]-3-(7-{2-[4-(cyclopropylmethyl)-3-oxopiperazin-1-yl]ethoxy}-2,3-dihydro-1H-inden-4-yl)urea;

1-[3-tert-butyl-1-(3-chloro-4-hydroxyphenyl)-1H-pyrazol-5-yl]-3-(7-{2-[3-(2,4-dihydroxyphenyl)-5,6-dihydro[1,2,4]triazolo[4,3-a]pyrazin-7(8H)-yl]ethoxy}-2,3-dihydro-1H-inden-4-yl)urea;

N-(5-tert-butyl-3-{[(7-{2-[4-(cyclopropylmethyl)-3-ox-opiperazin-1-yl]ethoxy}-2,3-dihydro-1H-inden-4-yl)carbamoyl]amino}-2-methoxyphenyl)cyclopropanecarboxamide;

1-[3-tert-butyl-1-(3-chloro-4-hydroxyphenyl)-1H-pyrazol-5-yl]-3-{7-[2-(3-cyclohexyl-5,6-dihydro[1,2,4]triazolo[4,3-a]pyrazin-7(8H)-yl)ethoxy]-2,3-dihydro-1H-inden-4-yl}urea;

1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-6-methyl-2,3-dihydro-1H-inden-4-yl)urea;

1-[3-tert-butyl-1-(4-methylphenyl)-1H-pyrazol-5-yl]-3-(7-{2-[3-(naphthalen-1-yl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-{7-[2-(3-cyclohexyl-5,6-dihydro[1,2,4]triazolo[4,3-a]pyrazin-7(8H)-yl)ethoxy]-2,3-dihydro-1H-inden-4-yl}urea;

1-[3-tert-butyl-1-(4-methylphenyl)-1H-pyrazol-5-yl]-3-(7-{2-[3-(3-methyl-1-benzofuran-2-yl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(3,4,5-trimethoxyphenyl)-1H-pyrazol-5-yl]-3-(7-{2-[4-(cyclopropylmethyl)-3-oxopiperazin-1-yl]ethoxy}-2,3-dihydro-1H-inden-4-yl)urea;

1-[3-tert-butyl-1-(4-methylphenyl)-1H-pyrazol-5-yl]-3-(7-{2-[4-(cyclopropylmethyl)-3-oxopiperazin-1-yl]ethoxy}-2,3-dihydro-1H-inden-4-yl)urea methanesulfonate (1:1);

N-{5-tert-butyl-3-[({7-[2-(3-cyclohexyl-5,6-dihydro[1,2,4]triazolo[4,3-a]pyrazin-7(8H)-yl)ethoxy]-2,3-dihydro-1H-inden-4-yl}carbamoyl)amino]-2-methoxyphenyl}methanesulfonamide;

N-(5-tert-butyl-3-{[(7-{2-[3-(5-chloro-2-hydroxyphenyl)-5,6-dihydro[1,2,4]triazolo[4,3-a]pyrazin-7(8H)-yl]ethoxy}-6-methyl-2,3-dihydro-1H-inden-4-yl)carbamoyl]amino}-2-methoxyphenyl)methanesulfonamide;

N-(5-tert-butyl-2-methoxy-3-{[(7-{2-[3-(naphthalen-1-yl)-5,6-dihydro[1,2,4]triazolo[4,3-a]pyrazin-7(8H)-yl]ethoxy}-2,3-dihydro-1H-inden-4-yl)carbamoyl]amino}phenyl)methanesulfonamide;

1-[3-tert-butyl-1-(4-methylphenyl)-1H-pyrazol-5-yl]-3-(7-{2-[4-(ethylsulfonyl)-3-oxopiperazin-1-yl]ethoxy}-2,3-dihydro-1H-inden-4-yl)urea;

2-[7-(2-{[7-({[3-tert-butyl-1-(4-methylphenyl)-1H-pyrazol-5-yl]carbamoyl}amino)-2,3-dihydro-1H-inden-4-yl]oxy}ethyl)-5,6,7,8-tetrahydro[1,2,4]triazolo[4,3-a]pyrazin-3-yl]-4-chlorophenyl hexopyranosiduronic acid;

N-{[3-tert-butyl-1-(4-methylphenyl)-1H-pyrazol-5-yl]carbamoyl}-N-(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)hexopyranuronosylamine;

N-[3-tert-butyl-1-(4-methylphenyl)-1H-pyrazol-5-yl]-N-[(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)carbamoyl]hexopyranuronosylamine;

2-{4-[2-({7-[({5-tert-butyl-2-methoxy-3-[(methyl sulfonyl)amino]phenyl}) carbamoyl)amino]-2,3-dihydro-1H-inden-4-yl}oxy)ethyl]-2-oxopiperazin-1-yl}-N,N-dimethylacetamide;

2-[4-(2-{[7-({[3-tert-butyl-1-(4-methylphenyl)-1H-pyrazol-5-yl]carbamoyl}amino)-2,3-dihydro-1H-inden-4-yl]oxy}ethyl)-2-oxopiperazin-1-yl]-N,N-dimethylacetamide;

N-{5-tert-butyl-3-[({7-[2-(4-cyclopropyl-3-oxopiperazin-1-yl)ethoxy]-2,3-dihydro-1H-inden-4-yl})carbamoyl)amino]-2-methoxyphenyl}methanesulfonamide;

N-(5-tert-butyl-3-{[(7-{2-[4-(cyclopropylmethyl)-3-oxopiperazin-1-yl]ethoxy}-2,3-dihydro-1H-inden-4-yl)carbamoyl]amino}-2-hydroxyphenyl)ethanesulfonamide;

N-(5-tert-butyl-3-{[(7-{2-[4-(cyclopropylmethyl)-3-oxopiperazin-1-yl]ethoxy}-2,3-dihydro-1H-inden-4-yl)carbamoyl]amino}-2-methoxyphenyl)ethenesulfonamide;

1-[3-tert-butyl-1-(4-methylphenyl)-1H-pyrazol-5-yl]-3-[7-(2-{3-[2-(hydroxymethyl)phenyl]-5,6-dihydro[1,2,4]triazolo[4,3-a]pyrazin-7(8H)-yl}ethoxy)-2,3-dihydro-1H-inden-4-yl]urea;

1-[3-tert-butyl-1-(4-methylphenyl)-1H-pyrazol-5-yl]-3-(7-{3-[3-(5-chloro-2-hydroxyphenyl)-5,6-dihydro[1,2,4]triazolo[4,3-a]pyrazin-7(8H)-yl]propoxy}-2,3-dihydro-1H-inden-4-yl)urea;

1-[3-tert-butyl-1-(4-methylphenyl)-1H-pyrazol-5-yl]-3-(7-{2-[3-(pyridin-2-yl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-(7-{2-[3-(2-ethylphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-(7-{2-[3-(4-chloro-2-hydroxyphenyl)-5,6-dihydro[1,2,4]triazolo[4,3-a]pyrazin-7(8H)-yl]ethoxy}-2,3-dihydro-1H-inden-4-yl)urea;

1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)urea methanesulfonate;

1-[3-tert-butyl-1-(4-methylphenyl)-1H-pyrazol-5-yl]-3-(7-{2-[3-(5-chloro-2-hydroxyphenyl)-5,6-dihydro[1,2,4]triazolo[4,3-a]pyrazin-7(8H)-yl]ethoxy}-2,3-dihydro-1H-inden-4-yl)urea hydrochloride;

and pharmaceutically acceptable salts thereof.

5. A pharmaceutical composition comprising a therapeutically effective amount of one or more compounds as claimed in claim 1, in admixture with a pharmaceutically acceptable adjuvant or carrier.

6. A method for inhibiting p38 mitogen-activated protein kinase activity in a mammal, comprising administering a therapeutically effective amount of a compound as claimed in claim 1 to a mammal in need thereof.

7. The method as claimed in claim 6, wherein the mammal is a human.

8. The method as claimed in claim 6, wherein the mammal is treated for a disease selected from the group consisting of an allergic airway disease and a non-allergic airway disease.

9. The method as claimed in claim 8, wherein the allergic and non-allergic airway disease is selected from the group consisting of chronic obstructive pulmonary disease and asthma.

10. The method as claimed in claim 8, wherein the mammal is a human.

\* \* \* \* \*